US010144913B1

(12) United States Patent
Medina-Bolivar et al.

(10) Patent No.: US 10,144,913 B1
(45) Date of Patent: Dec. 4, 2018

(54) METHOD TO INCREASE THE YIELD OF PRODUCTS IN PLANT MATERIAL

(71) Applicant: Arkansas State University-Jonesboro, State University, AR (US)

(72) Inventors: Luis Fabricio Medina-Bolivar, Memphis, TN (US); Tianhong Yang, Jonesboro, AR (US)

(73) Assignee: Arkansas State University-Jonesboro, State University, AR (US)

( * ) Notice: Subject to any disclaimer, the term of this patent is extended or adjusted under 35 U.S.C. 154(b) by 0 days.

(21) Appl. No.: 15/457,922

(22) Filed: Mar. 13, 2017

Related U.S. Application Data

(63) Continuation-in-part of application No. 13/784,877, filed on Mar. 5, 2013, now Pat. No. 9,598,707, which is a continuation-in-part of application No. 61/729,659, filed on Nov. 26, 2012.

(51) Int. Cl.
*C12P 17/04* (2006.01)
*C12N 5/00* (2006.01)
*C12N 5/04* (2006.01)
*C12P 17/06* (2006.01)
*C12P 17/18* (2006.01)
*C12P 19/46* (2006.01)
*C12P 7/22* (2006.01)
*G01N 30/72* (2006.01)

(52) U.S. Cl.
CPC ............ *C12N 5/0025* (2013.01); *C12N 5/04* (2013.01); *C12P 7/22* (2013.01); *C12P 17/04* (2013.01); *C12P 17/06* (2013.01); *C12P 17/188* (2013.01); *C12P 19/46* (2013.01); *C12N 5/00* (2013.01); *G01N 30/72* (2013.01)

(58) Field of Classification Search
CPC .......... C12N 5/0025; C12N 5/04; C12N 5/00; C12P 7/22; C12P 17/04; C12P 17/06; C12P 17/188; C12P 19/46; G01N 30/72
USPC .......................................................... 435/53
See application file for complete search history.

(56) References Cited

FOREIGN PATENT DOCUMENTS

EP 2735609 * 5/2014 ............... C12N 5/00

OTHER PUBLICATIONS

Yang et al., A Stilbenoid-Specific Prenyltransferase Utilizes Dimethylallyl Pyrophosphate from the Plastidic Terpenoid Pathway, Plant Physiology, Vo. 171, Aug. 2016, pp. 2483-2498.*

* cited by examiner

*Primary Examiner* — Jennifer M. H. Tichy
(74) *Attorney, Agent, or Firm* — Schrantz Law Firm, PLLC; Stephen D. Schrantz

(57) ABSTRACT

A method or process to increase the production of products of interest in plant material including plant cultures, such as, for example, cell suspension cultures, root cultures, and hairy root cultures is provided. In one embodiment, the method is to contacting the plant material with a precursor or xenobiotic when producing a product of interest from a plant. In another embodiment the plant material is also contacted with a trapping agent. The process may also provide for contacting an elicitor of the product of interest with the plant material. An embodiment provides for contacting an elicitor, precursor and trapping agent with the plant material. The ability to produce novel compounds such as glucosides and glucuronides is provided.

20 Claims, 48 Drawing Sheets

Figure 5
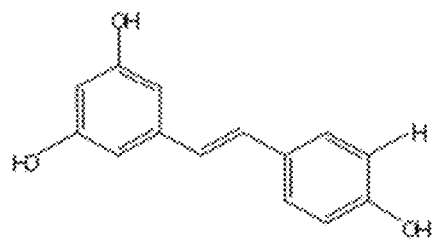
trans-Resveratrol
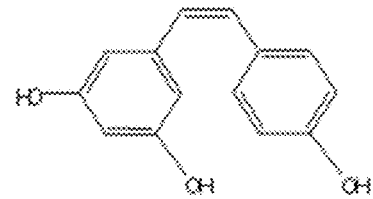
cis-Resveratrol
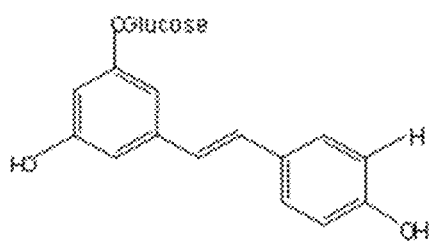
Piceid (polydatin)
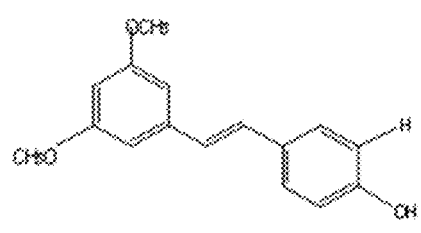
Pterostilbene
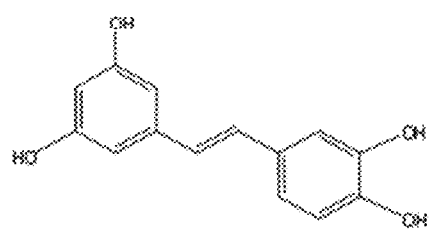
Piceatannol
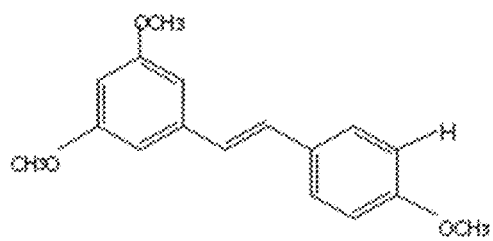
Resveratrol trimethylether

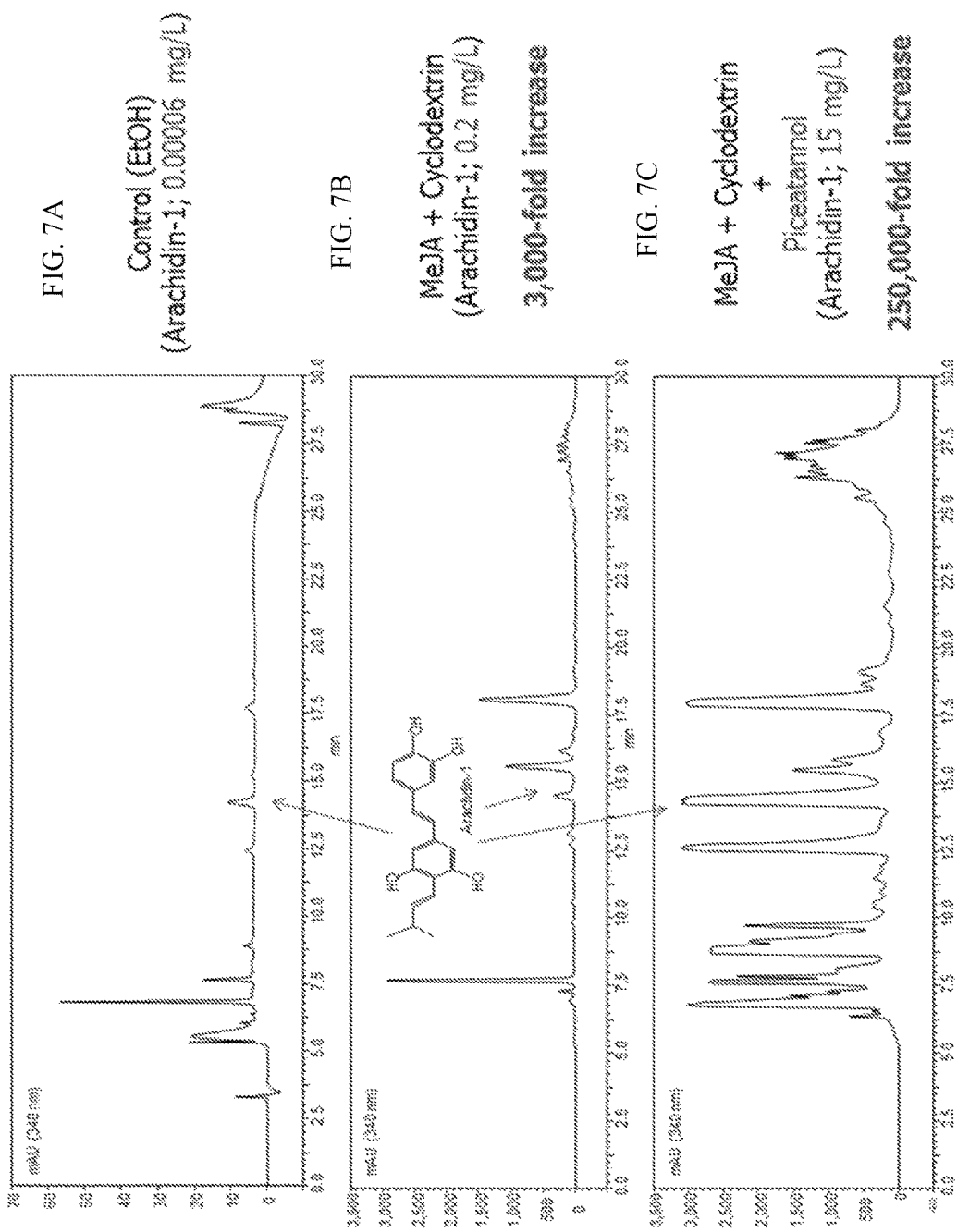

Chrysin
254.24

A

B

| Factors | Levels | | | |
|---|---|---|---|---|
| | 1 | 2 | 3 | 4 |
| methyl-β-cyclodextrin (CD) (g/L) | 4.5 | 9 | 18 | 27 |
| Methyl Jasmonate (MeJA) (μM) | 1 | 10 | 100 | 150 |
| $H_2O_2$ (mM) | 6 | 12 | 60 | 120 |
| $MgCl_2$ (mM) | 0 | 1 | 5 | 10 |

| Run number | MeJA (μM) | H$_2$O$_2$ (mM) | Arachidin-1 (mg/L) 48 h | Arachidin-1 (mg/L) 72 h | Arachidin-3 (mg/L) 48 h | Arachidin-3 (mg/L) 72 h |
|---|---|---|---|---|---|---|
| 1 | 100 | 1.5 | 110.16 | 202.24 | 169.94 | 295.16 |
| 2 | 100 | 3 | 108.57 | 225.60 | 127.89 | 199.35 |
| 3 | 100 | 6 | 99.96 | 224.21 | 136.73 | 233.54 |
| 4 | 125 | 1.5 | 127.01 | 216.74 | 192.61 | 314.30 |
| 5 | 125 | 3 | 107.89 | 231.75 | 182.43 | 300.76 |
| 6 | 125 | 6 | 111.95 | 224.16 | 142.34 | 220.13 |
| 7 | 150 | 1.5 | 128.06 | 225.67 | 193.22 | 310.94 |
| 8 | 150 | 3 | 113.88 | 219.32 | 155.72 | 243.62 |
| 9 | 150 | 6 | 95.17 | 179.79 | 89.88 | 129.87 |

Figure 41

| Treatment Hours | Arachidin-1 (mg/L) | | Arachidin-3 (mg/L) | |
|---|---|---|---|---|
| | 50 mL | 100 mL | 50 mL | 100 mL |
| 48 | 79.34 ± 20.35 | -* | 147.29 ± 62.52 | - |
| 72 | 185.60 ± 65.92 | 112.01 ± 17.44 | 232.83 ± 116.46 | 198.30 ± 39.29 |
| 96 | 252.46 ± 83.23 | - | 275.74 ± 134.62 | - |
| 120 | 282.65 ± 85.06 | 201.27 ± 15.91 | 292.32 ± 143.83 | 325.11 ± 42.11 |
| 144 | 284.84 ± 63.19 | - | 307.70 ± 145.16 | - |
| 168 | 244.69 ± 36.85 | 227.39 ± 12.75 | 304.39 ± 138.55 | 370.59 ± 50.37 |
| 192 | 169.66 ± 41.15 | 222.83 ± 13.67 | 310.57 ± 131.33 | 365.85 ± 50.23 |

-*: No data available.

Figure 45

| Treatments | Elicitation volume | Arachidin-1 (mg per flask) | | | Arachidin-3 (mg per flask) | | |
|---|---|---|---|---|---|---|---|
| | | 48 h | 72 h | 168 h | 48 h | 72 h | 168 h |
| 100 μM MeJA | 50 mL | ND* | ND | -* | 0.00021 ± 0.00036 | ND | - |
| 100 μM MeJA, 9 g/L CD | 50 mL | 0.46 ± 0.50 | 1.55 ± 0.41 | - | 3.73 ± 0.86 | 7.01 ± 1.38 | - |
| 125 μM MeJA, 18 g/L CD, 3 mM H₂O₂ and 1 mM MgCl₂ | 50 mL | 3.97 ± 1.02 | 9.28 ± 3.30 | 12.23 ± 1.84 | 7.36 ± 3.13 | 11.64 ± 5.82 | 15.22 ± 6.93 |
| 125 mM H₂O₂ and 1 mM MgCl₂, 18 g/L CD | 100 mL | - | 11.20 ± 1.74 | 22.74 ± 1.28 | - | 19.85 ± 3.93 | 37.06 ± 5.04 |

ND: Not detected; -: No data available.

Figure 46

METHOD TO INCREASE THE YIELD OF PRODUCTS IN PLANT MATERIAL

CROSS-REFERENCE TO RELATED APPLICATIONS

This application claims priority to and is a continuation in part of U.S. patent application Ser. No. 13/784,877 filed Mar. 5, 2013 which claims priority to previously filed and U.S. Patent Application No. 61/729,659, filed Nov. 26, 2012, the contents of which are incorporated herein by reference.

STATEMENT REGARDING FEDERALLY SPONSORED RESEARCH OR DEVELOPMENT

This invention was made with Government support from the National Science Foundation-EPSCoR (grant # EPS-0701890) and the US Department of Agriculture (award #2011-38821-30928). The Government has certain rights in the invention.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

Plant products including specialized metabolites (also referred to as plant secondary metabolites or plant natural products) have important applications as dietary supplements, cosmeceuticals, pharmaceuticals and agrochemicals. The term natural product refers to chemical compounds produced by a living organism. In an embodiment such compounds are small molecules. In many instances, due to the complexity of their chemical structures, the production of these products is not feasible via organic synthesis and therefore their availability depends on extraction from plant sources. In vitro plant cultures are recognized as sustainable bioproduction platforms for plant products. Indeed, high value pharmaceuticals such as taxol and ginsenosides are produced at industrial scale via cell suspension and root cultures, respectively. Efforts to increase the levels of plant products in plant cultures have been attempted by elicitation and metabolic engineering strategies. Elicitation approaches have only led to partial increases in yield particularly because of transcriptional and post-transcriptional regulatory mechanisms, such as feedback inhibition, that limit their accumulation in the plant. In many cases, these regulatory mechanisms are used by the plant to prevent their accumulation to toxic levels. Furthermore, metabolic engineering efforts have been restrained because many of the enzymes involved in the biosynthesis of high value products are currently unknown.

SUMMARY OF THE INVENTION

A process is provided for increasing the amount of a product of interest in plants and plant parts and cells. A precursor of the product of interest is contacted with the plant or plant part, which may optionally include an elicitor of the product of interest. The process further provides in an embodiment for a trapping agent to prevent feedback inhibition. A process is further provided for producing derivatives by use of the precursor which may include an elicitor and/or trapping agent. Carbohydrates including glucose and glucuronic acid in an embodiment may be added by the plant material to produce a derivative of the precursor. In a still further embodiment the plant cells are hairy root tissue, in another embodiment are root cultures and in a still further embodiment are cell suspension cultures.

Compared to a single elicitor, co-treatment of methyl jasmonate (MeJA) and cyclodextrin (CD) led a substantial increase on arachidin-1 and arachidin-3 accumulation in the medium of peanut hairy root culture. However, elicitation conditions with more than two elicitors have not been tested. To optimize the elicitation medium for maximum yield of prenylated stilbenoids, especially arachidin-1 and arachidin-3, the elicitation medium created from MeJA, a common signaling compound that mediates the induction the biosynthesis of stilbenoids, CD having capacity of trapping stilbenoids to potentially prevent feedback inhibition and $H_2O_2$ which induces piceatannol accumulation in peanut hairy root cultures as multiple elicitors for the elicitation medium (Yang et al., 2015). In addition, the concentration of magnesium ($Mg^{2+}$), a co-factor of resveratrol prenyltransferase(s) which is key enzyme involved in prenylated stilbenoid biosynthesis in peanut (Yang et al., 2016), was also optimized.

It is an object of the present invention to increase production of a product of interest from a plant.

It is also an object of the present invention to increase the production of a flavonoid from a plant.

It is also an object of the present invention to increase the production of a stilbenoid from a plant.

It is also an object of the present invention to increase the production of a prenylated stilbenoid from a plant.

It is also an object of the present invention to provide an elicitation medium to increase the production of a product of interest of a plant.

It is also an object of the present invention to increase the effectiveness of the elicitation medium that contacts the plant.

These and other objects and advantages of the present invention, along with features of novelty appurtenant thereto, will appear or become apparent by reviewing the following detailed description of the invention.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views:

FIG. 5 is a diagram in which the chemical structures of resveratrol and select resveratrol derivatives are shown.

FIG. 7A-C are graphs showing yield of arachidin-1 in control cultures (7A), in cultures treated with cyclodextrin and methyl jasmonate (MeJA) (7B), and in cultures treated with cyclodextrin, MeJA and piceatannol (7C).

FIG. 39 is a table view showing elicitation factors of one embodiment of the present invention.

FIG. 40 is a table view showing the results of one embodiment of the present invention.

FIG. 41 is a table view showing the results of one embodiment of the present invention.

FIG. 45 is a table view showing production of one embodiment of the present invention.

FIG. 46 is a table view showing arachidin-1 and arachidin-3 production of one embodiment of the present invention.

DETAILED DESCRIPTION

Figure 1:
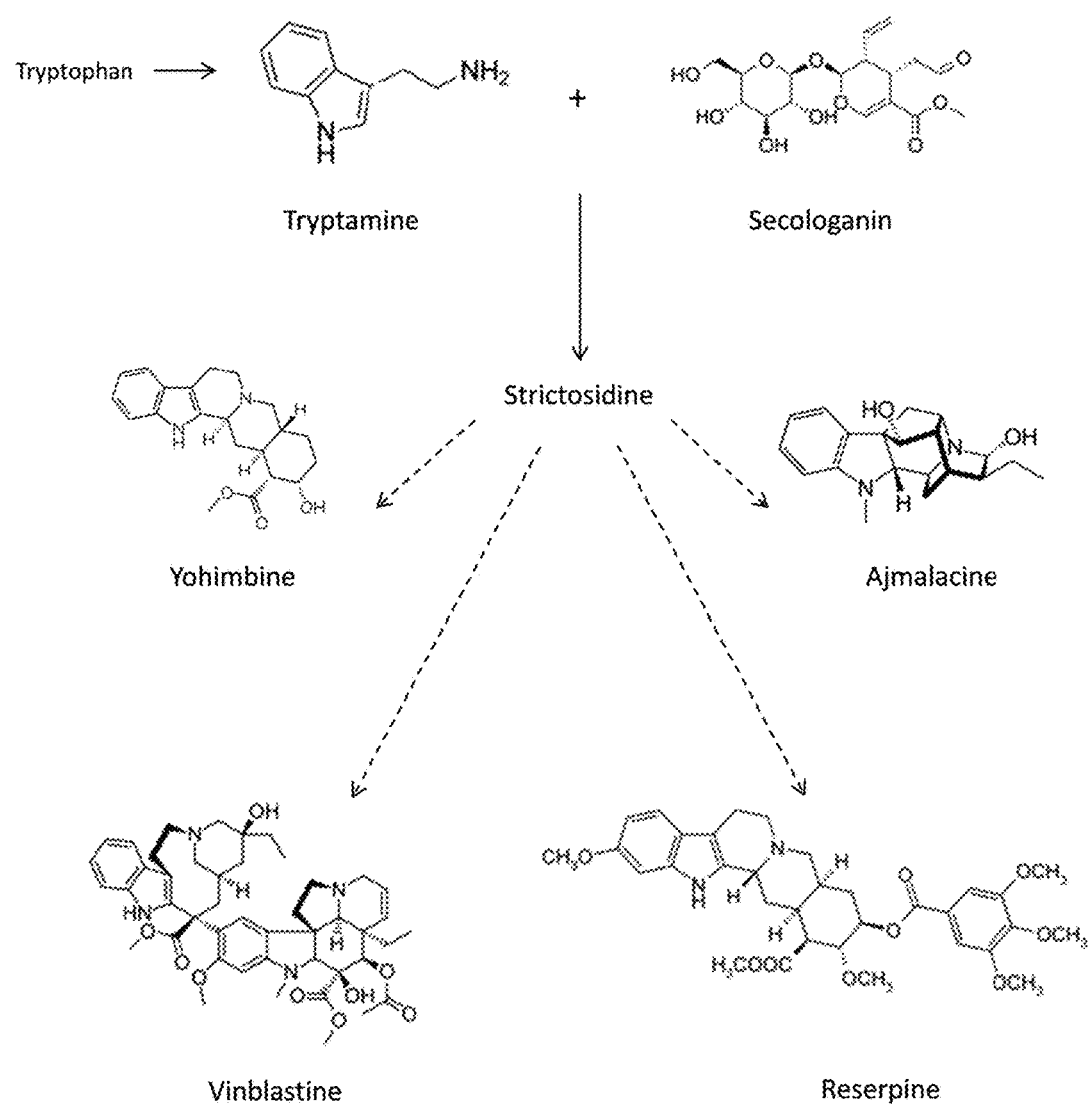
FIG. 1 is a flow chart showing an indole terpenoid alkaloid pathway.

This process addresses the problem of providing a method to produce high levels of one or more valuable products in a plant material. The solution provided by the invention is based on the addition of a putative precursor or xenobiotic to the plant culture which may also be combined with a trapping agent and also may be further combined with an elicitor.

The procedure could be applied to any plant material and is particularly useful for in vitro culture. The process is useful with plant material, including a plant, plant part, plant tissue, plant cultures, cell suspension culture or other plant material which can produce the product of interest. The term plant or plant material or plant part is used broadly herein to include any plant at any stage of development, or to part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered a plant cell for purposes of this disclosure. A plant tissue or plant organ can be a seed, protoplast, callus, or any other groups of plant cells that is organized into a structural or functional unit. In an embodiment hairy root cultures or root cultures may be used as the plant material, as discussed further below. It may be used with plant material from any plant species and to any class of product. An embodiment provides the product is produced as a result of enzymatic steps in the plant. A further embodiment provides the plant optionally may be transformed with a nucleic acid molecule that encodes an enzyme that converts a substrate to the desired product.

The process may be used with any plant that produces a product of interest whether monocotyledonous or dicotyledonous or gymnosperms, including but not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanut (*Arachis hypogaea*), carrot (*Daucus carota*) cotton (*Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (Musa spp.), avocado (*Persea americana*), fig (*Ficus* casica), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus* amygdalus), sugar beets (*Beta vulgaris*), oats (*Avena*), barley (*Hordeum*), radish (*Raphanus sativus*), soybean (*Glycine max*), strawberry (*Fragaria×ananassa* Duch.), vegetables, ornamentals, and conifers and medicinal and medicinally active plants including species such as hemp (*Cannabis sativa* L.), Indian mustard (*Brassica juncea* L.), *Salvia miltiorrhiza, Salvia austriaca, Withania somnifera, Pueraria candollei, Polygonum cuspidatum, Polygonum multiflorum, Scutellaria baicalensis, Scutellaria lateriflora, Scutellaria viscidula, Azadirachta indica, Panax ginseng, Anisodus acutangulus, Artemisia annua, Cassia obtusifolia, Phytolacca americana, Tephrosia purpurea,* licorice (*Glycyrrhiza glabra*), *Psammosilene tunicoides,* pomegranate (*Punica granatum*), *Peganum harmala, Sylibum marianum, Nicotiana benthamiana, Calotropis gigantean, Linum mucronatum, Linum album, Chenopodium murale, Catharanthus roseus,* black nightshade (*Solanum nigrum*), *Atropa belladonna, Rauvolfia verticillata, Panax quinquefolium, Aconitum coreanum, Coleus forskohlii,* red beet (*Beta vulgaris* L.), Egyptian henbane (*Hyoscyamus muticus*), *Arnebia euchroma* (Royle) Johnst, oriental melon (*Cucumis melo* L. cv. Geumssaragi-euncheon), muskmelon (*Cucumis melo* L.), *Latuca virosa, Sesamum indicum, Abelmoschus esculentus,* periwinkle (*Vinca minor* L.), pink periwinkle (*Catharanthus roseus* G. Don syn. *Vinca rosea* L.), *Eurycoma longifolia*, Tartary buckwheat (*Fagopyrum tataricum*), common buckwheat (*Fagopyrum esculentum* Moench), *Sapium sebiferum, Datura innoxia, Lithospermum canescens, Trigonella foenum,* devil's claw (*Harpagophytum procumbens*), *Angelica gigas, Plumbago zeylanica, Echinacea purpurea, Psammosilene tunicoides, Ocimum basilicum, Ophiorrhiza alata, Ophiorrhiza rugosa,* valerian (*Valeriana officinalis* L.), *Picrorhiza kurroa,* watercress (*Nasturtium officinale*), *Camptotheca acuminata, Pogostemon cablin, Taxus x media, Taxus* spp., annatto (*Bixa orellana*), *Veratrum calfornicum, Astragalus membranaceus, Rhodiola kirilowii, Calendula officinalis, Amebia euchroma, Papaver bracteatum, Linum narbonense, Lotus japonicas, Panax quinquefolium, Sinapis alba, Coleus blumei*.

Examples of plants that naturally produce a stilbene include *Pinus sibirica, Pinus sylvestris, Gnetum parviflorum, Vitis vinifera, Vitis rotundifolia, Polygonum cuspidatum, Arachis hypogaea, Eucaliptus* spp., *Artocarpus lakoocha, Nothofagusfusca, Phoenix dactilifera, Festuca versuta, Carex fedia, Veratrum grandiflorum, Cassia quinquangulata, Lycopersicon esculentum, Gossypium hirsutum* and any other plant species shown to produce resveratrol, pinosylvin or their derivatives or analogues.

As discussed further below, production of any product of interest may be enhanced using the process. Compounds in this category of products include but are not limited to phenolics, terpenoids and alkaloids. These compounds could be either produced constitutively by the plant, produced at basal levels and their biosynthesis induced by an elicitor or induced de novo upon elicitor treatment.

A product of interest or target compound produced by a plant is identified. The product of interest or target compound may be any product, including an intermediate of a desired product, produced by a plant having commercial usefulness. It may be a compound in one embodiment that the plant produces in the presence of an eliciting substance, and in another embodiment is one produced in the absence of an eliciting substance. In an embodiment one may select a commercially useful product that is not made synthetically, or produced synthetically but at a higher cost than when produced by the plant. Examples of such products of interest without limitation are the major groups of compounds produced by plants, the phenolics, alkaloids and terpenoids. The family of compounds are related structurally and regulated by plant machinery. By way of further example without limitation, the terpenoids include diterpenes (such as taxol produced by yew plants), saponins (such as ginsenosides produced by *Panax ginseng*), sesquiterpenes (such as artemisinin produced by *Artermisia annua*). Examples, without intending to be limiting of phenolics include stilbenoids (such as arachidin-1 produced by peanut) and flavonoids (such as wogonin produced by *Scutellaria*). Examples without intending to be limiting of alkaloids include monoindole alkaloids (such as vinblastine produced by *Catharanthus roseus*), steroidal alkaloids (such as cyclopamine produced by *Veratrum californicum*), tropane alkaloids (such as hyoscyamine produced by *Hyoscyamus muticus*). In one embodiment, the processes described are particularly useful in the production of stilbenoids. A discussion of the stilbenoid compounds which can be produced by plants is provided below.

As a result of employing a precursor which may also include a trapping agent, and, where needed, an elicitor, the amount of the product of interest can be increased at least ten times, at least 20 times, 30 times, 40 times, 50 times, 60 times, 70 times, 80 times, 100 times, 1000 times, 2000 times, 3000 times, 4000 times, 5000 times, 10,000 times, 250,000 times and more and amounts in-between as compared to those cultures which did not include at least a precursor, and which optionally included an elicitor and/or trapping agent as well. In one embodiment, the product of interest, such as arachidin, is increased at least 250,000 times.

Further, the inventors have discovered new compounds of commercial and medical value which can be produced using an elicitor, trapping agent and precursor. The process can produce as a product of interest, valuable derivatives of a compound. These derivatives are compounds obtained from another compound. In an embodiment, the original compound can be transformed into a product of similar chemical structure. An embodiment provides production of valuable derivatives of the precursor. By way of example, a carbohydrate such as glucose or glucuronic acid is added to the precursor. By way of example without limitation, such a combination can be used to add a carbohydrate to produce a glucoside or glucuronide of the precursor. Most plants when exposed to a xenobiotic compound, a foreign chemical such as a drug, or putative precursor will add glucose to the xenobiotic compound and store it but glucuronic acid derivatives are found in animals but rarely in plants. However, here, it was possible to add glucuronic acid to the precursor to produce a glucuronide. Glucuronidation is an important biochemical process for drug metabolism in humans and to date there are no efficient means of producing these compounds. Here, with use of an elicitor, precursor and trapping agent, it is possible to produce glucuronides. Further enhancement of production of glucuronides is possible by seeding the medium with glucuronic acid.

The precursor can be involved in the biosynthesis of the targeted compound/product of interest. When such precursor is a xenobiotic it may be any foreign compound (not produced in the plant culture) that could be biotransformed into an intermediate or product of the biosynthetic pathway of the targeted compound. Having identified the target compound, potential precursors may be identified which have a similar structure and/or are in the pathway that leads to production of the product. A similar compound, for example, may be the same chemical backbone structure, but have an additional chemical group that is modified or removed to produce the product. In an example, the compound may have a hydroxyl group attached, where the product lacks the hydroxyl group, it having been removed by a reaction in the plant. The putative precursor may then be tested to determine if it provides the enhanced production described here. When examining the pathway that leads to production of the product of interest, in an embodiment one identifies putative precursors that are closer in the pathway to the product as opposed to early in the pathway. Those compounds early in the pathway could be converted to a compound different from the desired product of interest. By way of example without limitation, if a compound is ten or twenty steps earlier in the pathway than the product of interest, it may be too early in the pathway to be a useful precursor. Those compounds, by way of example without limitation, that are one step, two steps, three steps, four steps or five steps in the pathway are useful putative precursors. Testing may then confirm its usefulness as precursors. Examples of precursors of terpenoids are acetate, acetyl-CoA, isopentenyl pyrophosphate, pyruvate, glyceraldehyde-3-phosphate, dimethylallyl diphosphate, geranyl diphosphate, farnesyl diphosphate, squalene and phytoene; examples of precursors of phenolics include phenylalanine, tyrosine, coumaric acid, coumaroyl-CoA, caffeic acid, caffeoyl-CoA, cinnamic acid, cinnamoyl-CoA, ferulic acid, feruloyl-CoA, and naringenin and malonyl-CoA; examples of precursors of alkaloids include tryptophan, phenylalanine, tryptamine, secologanin, stricosidine, tyrosine, tyramine, dopamine, reticuline, and putrescine. Precursors can be added one or more times before, after or together with trapping agent and elicitor.

Figure 2:
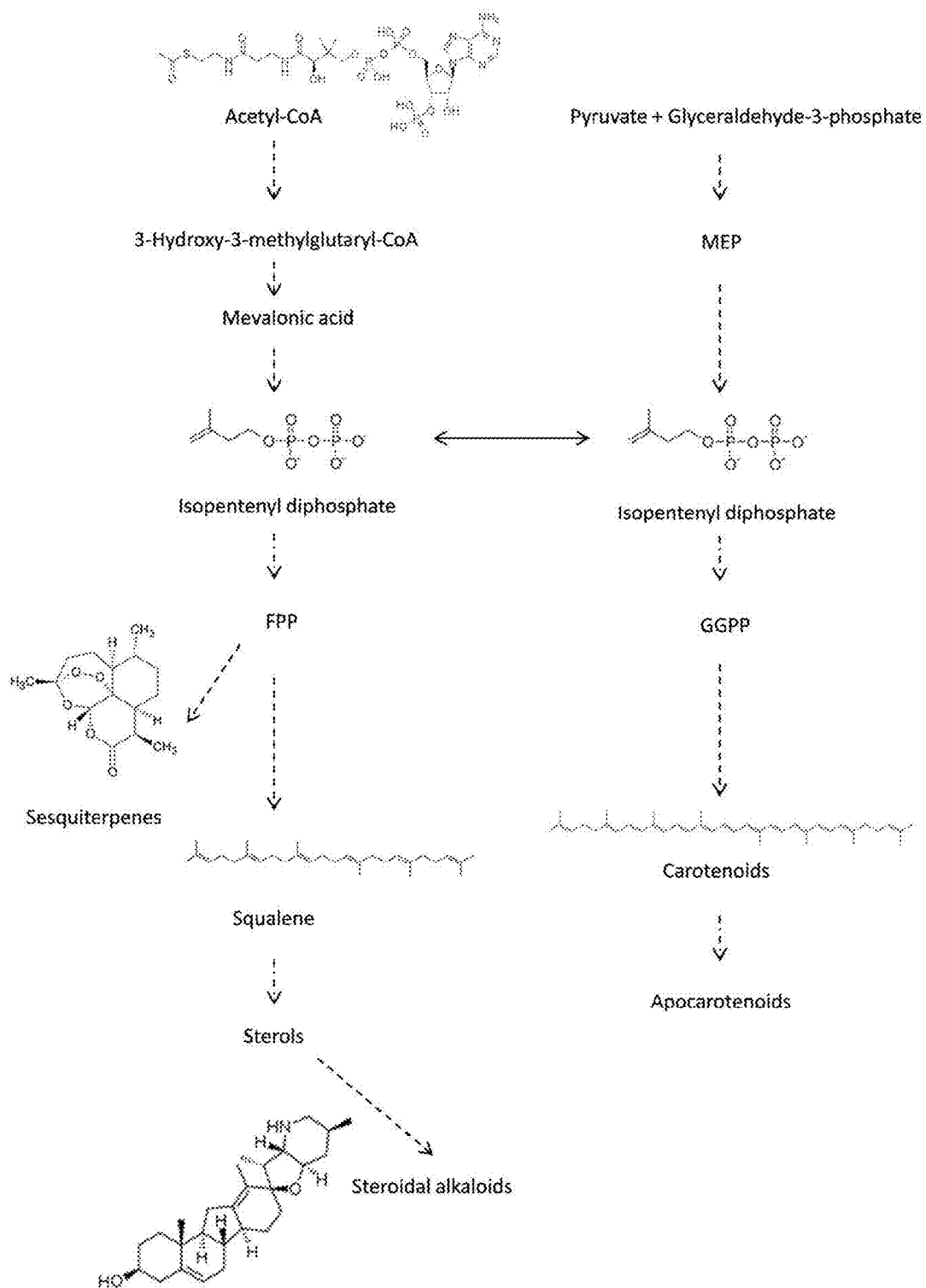
FIG. 2 is a flow chart showing a terpenoid and steroidal alkaloid pathway.
Figure 3:
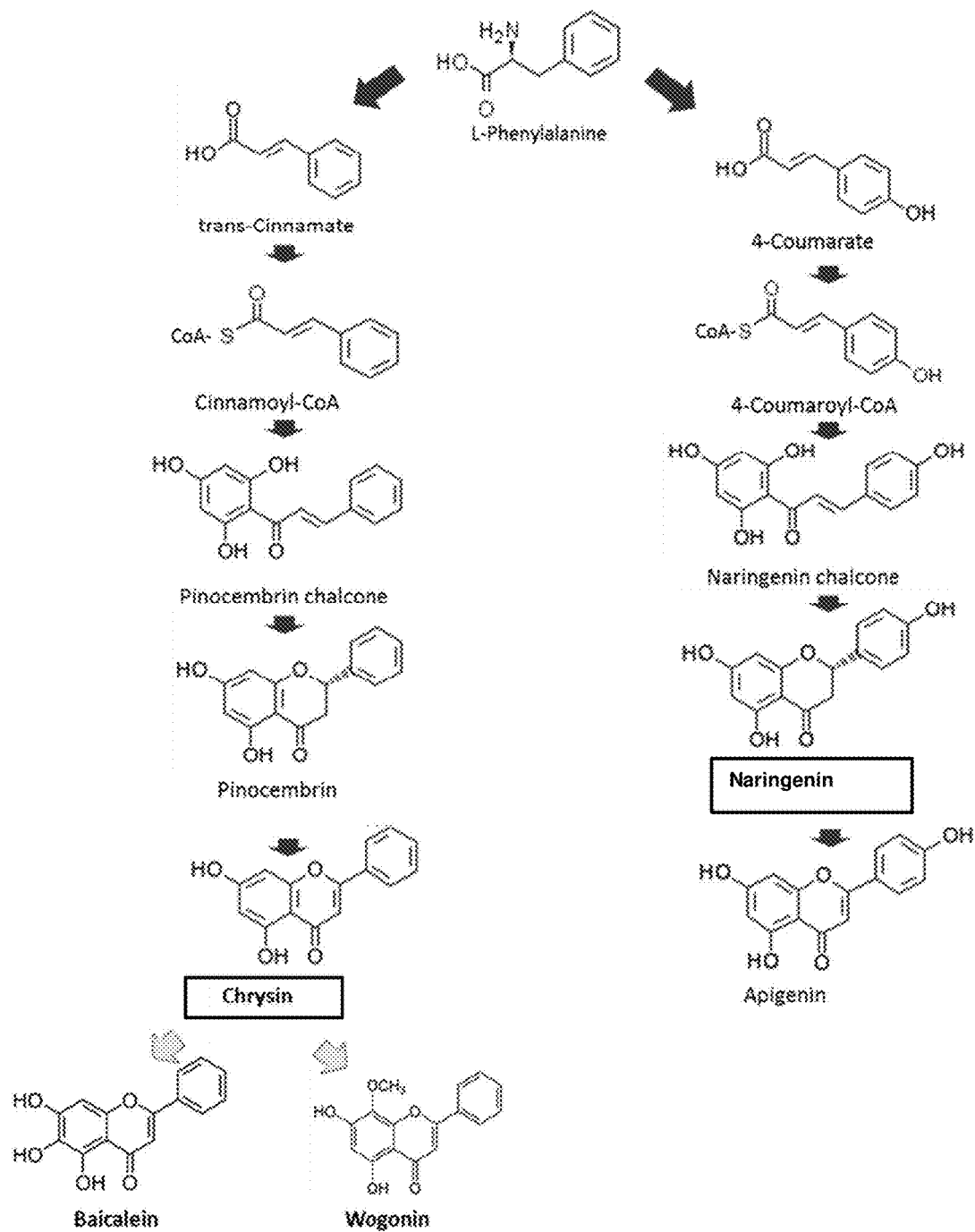
FIG. 3 is a flow chart demonstrating biosynthesis of flavonoids.

FIG. 1 shows by way of example portions of an indole terpenoid alkaloid pathway and FIG. 2 shows by way of example portions of the terpenoid and steroidal alkaloid pathways. FIG. 3 shows by way of example biosynthesis of flavonoids. Compounds indicated with a box were selected as metabolic precursors for feeding experiments in combination with cyclodextrin and methyl jasmonate.

Here it has been discovered that using at least one such precursor dramatically increases the amount of product of interest produced in the plant. Using a precursor can result in feedback inhibition of production of the product of interest. With the combination of a trapping agent disclosed here, such feedback inhibition has not limited production of the product.

In an embodiment, the ability of the precursor to substantially increase the amount of product of interest is enhanced where a trapping agent is used to aid in preventing feedback inhibition. A trapping or binding agent is one that can complex with compounds in the pathway and trap the product or intermediate. In a preferred embodiment the trapping agent is one which is not permanently bound to the product of interest.

An example of one such trapping agent, without intending to be limiting, is cyclodextrin. This family of compounds are cyclic sugars that are the result of enzyme decomposition of starch and typically have toroidal structures formed by 6 to 8 (or up to 10) glucose residues. Examples include α-, β- and γ-cyclodextrins. Cyclodextrins have been well characterized, as, for example, published by the National Office for Research and Technology providing a database at www.cyclodextrin.net and such publications as Szejli (1998) "Introduction and general overview of cyclodextrin chemistry" Chem Rev. 98(5):1743-1754; Loftsoon et al. (2007) "Cyclodextrins and their pharmaceutical applications" Int. J. Pharm. 329(1-1): 1-11. Cyclodextrin has been used to elicit resveratrol in cell cultures (See U.S. Pat. No. 7,309,591). Without intending to be bound by a particular theory, it is believed in the present process, the cyclodextrin acts not just as an elicitor, but to prevent feedback inhibition of production of a product of interest. This soluble compound has advantage in that it is not permanently bound to the product of interest and is believed to act to prevent inhibition of the enzyme producing the downstream product, thereby allowing continuation of the biosynthetic pathway. Different types of cyclodextrin, including □-cyclodextrin, are known to make complexes with hydrophobic compounds thereby increasing their solubility. The complex of the putative precursor or xenobiotic with cyclodextrin could increase their solubility. In addition, cyclodextrins may trap toxic intermediates in the pathway or trap the desirable product thereby preventing feedback inhibition of the pathway.

Where the product or a precursor is hydrophobic, hydrophobic resin may be used. The hydrophobic resin may also serve as a trapping agent for products of interest. An example, without intending to be limiting, of such a resin is a polystyrene resin, such as DIAION HP-20 polystyrene resin manufactured by Supelco (Bellefonte, Pa.). This resin was described in Abbot and Medina-Bolivar et al. (2010) "Purification of resveratrol, arachidin-1 and arachidin-3 from hairy root cultures of peanut (*Arachis hypogeaea*) and determination of their antioxidant activity and cytotoxicity" American Institute of Chemical Engineers, DOI 10/1002/btpr.454, published online Jul. 7, 2010 in Wiley Online Library (wileyonlinelibrary.com). There, the resin was used to extract the stilbenoids. The resin absorbed the stilbenoids which were then extracted from the resin with ethyl acetate. Another example that could be used in tissue cultures is the hydrophobic polymeric resin X-5 which resin is described by Yan et al. (2005) in "Efficient production and recovery of diterpenoid tanshinones in *Salvia miltiorrhiza* hairy root cultures with in situ adsorption, elicitation and semi-continuous operation".

Common elicitors used in the plant cultures are jasmonic acid and its derivative methyl jasmonate. These elicitors act as signal molecules to upregulate specialized biosynthetic pathways. There are many such elicitors known to one skilled in the art and which will become available to one skilled in the art. Examples of such elicitors, without intending to be limiting, are discussed below.

Different incubation periods of the putative precursor or xenobiotic which may include the trapping agent and elicitor may be tested to obtain different levels of the targeted product. In one example, the trapping agent is combined with the elicitor for different periods. In another example, the precursor is combined with the trapping agent and elicitor for different periods. The periods could be from any number of hours to any number of days. After the incubation period the culture medium and tissue are removed and analyzed for the desired products. In one example, the culture medium is removed after the incubation period and the culture is re-induced with fresh medium containing the elicitor with the trapping agent which may also include the putative precursor or xenobiotic. The re-induction process is then repeated for any number of times.

Furthermore, cultures at different stages of development may respond differently to the treatment of the trapping agent, putative precursor or xenobiotic and elicitor. The conductivity of the culture medium could be used as an estimation of the stage of development of the plant culture. Therefore, highest production levels in response to the treatment of the trapping agent, putative precursor or xenobiotic and elicitor will depend on conducting the experiment at a particular range of conductivity values of the culture medium. An embodiment provides that for highest levels of product production, a preferred stage of growth of the plant culture is used. One may test for the preferred stage by assessing the impact of different stages of growth of the culture. Any means for measuring stage of growth of a culture may be used that is convenient. By way of example without limitation, one means of measuring the stage of hairy root culture growth is to measure conductivity. Conductivity can be measured by any convenient methods, and one example is to use a SevenEasy™ conductivity meter (Mettler Toledo). There is an inverse relationship of conductivity to growth of the culture. At the stationary phase, no change in conductivity is observed. Conductivity measures the total ionic composition change in the medium. See Condori et al. (2010) "Induced biosynthesis of resveratrol and the prenylated stilbenoids arachidin-1 and arachidin-3 in hairy root cultures of peanut: Effects of culture medium and growth stage" *Plant Physiology and Biochemistry* 48:310-318; Yang et al. (2005) "Conductivity and pH dual detection of growth profile of healthy and stressed *Listeria monocytogenes.*" *Biotechnol. Bioeng.* 92:685-694. $H^+$ and other ions may be measured. As the culture takes up nutrients, conductivity decreases. The optimal stage of culture may be an early stage, or later stage depending upon the enzymes that are developmentally expressed. In one example, the optimal stage is the mid-exponential growth stage. In an example without intending to be limiting, Condori et al (2010), supra, measure the impact of elicitation of stilbenoids at varying growth stages of days 6, 9, 12, and 15. While varying stages produce the desired stilbenoids, trans-resveratrol, trans-arachidin-1 and trans-arachidin-3, it was found that using MSV medium produced higher levels of trans-resveratrol at all culture ages, and there was more variability in levels of trans-arachidin-1 and trans-arachidin-3 compared to resveratrol in either B5 or MSV medium. For the highest production of stilbenoids in peanut Hull3 line, use of MSV medium at day 9 resulted in the highest levels. The use of plant hairy root cultures and root cultures to produce stilbenes is discussed at length in U.S. Pat. No. 7,666,677, incorporated by reference herein in its entirety, and also at US Publication No. 20100130623, also incorporated by reference herein in its entirety.

Stilbenes, including resveratrol and pinosylvin, have garnered much interest over the past few decades due to various health benefits associated with these plant secondary metabolites. Resveratrol is a popular, natural antioxidant molecule associated with cardiovascular and anticancer health benefits. Resveratrol exists as both the trans- and cis-isomer with numerous reports suggesting trans-resveratrol to be the most bioactive form of this molecule (Roupe et al., 2006a). Trans-resveratrol can readily be converted to cis-resveratrol when exposed to UV light and is unstable when exposed to high pH conditions. In addition to the resveratrol isomers, derivatives of resveratrol that include but are not limited to glucosylated, prenylated, methylated, hydoxylated modifications as well as tetramers of resveratrol have been linked with beneficial activities. Several of these forms of resveratrol may in fact provide enhanced bioavailability and performance profiles surpassing that observed for the free resveratrol isomers (Chang et al., 2006; Roupe et al., 2006b; Wenzel and Somoza, 2005; Soleas et al., 2001). Some examples include naturally occurring monomethylether analogues of resveratrol that may be important in the inhibition of CYP1A2 and CYP2E1's potential chemopreventive activity (Mikstacka et al., 2006). Several novel and previously identified resveratrol derivatives including several vitisinols, vineferal and ε-viniferin from the roots of *Vitis thunbergii* showed significant antioxidative and antiplatelet activities (Huang et al., 2005). Recent identification of a tetrameric form of resveratrol, vaticanol B, appears to have potent anti-inflammmatory properties in protecting cells against ER stress-induced cell death (Tabata et al., 2007). Arachidin-1 and -3 are prenylated derivatives of resveratrol found in peanuts and show favorable anti-inflammatory and antioxidant activities in a cell model (Chang et al., 2006). Likewise, pinosylvin and its derivatives have shown promise as anti-inflammatory and chemopreventative agents (Park et al., 2004; Lee et al., 2006). The above lists a few examples and many other derivatives are known or remained to be identified and included within the scope of the invention. While resveratrol, pinosylvin, and their respective derivatives can be recovered as an extract from a variety of plants, these products sourced from raw botanical material may not be suitable for all applications in the food/pharmaceutical sectors due to endogenous plant impurities/associated color (i.e. phenolic compounds, tannins, etc.) or production impurities (i.e. chemical residues, heavy metals, soil pathogens). In addition, these secondary metabolites are generally recovered from the raw botanical material at relatively low concentrations. Finally, stilbene yields can be highly variable from lot to lot of this raw botanical material due to the impact of environmental factors in the field.

In the '677 patent and in US publication 201030623, it was shown that plant hairy roots, produced via infection with *Agrobacterium*, offer a novel and sustainable plant tissue-based system for the bioproduction of valued secondary metabolites including the stilbenoids resveratrol, pinosylvin and their respective derivatives. These roots reflect the metabolic phenotype of the host plant, yet are unique in their genetic and biosynthetic stability, providing advantages in production sustainability when compared with plant cell culture systems. Recent progress in the scale-up of hairy root cultures, such as the use of a low cost mist bioreactor for commercial production of the anticancer camptothecin, continues to advance this system as an attractive tool for industrial processes (Wink et al., 2005; Guillon et al., 2006). Further, production of increased amounts of the trans-isomer of resveratrol as well as other valued stilbene derivatives in medium and root has been demonstrated through hairy root elicitation of this plant tissue culture platform.

Figure 4:
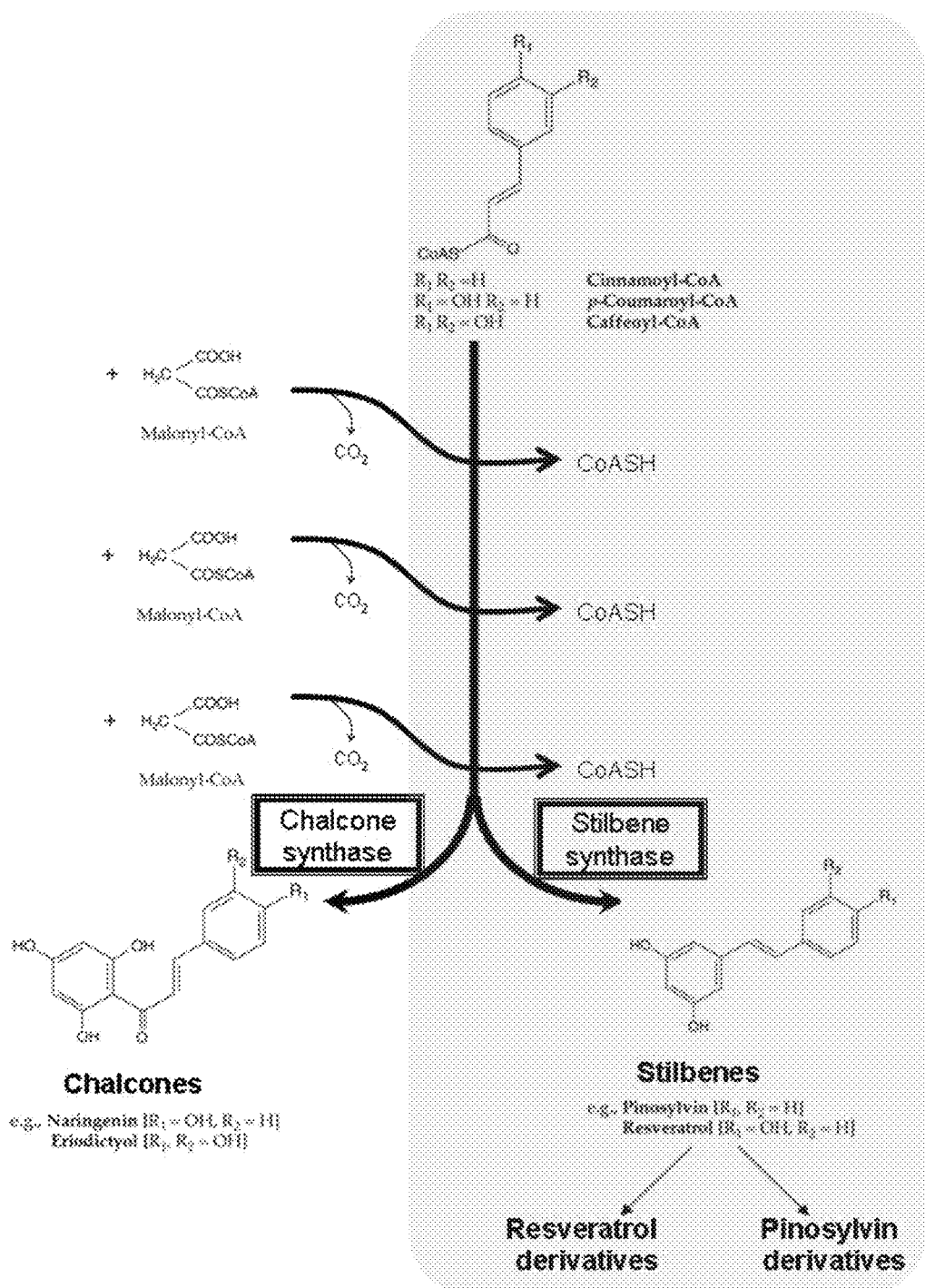
FIG. 4 is a flow chart showing a biosynthetic pathway of stilbenes, including resveratrol derivatives and pinosylvin and derivatives.

The following abbreviations are used here: B5, Gamborg's B5 medium with 2% sucrose (Gamborg et al., 1968); cv., cultivar; HPTLC, high performance thin layer chromatography; HPLC, high performance liquid chromatography; Rf, retardation factor; Rt, retention time; TLC, thin layer chromatography With establishment of hairy root cultures from a wide variety of selected plant species, the 'publication and patent showed that stilbenes, including resveratrol, pinosylvin and their respective derivatives can be produced without inclusion of a transgene encoding key enzymes (such as those encoding resveratrol synthase, the enzyme involved in the synthesis of resveratrol; Chun et al., 2001). These stilbenes have been reported to be produced naturally in a wide range of plant species (Aggarwal et al., 2004). What is more, hairy root cultures can also be used with plants transformed with genes encoding a stilbene synthase enzyme. Stilbenes are naturally occurring defense compounds derived from the activity of a stilbene synthase (i.e. resveratrol synthase or pinosylvin synthase). A stilbene synthase enzyme defines an important regulatory entry point to the stilbene biosynthetic pathway as shown in FIG. 4. By use of the term stilbene or stilbene composition is meant: (i) resveratrol and/or all natural resveratrol derivatives and analogues, including, for example, those shown in FIG. 5 and any other identified as derivatives of resveratrol and (ii) pinosylvin and/or all natural pinosylvin derivatives and analogues.

Since these stilbene derivatives are typically present and recoverable in only small amounts from field-grown raw botanical material, the hairy root production platform offers a viable, saleable, production alternative for naturally sourced resveratrol, resveratrol derivatives and other valued stilbenes. When referring to a resveratrol composition is meant to include resveratrol, resveratrol derivatives or combinations of same. Likewise, when referring to a pinosylvin composition is meant pinosylvin, pinosylvin derivatives, and combinations of same.

Hairy root disease was first identified as a problem in select plants caused by *Agrobacterium rhizogenes*, which can be isolated from the soil. The gram-negative bacterium transfers DNA from its root-inducing (Ri) plasmid into the genome of the infected plant cell which results in the formation of roots. Its use in the control of beneficial growth of roots was described by Strobel, U.S. Pat. No. 4,588,693. In the production of hairy root cultures, the plant is infected with the *Agrobacterium* by exposure of plant cells or plant parts to *Agrobacterium*. For example, the rol genes containing genes rolA, rolB and rolC (F. F. White et al., (1985)) are present in the T-DNA of *Agrobacterium rhizogenes* Ri plasmid and expression of these genes induce the formation of hairy roots. Any plant part, tissue or cell capable of producing hairy roots can be used. Such plant parts can include, for example and without limitation, plant stem, petiole, cotyledonary node, hypocotyl, or other plant parts or cells. A semi-solid medium or liquid nutrient solution is preferably employed which is optimized for maintenance of roots, resulting in increased growth rate of roots compared to non-infected plant cells. While many types of material and solutions and medium are known and can be used in the invention, several preferred examples include Murashige and Skoog and Gamborg B5 medium. Several media modifications optimized for meeting in vitro nutrient requirements of different host plants used in making sustainable hairy root cultures can be employed.

Further, the patent and publication show vectors for producing hairy roots in plants, which contain both the rol genes and aux genes in a single transfer DNA (T-DNA). This vector allows sustained growth of the hairy root line without the use of auxins since both rol and aux genes are inserted in the same plant cell DNA. Screening for several lines of hairy roots results in identification of a line that can sustain growth in liquid after several subculturing events on semi-solid medium. A vector with both rol and aux genes reduces the time in obtaining stable high growth/stilbene-secreting hairy roots. Such vectors can be used in *A. tumefaciens*, such as strains EHA105 and LBA4404 or *A. rhizogenes* strains such as R1000 and ATCC 15834.

The hairy roots are then exposed to an elicitory substance to produce the stilbenoid compounds including resveratrol, pinosylvin, and associated derivatives of these molecules. A vast number of elicitors are known to one skilled in the art, as set forth, for example, at Raskin, US publication no. 20020132021. Among elicitors known to be effective in eliciting resveratrol are the cyclodextrins, including randomly methylated β-cyclodextrin, cellulase, laminarin, chitosan, sodium acetate, copper sulfate, ultraviolet light, jasmonates, sodium orthovanadate (Rudolf and Resurreccion, 2005; Tassoni et al., 2005; Bru et al., 2006). While certain elicitors may produce optimum results, the person skilled in the art will appreciate that a number of different elicitors are available for use in the invention.

Resveratrol, pinosylvin, and derivatives may be obtained from the roots, medium or solution and extracted by known procedures, and the invention is not limited by any particular extraction procedure. For example, column chromatography, crystallization, distillation, liquid or solid phase extraction are among many techniques known in the art. An example of one such process is use of a solvent which can create two phases capable of separation, such as ethyl acetate. This provides advantages over use of solvents such as methanol, where drying is required because methanol and water are miscible and two phases are not produced. However, since the media used may be rich in sugars these can bind some of the stilbenoids, resveratrol and pinosylvin, causing a drastic decrease in recovery.

Further, the inventors have discovered that root cultures can be used to produce stilbenoids, and are effective in producing increased amounts of derivatives. The term root cultures herein is referring to a root culture other than hairy root cultures, and are those which do not require infection with *Agrobacterium* nor require introduction of an Agrobacteria gene(s) as with production of hairy root cultures. Root cultures which can be used to produce stilbenes or other compounds are a proliferating root culture system derived from root tips of apical or lateral origin grown under sterile (in vitro) or non-sterile conditions that do not require infection with *Agrobacterium*. The root tips or biomass are derived from roots of seedlings, plantlets, hydroponically-grown plants or any plant explant or callus induced to produce roots. Production of stilbene or other target composition can be increased in an embodiment by increasing production of the root cultures, exposing the culture to chemical or physical stimulus or by genetic modification of the roots. The stilbene composition may be in a further embodiment isolated from roots or root culture media and in an embodiment may be purified by known processes such as chromatography and chemical solvent extraction, for example. In one embodiment, in order to increase root biomass, in vitro isolated root cultures (adventitious root cultures) are supplemented with exogenous auxin hormone(s) [e.g. indole acetic acid (IAA), naphthalene acetic acid (NAA), indole butyric acid (IBA), 2,4-dichlorophenoxyacetic acid (2,4-D)]. Alternatively hormones are provided directly from the system in the case of root cultures derived from hydroponically-grown plants. In such root cultures the root biomass may likewise be produced in batch cultures and/or bioreactors as described herein.

Thus, as discussed above, stilbene is produced, stilbene having a common backbone structure consisting of a hydrocarbon with a trans or cis ethane double bond substituted with a phenyl group on both the carbon atoms of the double bond. Such stilbene derivatives include precursors and analogs and, for example, but without limitation, include glycosylated, prenylated, methylated and hydoxylated modifications as well as oligomers and polymers of same. Further specific examples, without meant to be limiting, include trans- and cis-resveratrol, piceid, arachidin including arachidin-1 and 3, vitisinols, viniferal and ε-viniferin, vaticanol B, pinosylvin derivatives, among others. Increased production of valuable derivatives provides for an enhanced activity of such stilbene compositions. Compositions having increased stilbene derivatives compared to resveratrol have particular advantages and medical and health enhancing benefits. Benefits are particularly useful where the amount of derivative produced in the composition compared to resveratrol is at least ten times as much, at least 20 times as much, at least 30 times as much, at least 40 times as much, at least 50 times as much, at least 100 times as much, at least 1000 times at much and any amount in between.

Assay and analysis of resveratrol may be conducted through any variety of methods, and can include, for example, taking advantage of natural fluorescence of the compound when exposed to ultraviolet light. Thin layer chromatography, high performance thin layer chromatography (Babu et al., 2005), high performance liquid chromatography, and gas chromatography-mass spectrometry are among the examples of assays that may be used to assay the resveratrol produced.

Reference to plants includes whole plants as well as plant cells and plant parts such as tissues, or protoplasts from the plant or organism, cell cultures, tissue cultures, calli, embryos, and seeds. Plants that are particularly useful are those naturally producing resveratrol, which include *Pinus sibirica, Pinus sylvestris, Gnetum parviflorum, Vitis vinifera, Vitis rotundifolia, Polygonum cuspidatum, Arachis hypogaea, Eucaliptus* sp., *Artocarpus lakoocha, Nothofagus fusca, Phoenix dactilifera, Festuca versuta, Carex fedia, Veratrum grandiflorum, Cassia quinquangulata, Lycopersicon esculentum, Gossypium hirsutum* and any other plant species shown to produce resveratrol. In a preferred embodiment of the invention the plant is *Arachis hypogaea*. In another preferred embodiment the plant is *Vitis rotundifolia*. In another preferred embodiment the plant is *Polygonum cuspidatum*. In another preferred embodiment stilbenes are produced from non-transgenic *Nicotiana*, such as *Nicotiana benthamiana*.

As described in the patent and publication, one may also employ in the process a plant which does not naturally produce stilbenes including resveratrol and pinosylvin, but which has been genetically engineered so that it produces stilbenes. As discussed herein, any plant that can be genetically engineered could be transformed with a nucleotide sequence expressing a stilbene synthase (i.e. resveratrol synthase or pinosylvin synthase). In an additional embodiment, a plant may be genetically engineered to co-express a stilbene synthase (i.e. resveratrol synthase or pinosylvin synthase) with one or more genes involved in the production of a resveratrol or pinosylvin derivative. For example, Hall and De Luca (2001) cloned a glucosyl transferase from Concord grape (*Vitis labrusca*) that can use resveratrol as substrate. In one example, co-expression of resveratrol synthase and this resveratrol glucosyl transferase can lead to the production of resveratrol glucosides. Hall and De Luca also show that resveratrol glucosyl transferase can use different phenolic compounds as substrates. Because many of the enzymes catalyzing the downstream modifications of resveratrol or pinosylvin may also accept different phenolic compounds as substrates, one may predict that other enzymes that also use as substrates other phenolic compounds may also accept resveratrol or pinosylvin and produce resveratrol or pinosylvin derivatives. These enzymes are not limited to glucosyl transferases, prenyltransferases, methyltransferases and hydroxylases. Specific examples of these enzymes are flavonoid-O-methyltransferases, caffeoyl-CoA methyltransferase, cinnamoyl-CoA methyltransferase, geranyltransferase and any other enzyme that could accept a stilbenes compound as substrate. Using general plant transformation methods, genes encoding these enzymes could be co-expressed with a stilbene synthase or express in a transgenic plant already expressing a stilbene synthase. In addition, plants naturally producing stilbenes can be engineered with an enzyme to produce a specific class of derivative and hairy roots can be produced from these engineered plants.

Plants transformed with a gene encoding a stilbene synthase, for example resveratrol synthase or pinosylvin synthase, include any plant capable of being so transformed, including, without limitation, plants that may be used for food and feed, such as corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), potato (*Solanum tuberosum*); and peas (*Lathyrus* spp.). Alternatively, the transgenic plant may be a species that is not conventionally eaten, such as tobacco (*Nicotiana tabacum*), tea (*Camellia sinensis*), flax (*Linum*), sisal (*Agave sisalana*), firs, and cedars. Production of transgenic plants with a nucleotide sequence encoding resveratrol synthase is known, such as that discussed at Paiva et al., U.S. Pat. No. 6,974,895 and Chia et al. US publication no. 20040111760. The resulting transgenic plant or plant cell can then be induced to produce hairy roots using the process of the invention, and resveratrol or other stilbenoids could be recovered. Further, one appreciates that it falls within the scope of the invention to introduce into plant cells other desirable nucleotide sequences and then produce hairy roots from the plant cells, whether the plant naturally produces resveratrol, pinosylvin or related derivatives or is genetically engineered to produce these secondary metabolites.

In general, the methods available for construction of recombinant genes, optionally comprising various modifications for improved expression, can differ in detail. However, conventionally employed methods include PCR amplification, or the designing and synthesis of overlapping, complementary synthetic oligonucleotides, which are annealed and ligated together to yield a gene with convenient restriction sites for cloning, or subcloning from another already cloned source, or cloning from a library. The methods involved are standard methods for a molecular biologist (Sambrook et al., 1989. *Molecular Cloning: A Laboratory Manual*, 2$^{nd}$ Edition. Cold Spring Harbor Laboratory Press, Plainview, N.Y.).

A vector is typically prepared comprising the gene encoding a molecule, such as stilbene synthase, which produces stilbenoids or the precursor or target product or intermediary product, a promoter that will drive expression of the gene in the plant and a terminator region. In this regard, any plant-compatible promoter elements can be employed in the construct, influenced by the end result desired. Those can be plant gene promoters, such as, for example, the promoter for the small subunit of ribulose-1,5-bis-phosphate carboxylase, or promoters from the tumor-inducing plasmids from *Agrobacterium tumefaciens*, such as the nopaline synthase and octopine synthase promoters, or viral promoters such as the cauliflower mosaic virus (CaMV) 19S and 35S promoters or the figwort mosaic virus 35S promoter. See Kay et al., (1987) *Science* 236:1299 and European patent application No. 0 342 926; the barley lipid transfer protein promoter, LTP2 (Kalla et al., *Plant J* (1994) 6(6): 849-60); the ubiquitin promoter (see for example U.S. Pat. No. 5,510,474); the END2 promoter (Linnestad et al. U.S. Pat. No. 6,903,205); and the polygalacturonase PG47 promoter (See Allen and Lonsdale, *Plant J.* (1993) 3:261-271; WO 94/01572; U.S. Pat. No. 5,412,085) and rice actin promoter (McElroy et al. (1990) *Plant Cell* 2:163-171). See international application WO 91/19806 for a review of various plant promoters also suitably employed in plant gene expression.

The range of available plant compatible promoters includes tissue specific and inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods.

Any inducible promoter can be used in connection with a gene expressing a molecule. See Ward et al. *Plant Mol. Biol.* 22: 361-366 (1993). Exemplary inducible promoters include ecdysone receptor promoters, U.S. Pat. No. 6,504,082; promoters from the ACE1 system which responds to copper (Mett et al. *PNAS* 90: 4567-4571 (1993)); In2-1 and In2-2 gene from maize which respond to benzenesulfonamide herbicide safeners (U.S. Pat. No. 5,364,780; Hershey et al., *Mol. Gen. Genetics* 227: 229-237 (1991) and Gatz et al., *Mol. Gen. Genetics* 243: 32-38 (1994)); the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156).

Tissue-preferred promoters can be utilized to target enhanced transcription and/or expression within a particular plant tissue. Promoters may express in the tissue of interest, along with expression in other plant tissue, may express strongly in the tissue of interest and to a much lesser degree than other tissue, or may express highly preferably in the tissue of interest. A tissue specific promoter with preferential expression in hairy roots is preferred. Such a promoter is for example the Super P promoter which harbors elements from the mannopine synthase and octopine synthase genes. This promoter has been shown to have strong expression in hairy root and low in leaves (Nopo-Olazabal et al., 2005). There are a wide variety of other tissue-preferred promoters and, by way of example, include those described in Yamamoto et al. (1997) *Plant J.* 12(2): 255-265; Kawamata et al. (1997) *Plant Cell Physiol.* 38(7): 792-803; Hansen et al. (1997) *Mol. Gen Genet.* 254(3):337-343; Russell et al. (1997) *Transgenic Res.* 6(2): 157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20: 181-196; Orozco et al. (1993) *Plant Mol Biol.* 23(6): 1129-1138; Matsuoka et al. (1993) *Proc Natl. Acad. Sci. USA* 90(20): 9586-9590; and Guevara-Garcia et al. (1993) *Plant J.* 4(3): 495-505.

Other components of the vector may be included, also depending upon intended use of the gene. Examples include selectable markers, targeting or regulatory sequences, stabilizing or leader sequences, introns etc. General descriptions and examples of plant expression vectors and reporter genes can be found in Gruber, et al., "Vectors for Plant Transformation" in *Method in Plant Molecular Biology and Biotechnology*, Glick et al eds; CRC Press pp. 89-119 (1993). The selection of an appropriate expression vector will depend upon the host and the method of introducing the expression vector into the host. The expression cassette may also include at the 3' terminus of the heterologous nucleotide sequence, a transcriptional and translational termination region functional in plants. Convenient termination regions are available from the Ti-plasmid of *A. tumefaciens*, such as the octopine synthase and nopaline synthase (nos) termination regions (Depicker et al., *Mol. and Appl. Genet.* 1:561-573 (1982)). See also, Guerineau et al. *Mol. Gen. Genet.* 262:141-144 (1991); *Proudfoot, Cell* 64:671-674 (1991); Sanfacon et al. *Genes Dev.* 5:141-149 (1991); Mogen et al. *Plant Cell* 2:1261-1272 (1990); Munroe et al. *Gene* 91:151-158 (1990); Ballas et al. *Nucleic Acids Res.* 17:7891-7903 (1989); Joshi et al. *Nucleic Acid Res.* 15:9627-9639 (1987).

Selectable reporter genes for selection of transformed cells or tissues can be included in the transformation vectors. These can include genes that confer antibiotic resistance or resistance to herbicides. Examples of suitable selectable marker genes include, but are not limited to, genes encoding resistance to chloramphenicol, Herrera Estrella et al. *EMBO J.* 2:987-992(1983); methotrexate, Herrera Estrella et al. *Nature* 303:209-213 (1983); Meijer et al. *Plant Mol. Biol.* 16:807-820 (1991); hygromycin, Waldron et al. *Plant Mol. Biol.* 5:103-108 (1985), Zhijian et al. *Plant Science* 108: 219-227 (1995); streptomycin, Jones et al. *Mol. Gen. Genet.* 210:86-91 (1987); spectinomycin, Bretagne-Sagnard et al. *Transgenic Res.* 5:131-137 (1996); bleomycin, Hille et al. *Plant Mol. Biol.* 7:171-176 (1990); sulfonamide, Guerineau et al. *Plant Mol. Biol.* 15:127-136 (1990); bromoxynil, Stalker et al. *Science* 242:419-423 (1988); glyphosate, Shaw et al. *Science* 233:478-481 (1986); and phosphinothricin, DeBlock et al. *EMBO J.* 6:2513-2518 (1987). The latter is the phosphinothricin acetyl transferase ("PAT") or maize optimized PAT or bar gene which confers resistance to bialaphos (Gordon-Kamm. 1990. *The Plant Cell* 2: 603; Uchimiya et al. 1993. Bio/Technology 11: 835; and Anzai et al, 1989. *Mol. Gen. Gen.* 219: 492).

Scorable or screenable markers may also be employed, where presence of the sequence produces a measurable product. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. *The EMBO Journal* vol. 6 No. 13 pp. 3901-3907); and alkaline phosphatase. Other screenable markers include the anthocyanin/flavonoid genes in general (See discussion at Taylor and Briggs, *The Plant Cell* (1990) 2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282

(1988)); the genes which control biosynthesis of flavonoid pigments, such as the maize C1 gene (Kao et al., *Plant Cell* (1996) 8: 1171-1179; Scheffler et al. *Mol. Gen. Genet.* (1994) 242:40-48) and maize C2 (Wienand et al., *Mol. Gen. Genet.* (1986) 203:202-207); the B gene (Chandler et al., *Plant Cell* (1989) 1:1175-1183), the p1 gene (Grotewold et al, *Proc. Natl. Acad. Sci USA* (1991) 88:4587-4591; Grotewold et al., *Cell* (1994) 76:543-553; Sidorenko et al., *Plant Mol. Biol.* (1999) 39:11-19); the bronze locus genes (Ralston et al., *Genetics* (1988) 119:185-197; Nash et al., *Plant Cell* (1990) 2(11): 1039-1049), among others. Yet further examples of suitable markers include the cyan fluorescent protein (CYP) gene (Bolte et al. (2004) *J. Cell Science* 117: 943-54 and Kato et al. (2002) *Plant Physiol* 129: 913-42), the yellow fluorescent protein gene (Phi-YFP™ from Evrogen; see Bolte et al. (2004) *J. Cell Science* 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) *EMBO J.* 8:343); a green fluorescent protein (GFP) gene (Sheen et al., *Plant J.* (1995) 8(5):777-84); and DsRed genes where plant cells transformed with the marker gene are red in color, and thus visually selectable (Dietrich et al. (2002) *Biotechniques* 2(2):286-293). Additional examples include a p-lactamase gene (Sutcliffe, *Proc. Nat'l. Acad. Sci. U.S.A.* (1978) 75:3737), which encodes an enzyme for which various chromogenic substrates are known (e.g., PADAC, a chromogenic cephalosporin); a xylE gene (Zukowsky et al., *Proc. Nat'l. Acad. Sci. U.S.A.* (1983) 80:1101), which encodes a catechol dioxygenase that can convert chromogenic catechols; an ca-amylase gene (Ikuta et al., *Biotech.* (1990) 8:241); and a tyrosinase gene (Katz et al., *J. Gen. Microbiol.* (1983) 129:2703), which encodes an enzyme capable of oxidizing tyrosine to DOPA and dopaquinone, which in turn condenses to form the easily detectable compound melanin. Clearly, many such markers are available to one skilled in the art.

The expression cassettes can additionally contain 5' leader sequences. Such leader sequences can act to enhance translation. Translation leaders are known in the art and include by way of example, picornavirus leaders, EMCV leader (Encephalomyocarditis 5' noncoding region), Elroy-Stein et al. *Proc. Nat. Acad. Sci. USA* 86:6126-6130 (1989); potyvirus leaders, for example, TEV leader (Tobacco Etch Virus), Allison et al.; MDMV leader (Maize Dwarf Mosaic Virus), *Virology* 154:9-20 (1986); human immunoglobulin heavy-chain binding protein (BiP), Macejak et al. *Nature* 353:90-94 (1991); untranslated leader from the coat protein mRNA of alfalfa mosaic virus (AMV RNA 4), Jobling et al. *Nature* 325:622-625 (1987); Tobacco mosaic virus leader (TMV), Gallie et al. (1989) *Molecular Biology of RNA*, pages 237-256; and maize chlorotic mottle virus leader (MCMV) Lommel et al. *Virology* 81:382-385 (1991). See also Della-Cioppa et al. *Plant Physiology* 84:965-968 (1987).

The cassette can also contain sequences that enhance translation and/or mRNA stability such as introns. Other modifications can improve expression, include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, *Zea mays* Brittle-1 chloroplast transit peptide (Nelson et al. *Plant Physiol* 117(4):1235-1252 (1998); Sullivan et al. *Plant Cell* 3(12):1337-48; Sullivan et al., *Planta* (1995) 196(3):477-84; Sullivan et al., *J. Biol. Chem.* (1992) 267 (26):18999-9004) and the like. One skilled in the art will readily appreciate the many options available in expressing a product to a particular organelle. For example, the barley alpha amylase sequence is often used to direct expression to the endoplasmic reticulum (Rogers, *J. Biol. Chem.* 260: 3731-3738 (1985)). Use of transit peptides is well known (e.g., see U.S. Pat. Nos. 5,717,084; 5,728,925).

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions, such as transitions and transversions, can be involved.

In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al. (supra).

The method of transformation/transfection is not critical ntion; various methods of transformation or transfection are currently available. As newer methods are available to transform crops or other host cells they may be directly applied. Accordingly, a wide variety of methods have been developed to insert a DNA sequence into the genome of a host cell to obtain the transcription or transcript and translation of the heterologous sequence. Thus, any method which provides for efficient transformation/transfection may be employed.

Methods for introducing expression vectors into plant tissue available to one skilled in the art are varied and will depend on the plant selected. Procedures for transforming a wide variety of plant species are well known and described throughout the literature. See, for example, Miki et al, "Procedures for Introducing Foreign DNA into Plants" in *Methods in Plant Molecular Biotechnology*, supra; Klein et al, *Bio/Technology* 10:268 (1992); and Weising et al., *Ann. Rev. Genet.* 22: 421-477 (1988). For example, the DNA construct may be introduced into the genomic DNA of the plant cell using techniques such as microprojectile-mediated delivery, Klein et al., *Nature* 327: 70-73 (1987); electroporation, Fromm et al., *Proc. Natl. Acad. Sci.* 82: 5824 (1985); polyethylene glycol (PEG) precipitation, Paszkowski et al., *EMBO J.* 3: 2717-2722 (1984); direct gene transfer WO 85/01856 and EP No. 0 275 069; in vitro protoplast transformation, U.S. Pat. No. 4,684,611; and microinjection of plant cell protoplasts or embryogenic callus, Crossway, *Mol. Gen. Genetics* 202:179-185 (1985). Co-cultivation of plant tissue with *Agrobacterium tumefaciens* is another option, where the DNA constructs are placed into a binary vector system. See e.g., U.S. Pat. No. 5,591,616; Ishida et al., "High Efficiency Transformation of Maize (*Zea mays* L.) mediated by *Agrobacterium tumefaciens*" *Nature Biotechnology* 14:745-750 (1996). The virulence functions of the *Agrobacterium tumefaciens* host will direct the insertion of the construct into the plant cell DNA when the cell is infected by the bacteria. See, for example Horsch et al., *Science* 233: 496-498 (1984), and Fraley et al., *Proc. Natl. Acad. Sci.* 80: 4803 (1983).

Standard methods for transformation of canola are described at Moloney et al. "High Efficiency Transformation of *Brassica napus* using *Agrobacterium* Vectors" Plant *Cell Reports* 8:238-242 (1989). Corn transformation is described by Fromm et al, *Bio/Technology* 8:833 (1990) and Gordon-Kamm et al, supra. *Agrobacterium* is primarily used in dicots, but monocots can be transformed by *Agrobacterium*. See supra and U.S. Pat. No. 5,550,318. Rice transformation is described by Hiei et al., "Efficient Transformation of Rice (*Oryza sativa* L.) Mediated by *Agrobacterium* and Sequence Analysis of the Boundaries of the T-DNA" *The Plant Journal* 6(2): 271-282 (1994, Christou et al, *Trends in Biotechnology* 10:239 (1992) and Lee et al, *Proc. Nat'l Acad. Sci. USA* 88:6389 (1991). Wheat can be transformed by techniques similar to those used for transforming corn or rice. *Sorghum* transformation is described at Casas et al, supra and *sorghum* by Wan et al, *Plant Physicol.* 104:37 (1994). Soybean transformation is described in a number of publications, including U.S. Pat. No. 5,015,580.

When referring to "introduction" of the nucleotide sequence into a plant, it is meant that this can occur by direct transformation methods, such as *Agrobacterium* transformation of plant tissue, microproj ectile bombardment, electroporation, or any one of many methods known to one skilled in the art; or, it can occur by crossing a plant having the heterologous nucleotide sequence with another plant so that progeny have the nucleotide sequence incorporated into their genomes. Such breeding techniques are well known to one skilled in the art. For a discussion of plant breeding techniques, see Poehlman (1995) *Breeding Field Crops*. AVI Publication Co., Westport Conn., 4$^{th}$ Edit. Backcrossing methods may be used to introduce a gene into the plants. This technique has been used for decades to introduce traits into a plant. An example of a description of this and other plant breeding methodologies that are well known can be found in references such as Poelman, supra, and *Plant Breeding Methodology*, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

Scale up of the production of molecules from hairy root cultures may be achieved by any of the known systems for plant propagation, and the invention is not limited by the means of increasing production of resveratrol and other stilbenes. For example, an airlift mesh-draught is one example (Caspeta et al. 2005); another uses a mesh support system (Ramakrishnan et al., 2004). A bioreactor system is further described below. One skilled in the art appreciates that there are many variations on the components and processes with which the nucleotide sequence of the invention may be used. See in patent '677 and US publication 201030623 the figures and examples for illustrations of methods for producing stilbenes in plants.

To increase the amount of a product of interest in plants, plant parts, and/or cells, a precursor of the product of interest is contacted with the plant or plant part. Such precursors may include, but are not limited to piceatannol, squalene, acetate, phenylalanine, coumaric acid, cinnamic acid, tryptophan, and putrescine. One or more of the precursors may be applied to the plant, plant part, and/or cells. The amount of precursor applied to the plant, plant part, and/or cell may vary depending on the product of interest.

The use of the precursor may result in feedback inhibition of production of the product of interest. The use of a trapping or binding agent may limit and/or prevent the feedback inhibition. The trapping or binding agent complexes with compounds in the pathway and traps the product or intermediate.

Such trapping agents may include, but are not limited to cyclodextrin, alpha-cyclodextrin, beta-cyclodextrin, gamma-cyclodextrin. In one embodiment, the trapping agent is not permanently bound to the product of interest. In other embodiments, the trapping agent may be used if feedback inhibition does not occur. One or more of the trapping agents may be applied during the process. For example, certain trapping agents, such as a cyclodextrin may be used in combination with methyl jasmonate for trapping the product of interest or intermediate. The period of incubation with the trapping agent and elicitor could vary depending on the desired product.

In one embodiment, the trapping agent to be used may be selected based upon the product of interest. Such a trapping agent is selected to maximize trapping the product of interest. In such an embodiment, the characteristics of the product of interest may be considered in selecting the trapping agent. For example, the polarity of the product of interest may be considered when selecting the trapping agent. In such an embodiment, the trapping agent to be used has a polarity that will attract the product of interest based upon the polarity of the product of interest.

In one example, the plant or plant culture is contacted with the putative precursor, elicitor and trapping agent for any period of time. The product of interest is then extracted from the culture medium or the plant tissue. The product of interest could be any compound such as a phenolic, terpenoid and alkaloid. In one example, the desired product of interest could be naturally produced by the plant upon treatment with an elicitor. As an example, such compound is a stilbene. In another example the desired product is a new compound that is produced when a xenobiotic is added to the culture. As an example such compound is a glucuronide. Preferred features and embodiments of each aspect of the invention are as for each of the other aspects mutatis mutandis unless context demands otherwise.

The following examples are presented by way of illustration and are not intended to be limiting. All references cited herein are incorporated herein by reference.

Example 1. Biosynthesis Enhancement of Arachidin-1 in Hairy Root Cultures of Peanut Stilbenoids are polyphenolic compounds with important applications in human health. These natural products exhibit antioxidant, anti-inflammatory and anticancer properties.

Resveratrol, a stilbenoid produced by certain plant species such as grape and peanut, has been the most studied among this group of polyphenolic compounds. Previously we demonstrated the application of hairy root cultures as bioproduction system for stilbenoids including resveratrol and its analogs and derivatives. Indeed, we showed that hairy root cultures of peanut can produce resveratrol and several prenylated stilbenoids, including arachidin-1 and arachidin-3, upon treatment with sodium acetate. We further described the purification of arachidin-1 and arachidin-3 from the medium of sodium acetate-treated hairy root cultures using centrifugal partition chromatography chromatography (CPC). In a recent study we showed that arachidin-1 and arachidin-3 have affinity to cannabinoid receptors. See US Published patent application No. 20120165281 incorporated herein by reference in its entirety. Compounds that modulate cannabinoid receptor have applications in neuroprotection, control of obesity and drug addiction. Furthermore, we also demonstrated that arachidin-1 has higher antioxidant activities than resveratrol in vitro. Studies concerning arachidin-1 and arachidin-3 have demonstrated that these prenylated stilbenoids have favorable metabolic profiles in vitro when compared to resveratrol. See US Published patent application No. 20120165281. Because of their higher lipophilicity and favorable metabolic profiles, the arachidins may be more bioavailable than resveratrol. Whereas resveratrol is commercially available as a synthetic and natural product, arachidin-1 and arachidin-3 are not available through any commercial sources. Studies with these stilbenoids have only been conducted by extracting these polyphenols from peanut seeds challenged with fungus or peanut hairy roots treated with elicitors. Due to the importance of the arachidins, in particular arachidin-1, we designed strategies to increase the levels of this compound in peanut hairy root cultures.

Hairy roots of peanut cv. Hull line 3 were cultured for 9 days in a modified Murashige & Skoog medium at 28° C., under shaking (90 rpm) and continuous darkness. At day 9, the spent medium was removed and the conductivity of the medium was measured. The spent medium was replaced with fresh medium containing between 0.5 to 75 mM of β-cyclodextrin, such as 7.5 mM of β-cyclodextrin, (trapping agent) and between 10 and 500 μM methyl jasmonate, such as 100 μM methyl jasmonate, (MeJA, inducer/elicitor) with or without 0.05 to 10 mM piceatannol, such as 1 mM piceatannol (putative biosynthetic precursor or xenobiotic). Control cultures included ethanol (solvent of MeJA) only. Cultures were incubated for additional 24 hours as described above and then the medium was collected. The stilbenoids were extracted from the culture medium with ethyl acetate and this organic fraction was dried to completeness under nitrogen stream. The extract was resuspended in methanol and analyzed by reversed phase HPLC. Detection was done with a photodiode array detector. Arachidin-1 was confirmed by comparison to the retention time and UV spectrum of an authentic arachidin-1 standard. In addition, previous analyses by mass spectrometry confirmed the presence of arachidin-1 in induced hairy root cultures of peanut. Quantification of arachidin-1 was done by HPLC using a calibration curve of authentic arachidin-1 standards.

Figure 6A:
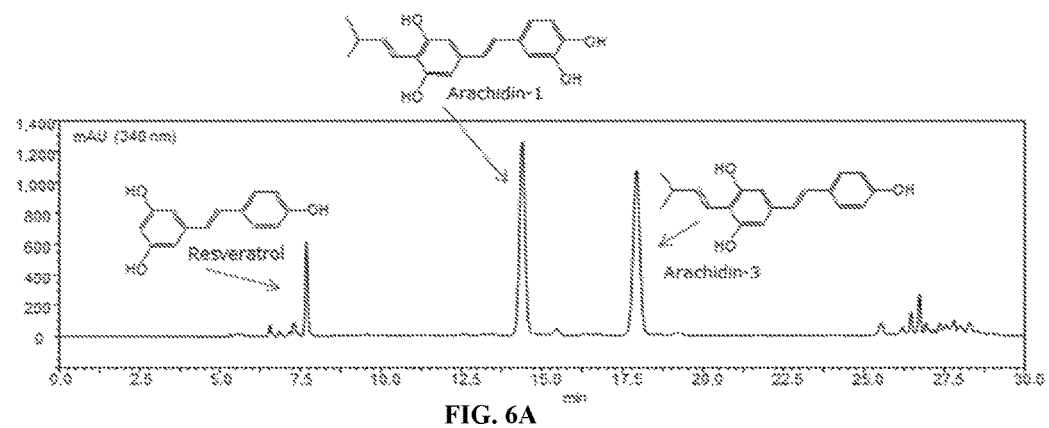
FIG. 6A-C are graphs showing elicitation of stibenoids by sodium acetate (FIG. 6A) and where piceatannol was added (FIG. 6B) and where piceatannol was used alone without sodium acetate (FIG. 6C).
Figure 6B:
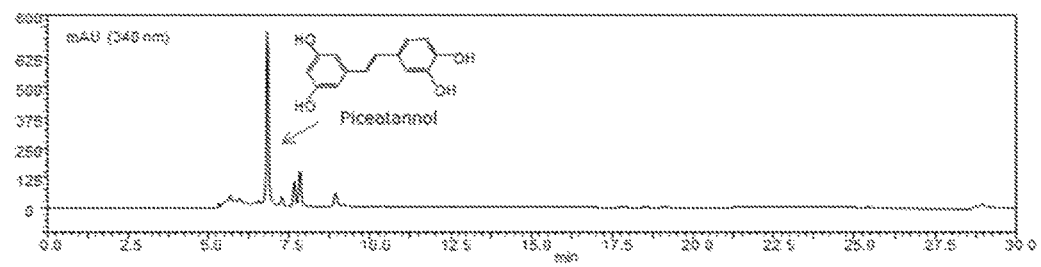

In a first experiment, the effect of piceatannol feeding in sodium acetate treated hairy root cultures of peanut was examined, with results shown in FIGS. 6A and 6B. As can be seen, adding sodium acetate elicitor resulted in production of stilbenoids (resveratrol, arachidin-1 and arachidin-3) in hairy root cultures of plant (FIG. 6A). Adding piceatannol resulted in inhibition of stilbenoid production (FIG. 6B).

Figure 6C:
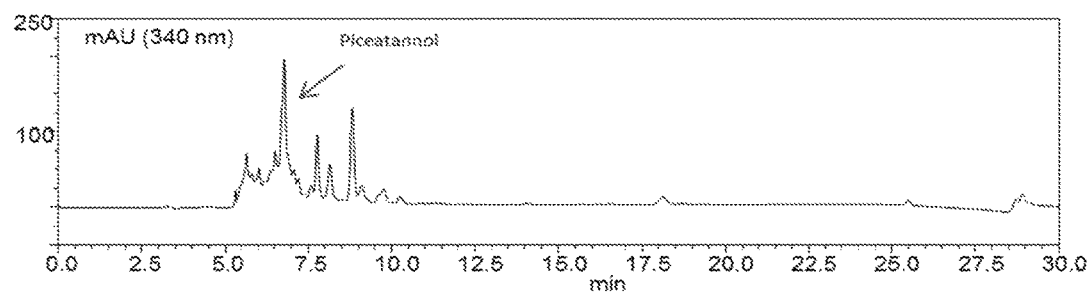

The impact of inhibition by piceatannol was overcome by adding the trapping agent cyclodextrin, which stopped the feedback inhibition, as seen in FIG. 7A-C. Used alone without an elicitor, no stilbenoids were produced (FIG. 6C).

FIG. 7 shows the HPLC chromatogram of the stilbenoids at 340 nm (UV max of arachidin-1):

FIG. 7A: Control cultures. The yield of arachidin-1 (peak with retention time of 14.217 minutes) was approximately 0.00006 mg/L;

FIG. 7B: Cultures treated with cyclodextrin and MeJA. The yield of arachidin-1 (peak with retention time of 14.5 minutes) was approximately 0.2 mg/L;

FIG. 7C: Cultures treated with cyclodextrin, MeJA and piceatannol. The yield of arachidin-1 (peak with retention time of 14.35 minutes) was approximately 15 mg/L. Due to the high amount of arachidin-1 in this sample, the extract was diluted before quantitation analysis.

The yield of arachidin-1 was enhanced approximately 250,000 fold in the cultures treated with cyclodextrin, MeJA and piceatannol when compared to control culture. The biosynthetic pathway of arachidin-1 has not been elucidated. Interestingly, in this experiment piceatannol was converted into arachidin-1 suggesting a potential role for piceatannol as a metabolic precursor. An alternative role of piceatannol is as a xenobiotic. In this case, enzymes in the metabolic pathway of arachidin-1 were able to convert piceatannol to arachidin-1. The high levels of arachidin-1 attained in this study indicate a potential role of cyclodextrin in preventing the intrinsic regulatory mechanisms driven by intermediates and products in the arachidin-1 metabolic pathway.

Example 2. Biosynthesis Enhancement of Flavonoids in Hairy Root Cultures of *Scutellaria Lateriflora*

The genus *Scutellaria* has been widely studied due to its health benefits including, but not limited to, anti-allergic, anti-bacterial, anti-HIV, anti-hepatitis, antioxidant, and anti-tumor activities. Two of the most widely studied species of *Scutellaria* are *S. baicalensis* and *S. lateriflora* due to both exhibiting the aforementioned properties and being officially recognized herbal product sources. *S. lateriflora* commonly referred to as the American skullcap, has been used for centuries by Europeans and Native Americans as a nerve tonic, sedative, and anticonvulsant. Recent studies have shown that flavonoids present in *S. lateriflora* extracts possess strong antitumor properties and therefore these compounds merit further study. In order to study the biosynthesis of the bioactive flavonoids in *S. lateriflora* we developed hairy root cultures of this species. Line 4 was selected for further studies based on its growth performance. To manipulate the levels of flavonoids, hairy roots of *S. lateriflora* line 4 were cultured for 30 days in a modified Murashige & Skoog medium at 28° C., under shaking (90 rpm) and continuous light. At day 30, the spent medium was removed and the conductivity measured. The spent medium was replaced with fresh medium containing between 0.5 to 75 mM of β-cyclodextrin, such as 15 mM of β-cyclodextrin, (trapping agent) and 10 to 500 μM methyl jasmonate, such as 100 μM methyl jasmonate (MeJA, inducer) with a putative precursor between 0.05 to 10 mM of chrysin, such as 1 mM chrysin, or between 0.05 to 10 mM of naringenin, such as 1 mM naringenin). Control cultures included β-cyclodextrin and MeJA without the putative precursor. Cultures were incubated for additional 24 hours as described above and then the roots and medium were collected. The flavonoids are extracted from the tissue and culture medium with either ethyl acetate or methanol and then the extracts are dried to completeness under nitrogen stream. The extracts are resuspended in methanol and analyzed by reversed phase HPLC. Detection of flavonoids is done with a photodiode array detector. The levels of acteoside, wogonin, wogonoside, baicalein baicalin, scutellarein and scutellarin are determined in extracts from the tissue. In addition, the levels of inducible and secreted compounds are determined in the culture medium.

Figure 8:
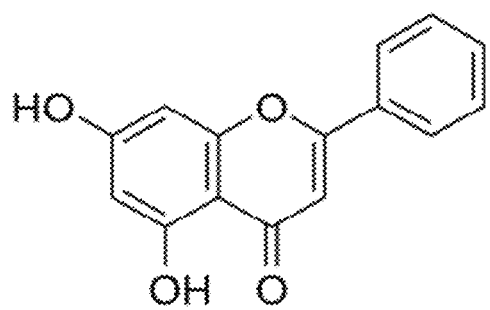
FIG. 8 is a diagram showing the chemical structure of chrysin.
Figure 9:
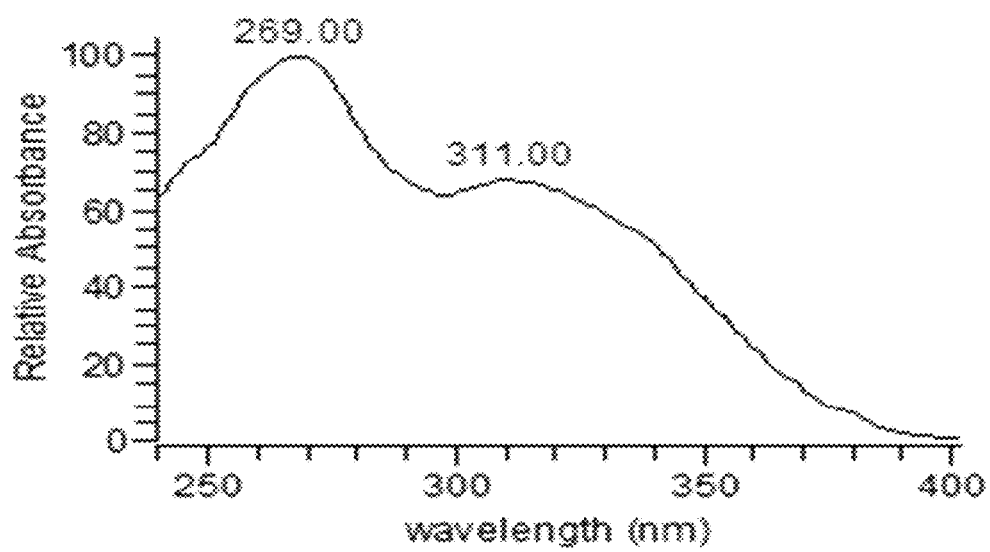
FIG. 9 is a graph showing the UV spectrum of chrysin.
Figure 10:
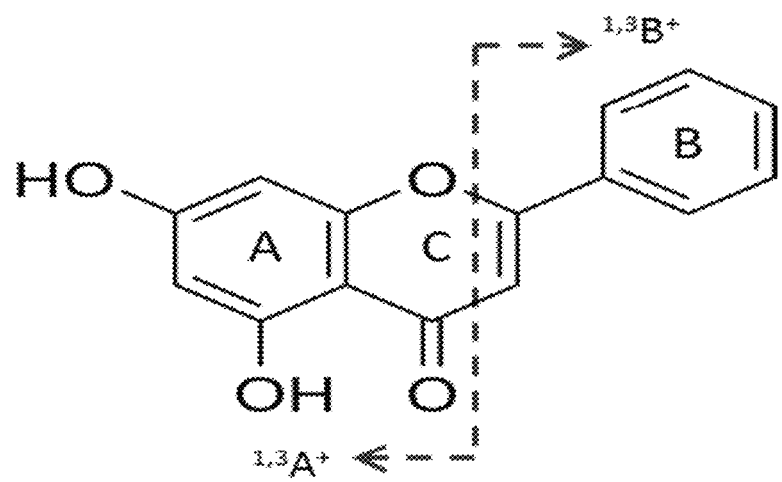
FIG. 10 is a diagram showing the fragmentation pattern of chrysin
Figures 11A, 11B:
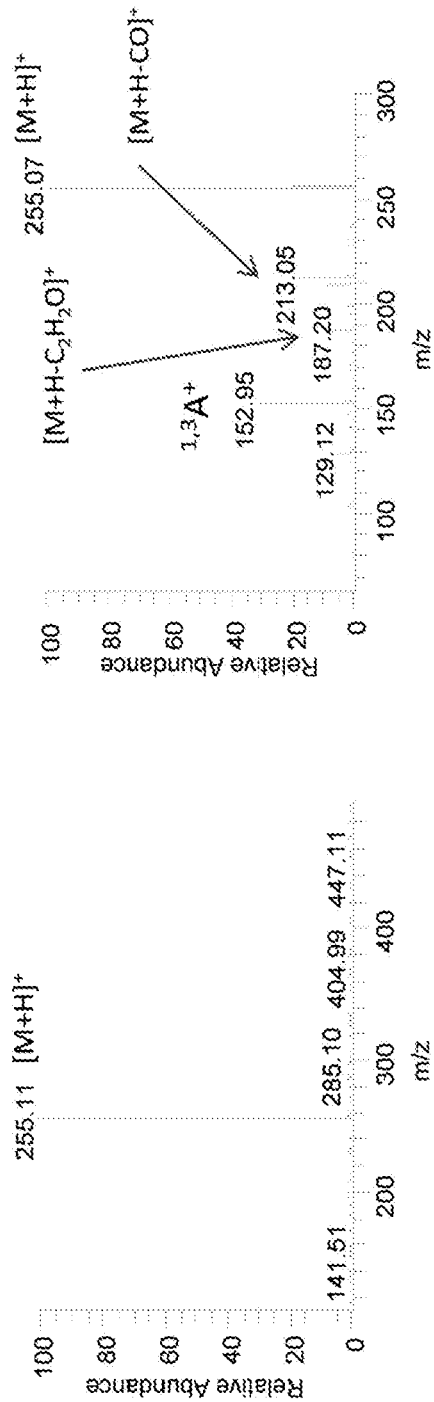
FIG. 11A-B is a graph showing mass spectrometry (MS) spectrum of chrysin (A) and MS2 spectrum of selected ion 255 (B).

Absorption and mass spectrometry analysis of chrysin reference standard is shown in FIGS. 8-21. In FIG. 8, the chemical structure of chrysin is shown, FIG. 9 shows UV spectrum, the fragmentation pattern of chrysin is shown in FIG. 10, and in FIG. 11 mass spectrometry (MS) spectrum of chrysin (A) and MS2 spectrum of selected ion 255 (B) are shown.

Figure 12A:
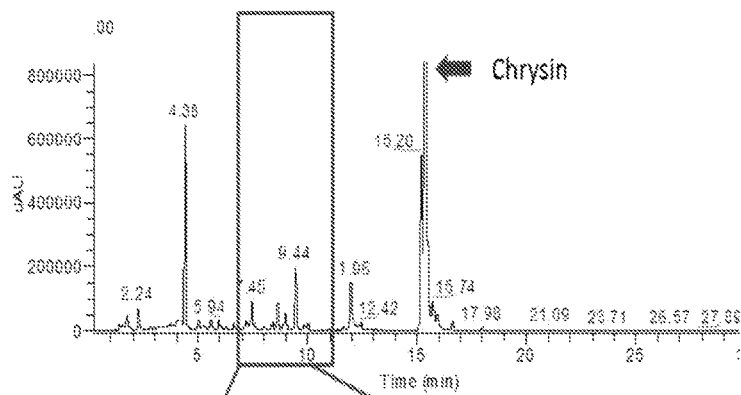
FIGS. 12A-B are graphs showing production of novel chrysin derivatives in 12A and showing increased detail at 12B.
Figure 12B:
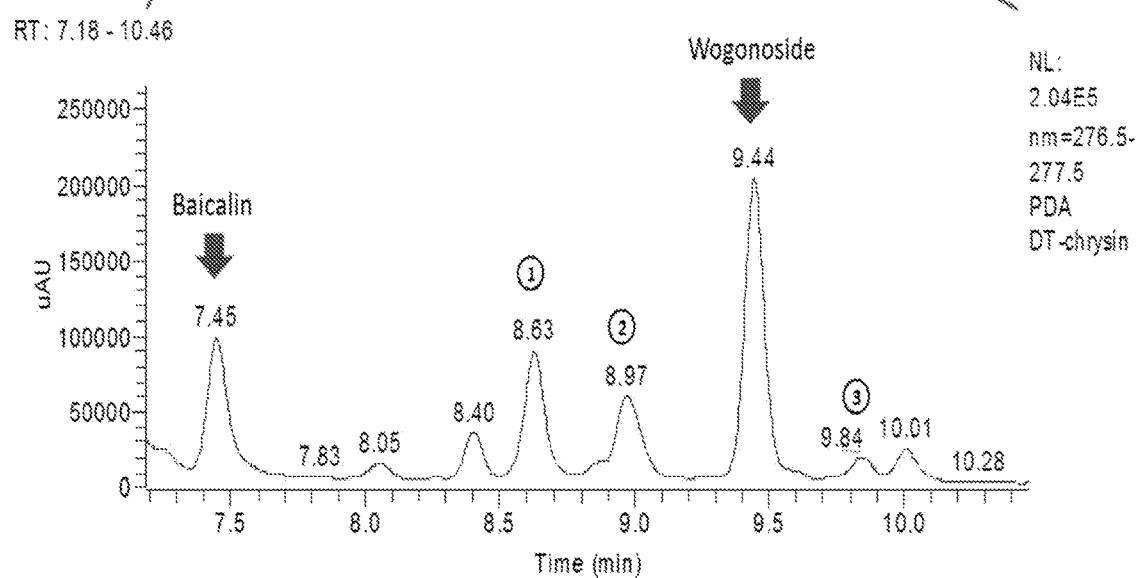

The results of analysis for compounds produced by addition of chrysin is shown in FIG. 12. In FIG. 12A, the peak representing chrysin is identified along with new compounds, shown in detail in FIG. 12B. Novel chrysin derivatives are shown at peaks 1, 2 and 3 produced in the tissue of hairy roots of *S. lateriflora*. These cultures were fed with 1 mM chyrsin together with 15 mM cyclodextrin and 100 µM methyl jasmonate. As described above, compounds were extracted with methanol from the lyophilized hairy root tissue and analyzed by HPLC-PDA. In other embodiments, the cultures may be fed with 0.5 to 10 mM chrysin, such as 1 mM chrysin together with 0.5 to 75 mM cyclodextrin, such as 15 mM cyclodextrin, and 10 to 500 µM methyl jasmonate, such as 100 µM methyl jasmonate.

Figure 13:
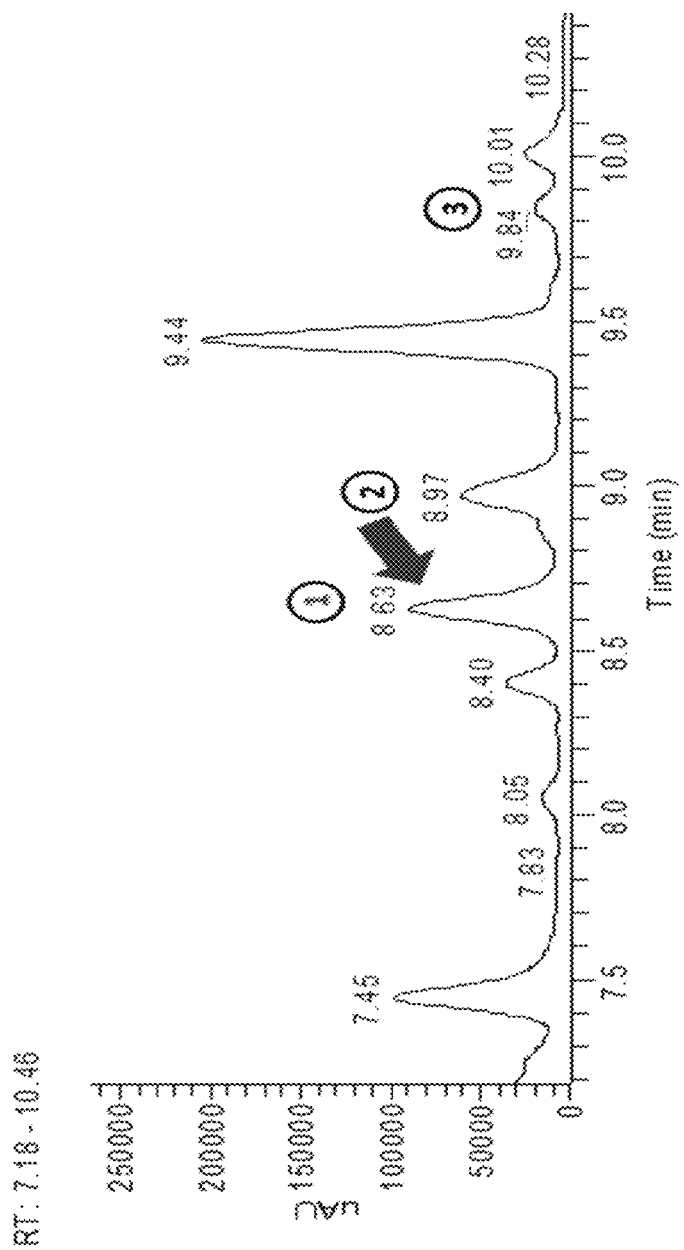
FIG. 13 is a graph showing compounds derived from chrysin with peak 1 identified by arrow and number.
Figure 14:
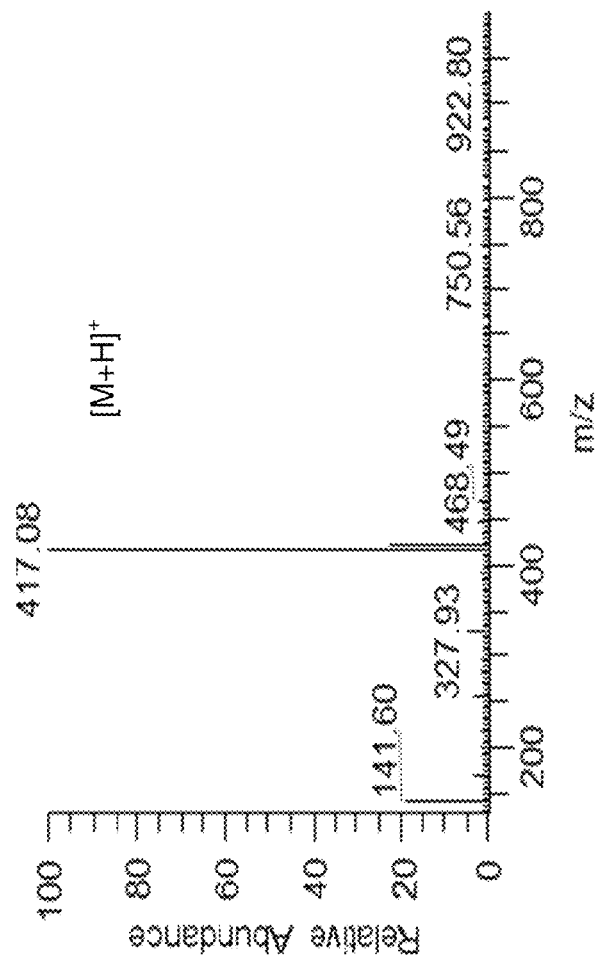
FIG. 14 is a graph showing mass spectrometry analysis of the chrysin glucoside produced in peak 1.
Figure 15:
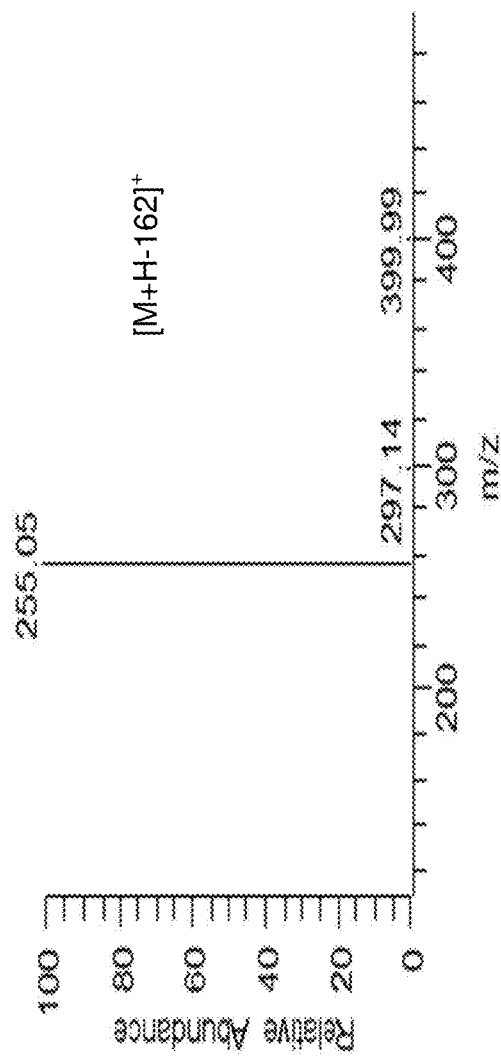
FIG. 15 is a graph showing MS2 spectrum of peak 1.
Figure 16:
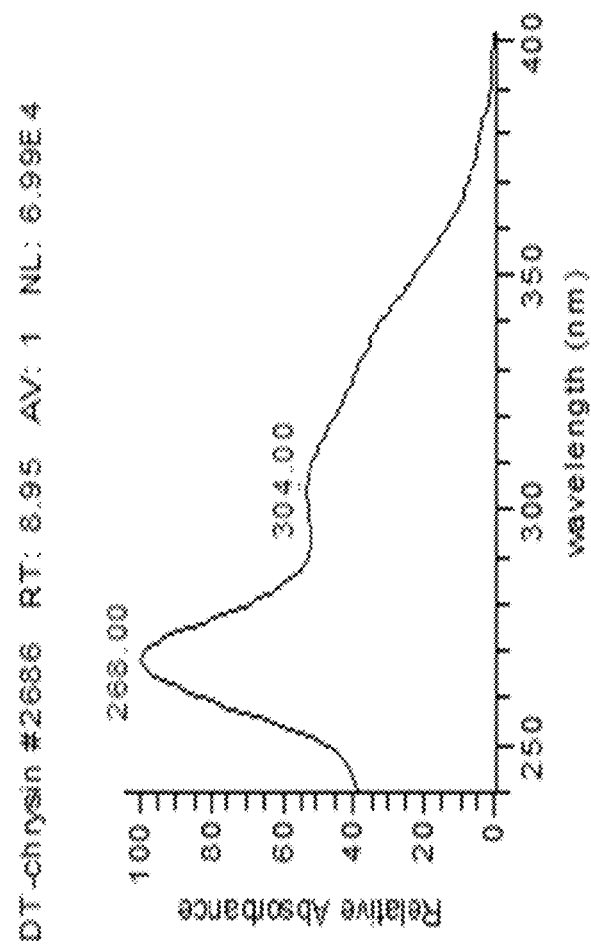
FIG. 16 is a graph showing UV spectrum of peak 1.
Figure 17:
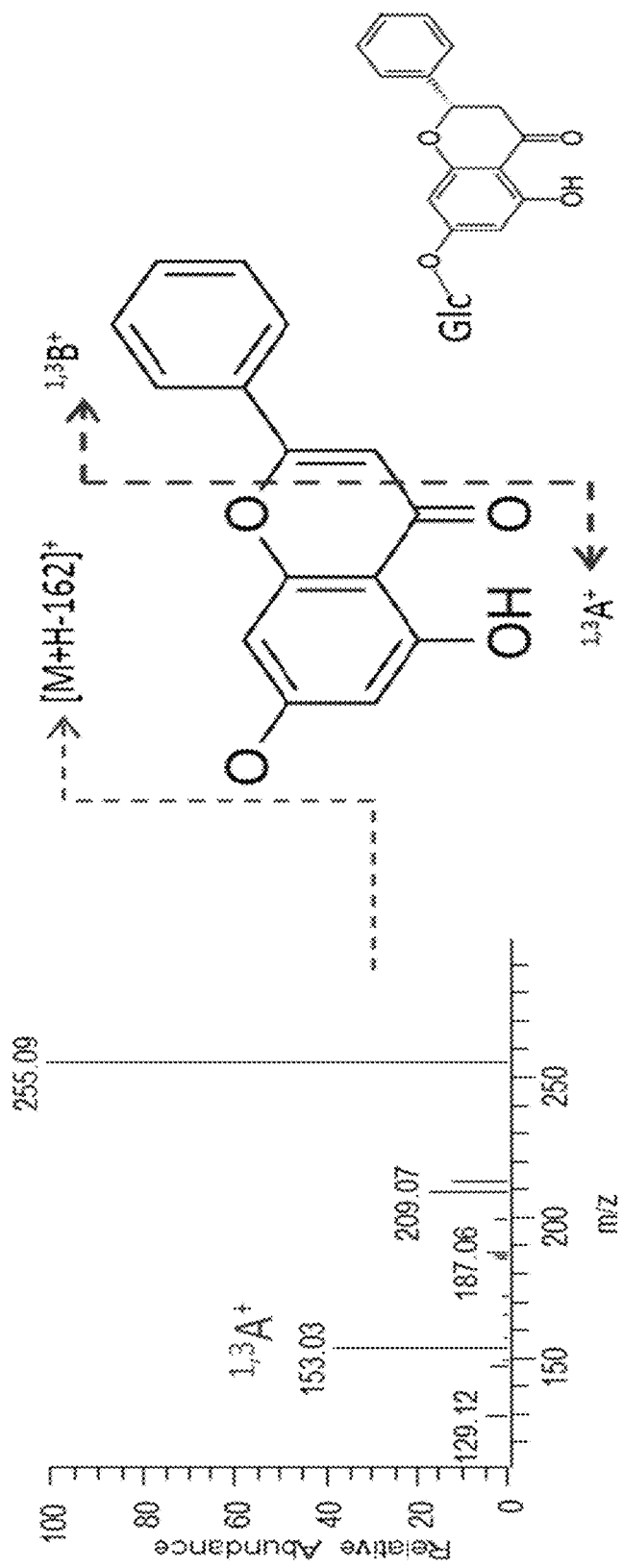
FIG. 17 is a graph showing MS3 spectrum of peak 1 and the predicted fractionation patterns of the compound.

Further analysis of the compound derived from chrysin represented in peak 1 is shown in FIG. 13-17. FIG. 13 shows absorption and mass spectrometry analysis of chyrsin glucoside, seen as peak 1 (arrow) in FIG. 13. The MS spectrum of peak 1 is shown in the graph of FIG. 14, the MS2 spectrum of peak 1 in FIG. 15 and the UV spectrum in FIG. 16 and MS3 spectrum of peak 1 in FIG. 17 along with the predicted fractionation patterns of the compound.

Figure 18:
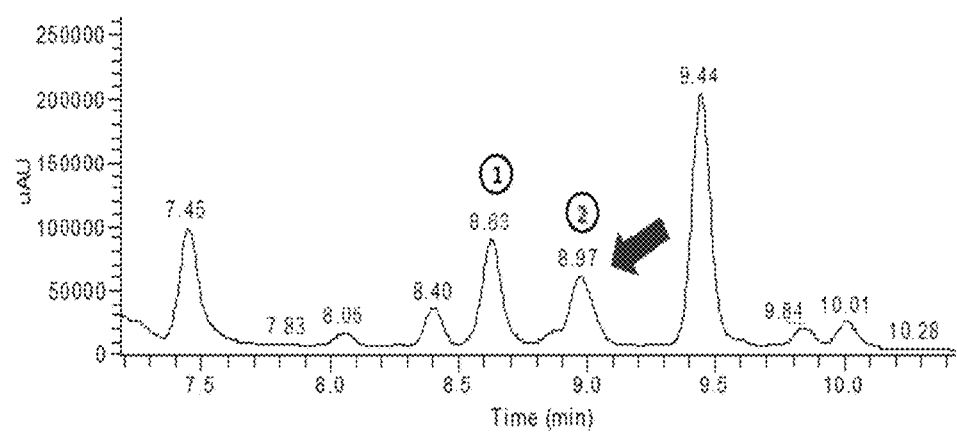
FIG. 18 is a graph showing compounds derived from chrysin with peak 2 identified by arrow and number.
Figure 19:
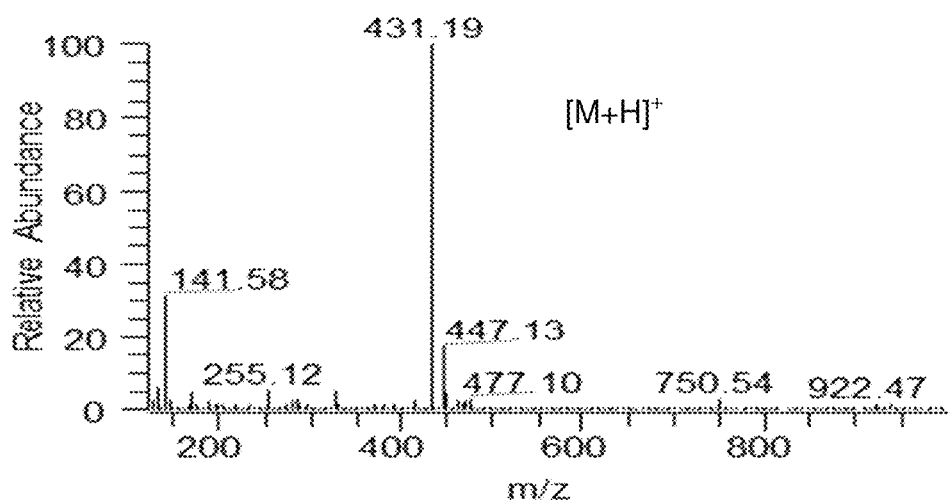
FIG. 19 is a graph showing mass spectrometry analysis of the chrysin glucuronide produced in peak 2.
Figure 20:
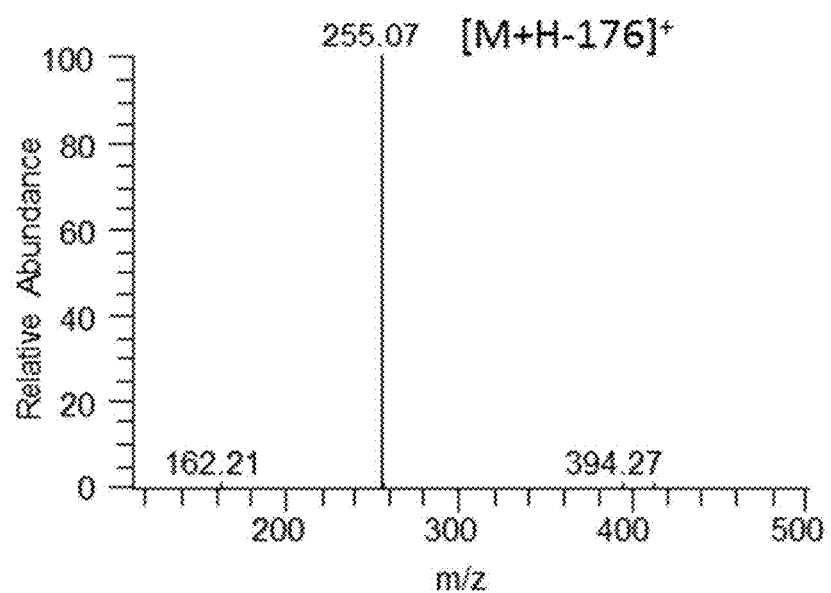
FIG. 20 is a graph showing MS2 spectrum of peak 2.
Figure 21:
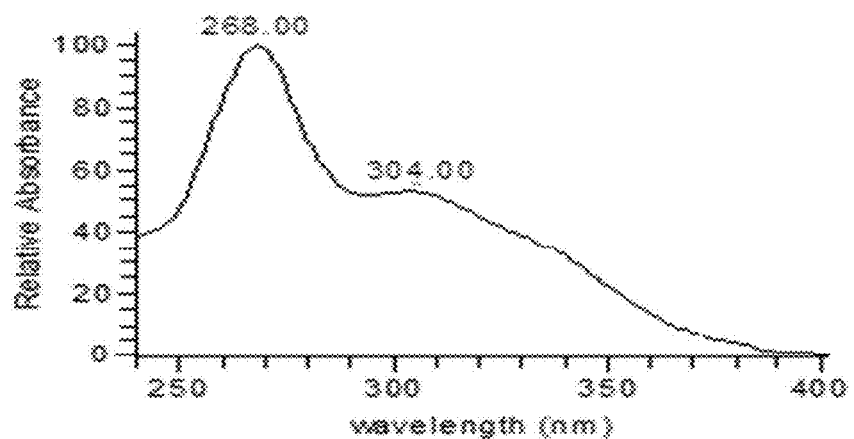
FIG. 21 is a graph showing UV spectrum of peak 2.
Figure 22A:
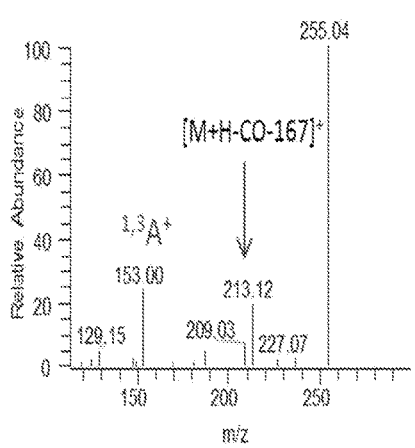
FIG. 22A is a graph showing MS3 spectrum of peak 2 and FIG. 22B the predicted fractionation patterns of the compound.
Figure 22B:
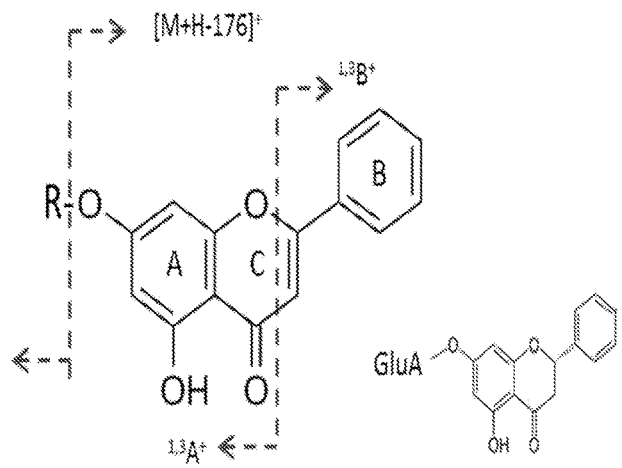

Peak 2 as identified in FIG. 18 by arrow is a chrysin glucuronide produced and further analysed. FIG. 19 shows the MS spectrum of peak 2, FIG. 20 shows MS2 spectrum and FIG. 21 shows the UV spectrum and FIG. 22A the MS3 spectrum and FIG. 22B the predicted fractionation pattern of the compound.

Figure 23A:
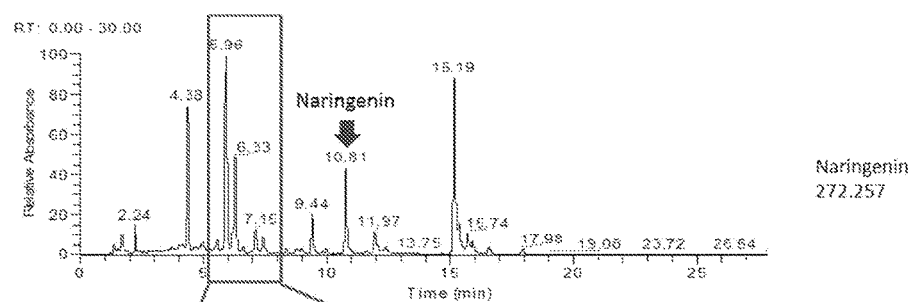
FIG. 23A-B are graphs showing production of novel naringenin derivatives in 23A and showing increased detail at 23B.
Figure 23B:
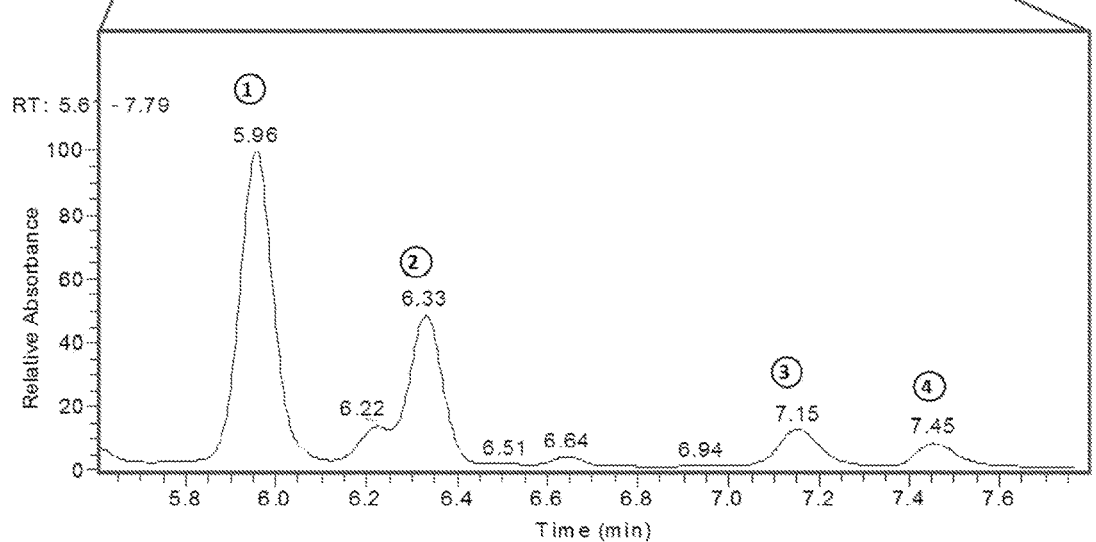
Figure 24:
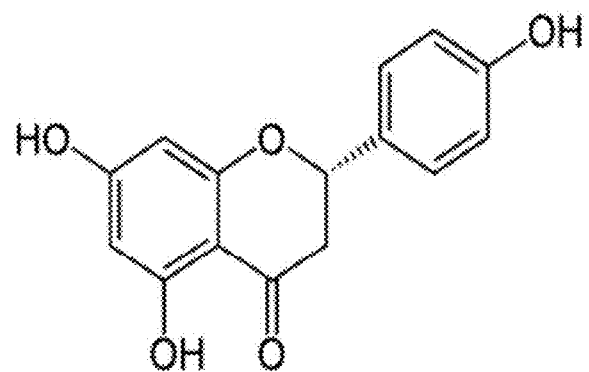
FIG. 24 shows the chemical structure of naringenin.
Figure 25:
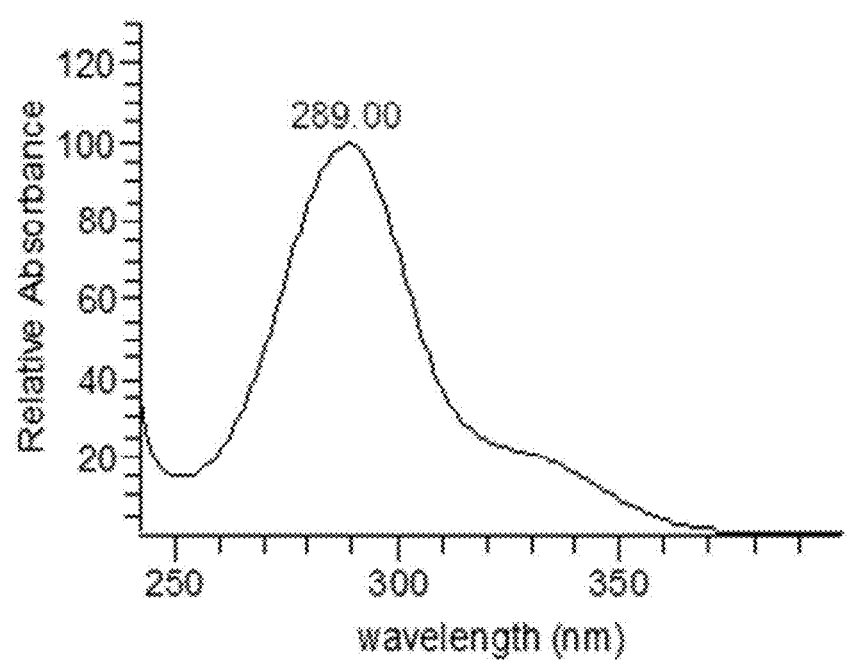
FIG. 25 is a graph showing the UV spectrum of naringenin.

Using another precursor, narigenin, still further new narigenin derivatives were produced in the tissue of hairy root cultures of *S. lateriflora*, as reflected in FIG. 23. FIG. 23A shows the identification of naringenin, and detail of four derivatives seen at peaks 1-4 shown in FIG. 23B. These compounds were extracted with methanol from the lyophilized hairy root tissue and analyzed by HPLC-PDA. The chemical structure of naringenin is shown in FIG. 24 and a graph showing the UV spectrum of naringenin in FIG. 25.

Figure 26:
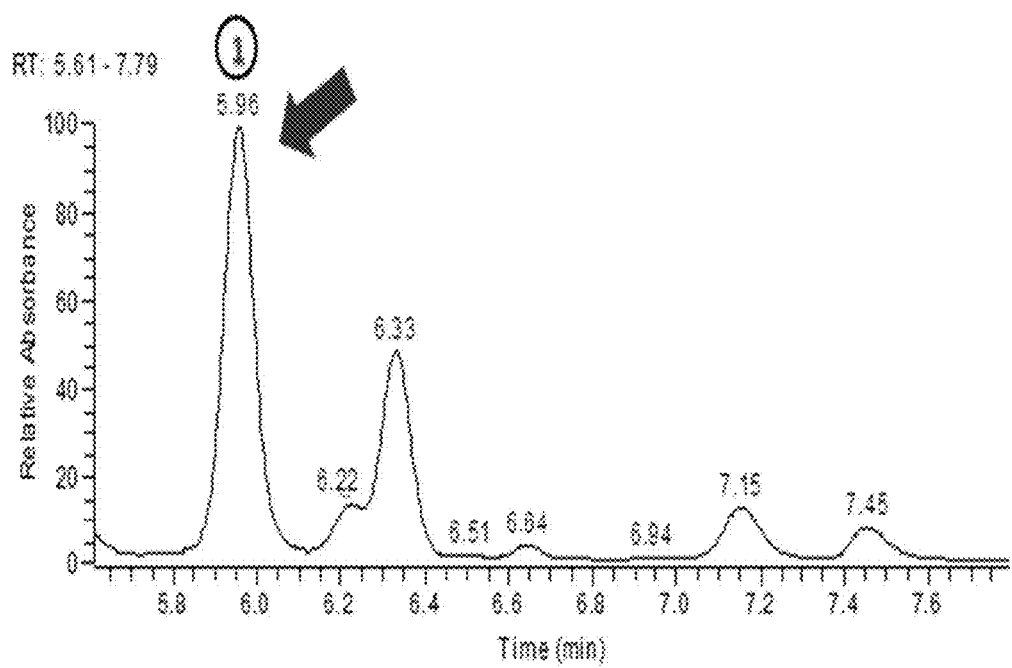
FIG. 26 is a graph showing compounds derived from naringenin with peak 1 identified by arrow and number.
Figure 27:
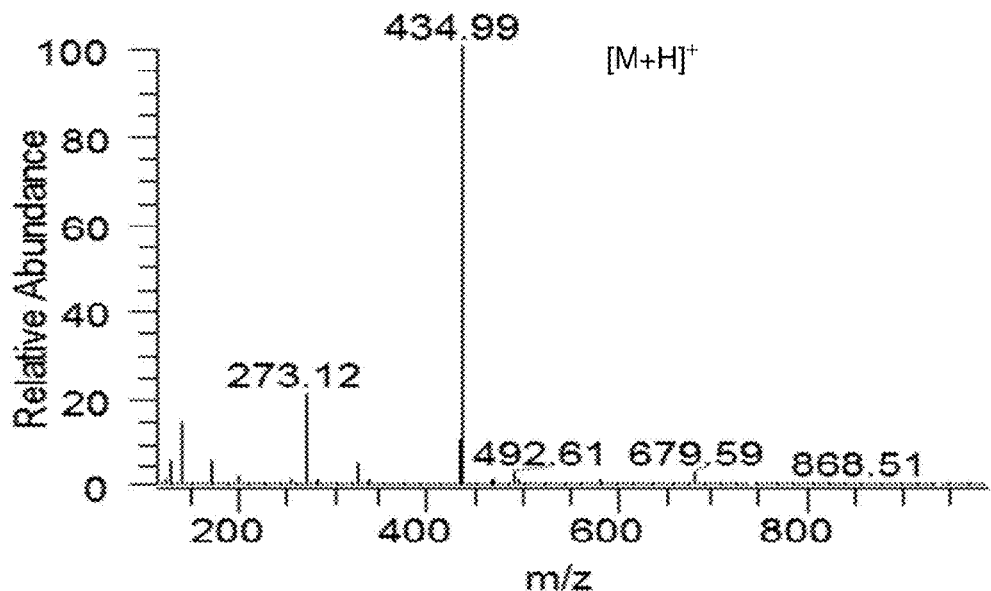
FIG. 27 is a graph showing MS spectrum of peak 1.
Figure 28:
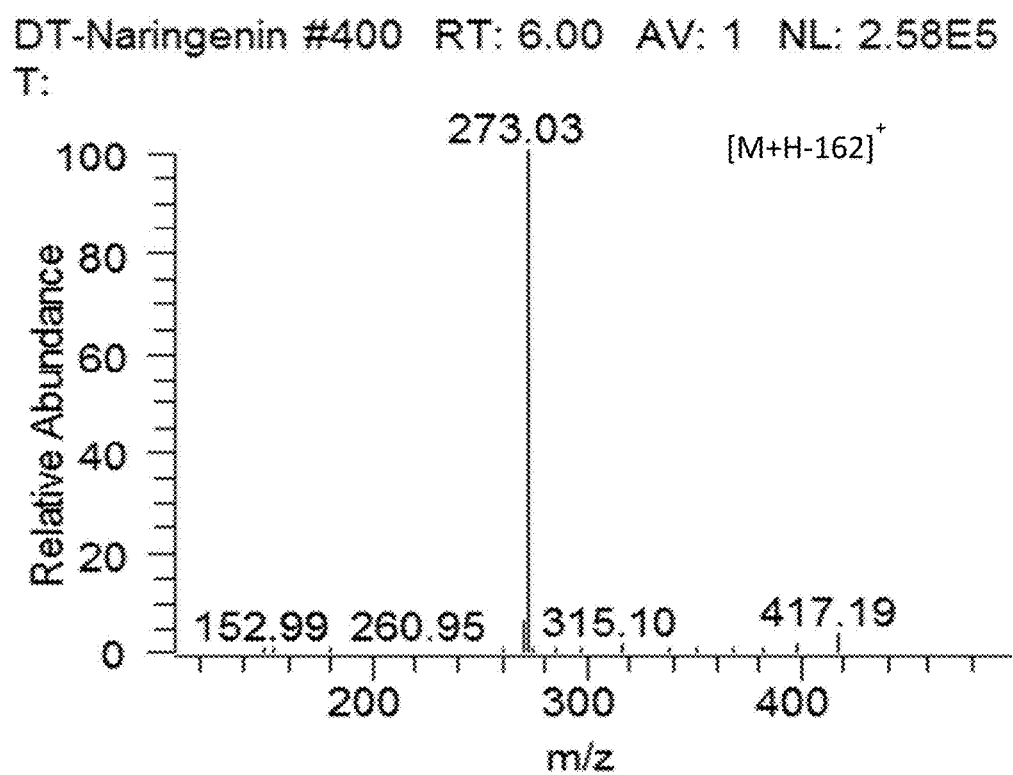
FIG. 28 is a graph showing MS2 spectrum of peak 1.
Figure 29B:
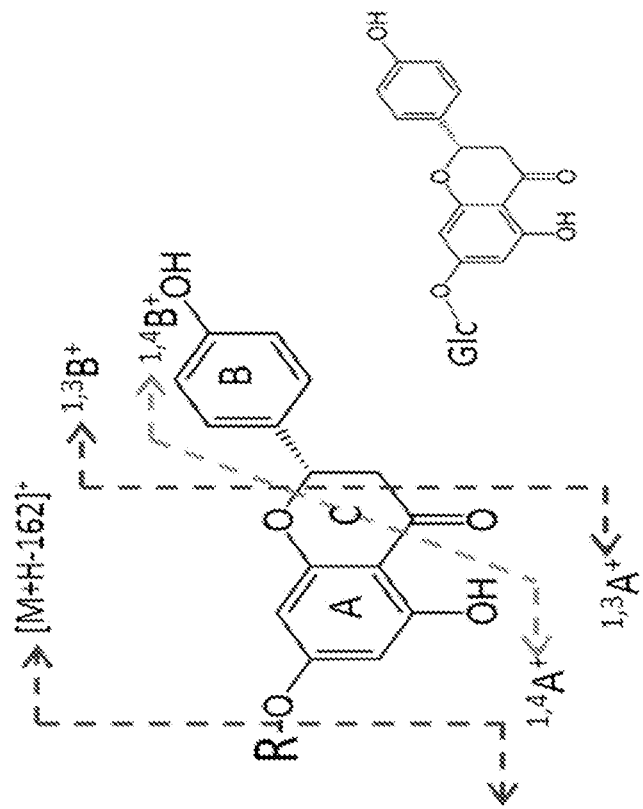
FIG. 29A is a graph showing the UV spectrum of peak 1 and FIG. 29 B shows the predicted fractionation patterns of the compound.
Figure 29A:
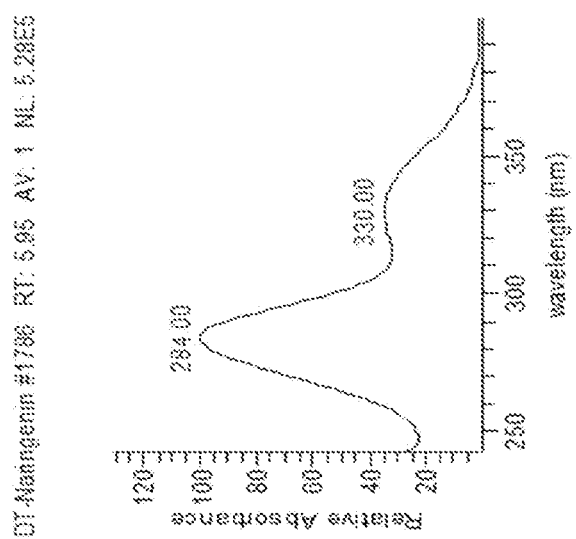
Figure 30:
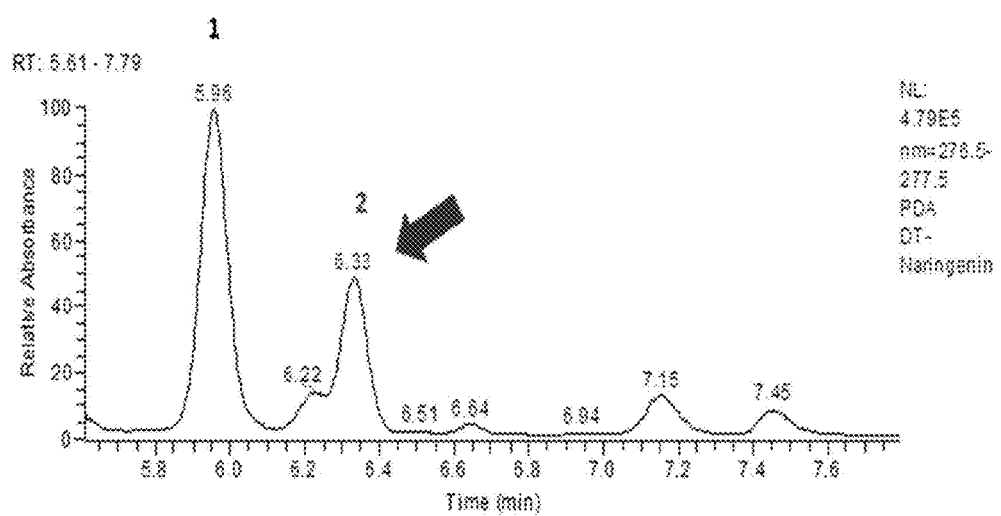
FIG. 30 is a graph showing compounds derived from naringenin with peak 2 identified by arrow and number.
Figure 31:
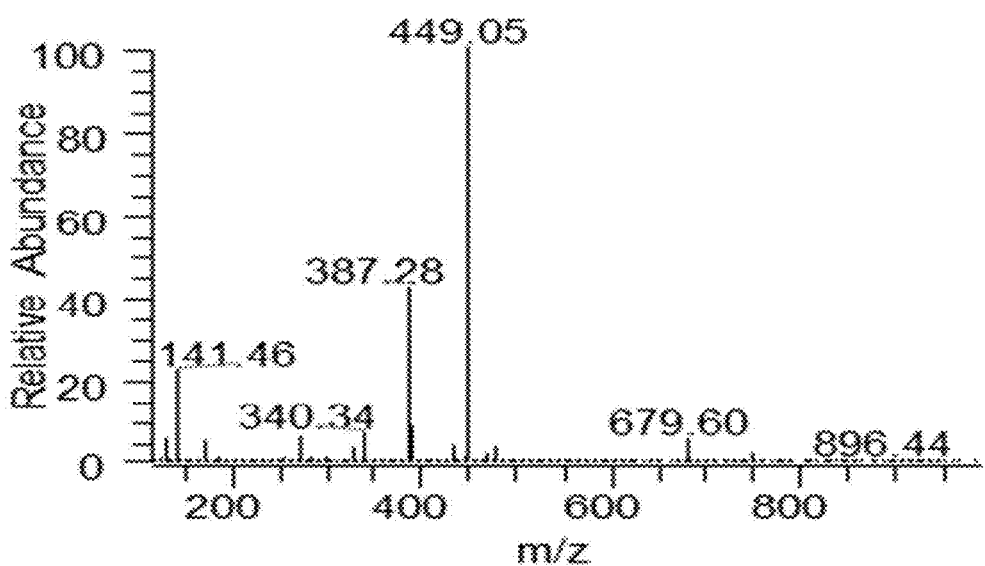
FIG. 31 is a graph showing MS spectrum of peak 2.
Figure 32:
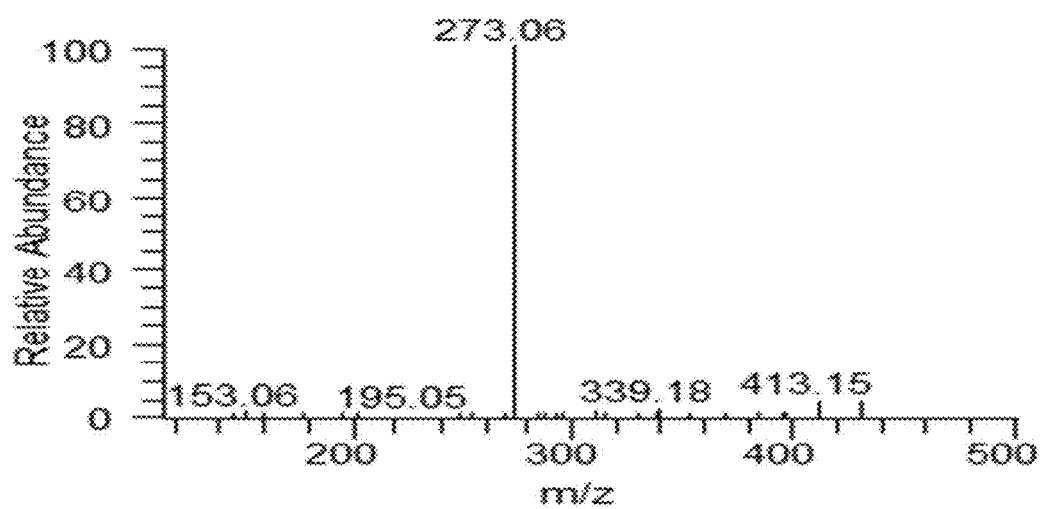
FIG. 32 is a graph showing MS2 spectrum of peak 2.
Figure 33:
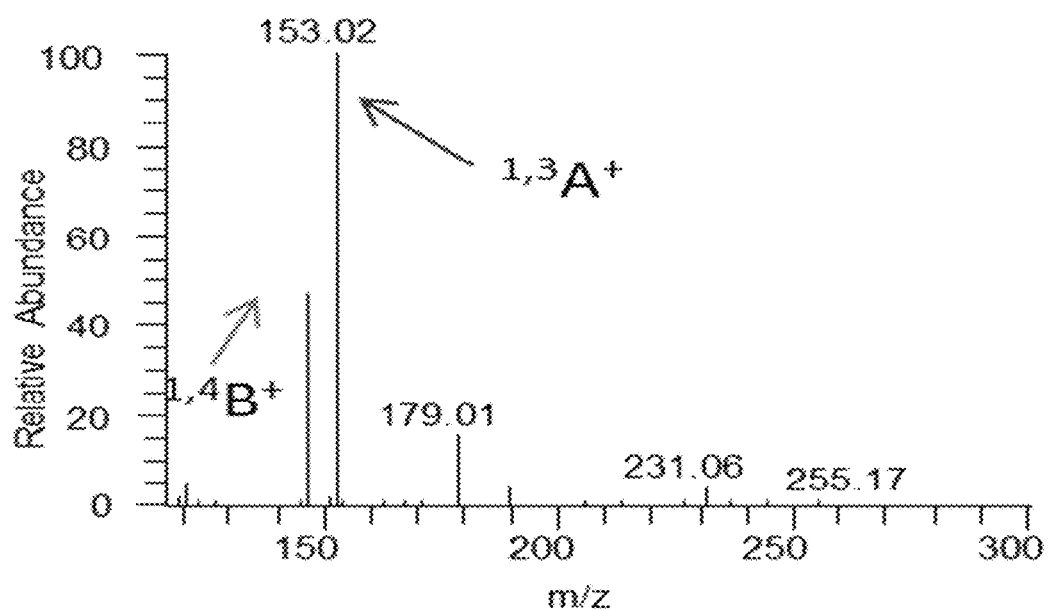
FIG. 33 is a graph showing MS3 spectrum of peak 2.
Figure 34A:
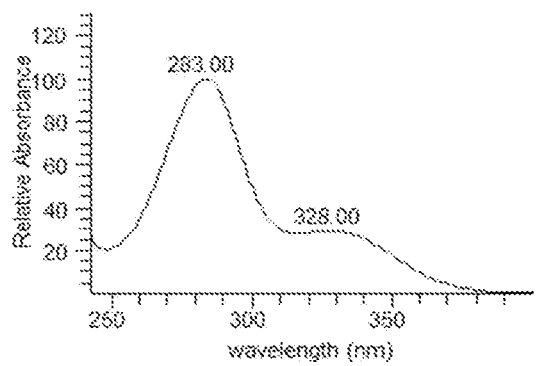
FIG. 34A is a graph showing the UV spectrum of peak 2 and FIG. 34 B shows the predicted fractionation patterns of the compound.
Figure 34B:
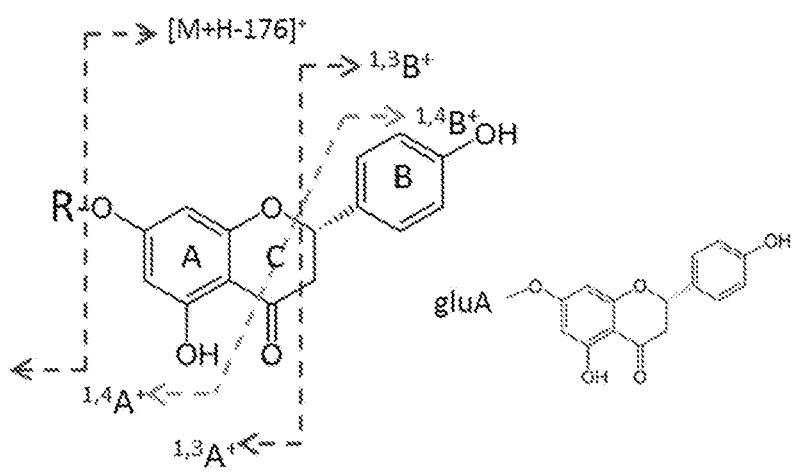

Further analysis of the compound derived from naringenin represented in peak 1 is shown in FIGS. 26-34. FIG. 26 shows absorption and mass spectrometry analysis of naringenin glucoside, seen as peak 1 (arrow). The MS spectrum of peak 1 is shown in the graph of FIG. 27, the MS2 spectrum of peak 1 in FIG. 28 and the UV spectrum in FIG. 29A along with the predicted fractionation patterns of the compound shown in FIG. 29B. In FIG. 30 absorption and mass spectrometry analysis of naringenin glucuronic acid is seen as peak 2 (arrow). The MS spectrum of peak 2 is shown in the graph of FIG. 31, the MS2 spectrum of peak 2 in FIG. 32, MS3 spectrum of peak 2 in FIG. 33 and UV spectrum in FIG. 34A along with the predicted fractionation patterns of the compound shown in FIG. 34B.

Thus use of the elicitor with a trapping agent and precursor produces new compounds of value. Particularly useful are those which add a carbohydrate to the moiety. Compounds produced include glucosides as well as glucuronides. Glucuronidation is important for drug metabolism in humans and to date there are no efficient means to make these compounds. In a representative example here, hairy roots were treated with precursor chrysin or naringenin, trapping agent cyclodextrin and an elicitor to produce chrysin glucoside and chrysin glucouronide, as well as naringenin glucoside and narigenin glucuronide and other novel compounds, as confirmed by UV and MS analysis. The process thus can produce valuable biological compounds that do not otherwise have efficient means of production.

Continued tracking of production of the product of interest shows amount of the product continued to increase over at least a 90 hours period.

Example 3. Biosynthesis Enhancement of Steroidal Alkaloids in Cell Suspension Cultures of *Veratrum californicum*

*Veratrum californium* is the only source of the potent anticancer alkaloid cyclopamine. Due to the complex chemical structure of this steroidal alkaloid its production through chemical synthesis is not commercially feasible. In efforts to develop a sustainable bioproduction system for cyclopamine and related steroidal alkaloids we developed cell suspension and adventitious root cultures of *V. californicum*. We demonstrated by HPLC and mass spectrometry analyses that several important steroidal alkaloids including cyclopamine, cycloposine, veratramine and veratrosine can be produced by these plant cultures. In order to increase the levels of these compounds we are treating cell suspension cultures of *V. californicum* with squalene (a biosynthetic precursor), cyclodextrin and methyl jasmonate.

Cell suspension cultures of *V. californium* are maintained in a modified MS medium under constant shaking under darkness at 24° C. At a specific stage of development, the spent medium is being removed and replaced with fresh medium containing between 0.5 to 75 mM of □-cyclodextrin, such as 15 mM of □-cyclodextrin (trapping agent) and between 10 to 500 □M methyl jasmonate, such as 100 □M methyl jasmonate (MeJA, inducer) with or without between 0.5 to 10 mM squalene, such as 1 mM squalene. Cultures are incubated for additional 24 hours as described above and then the cells and medium are collected. The steroidal alkaloids are extracted from the cells with methanol and from the culture medium with dichloromethane. The extracts are dried to completeness under nitrogen stream, resuspended in methanol and analyzed by reversed phase HPLC coupled with an ion-trap mass spectrometer. Detection and quantitation of the steroidal alkaloids is done by mass spectrometry.

Effect of Elicitation Period on the Levels of Arachidin-1 and Arachidin-3 in Hairy Root Cultures of Peanut.

Figure 35:
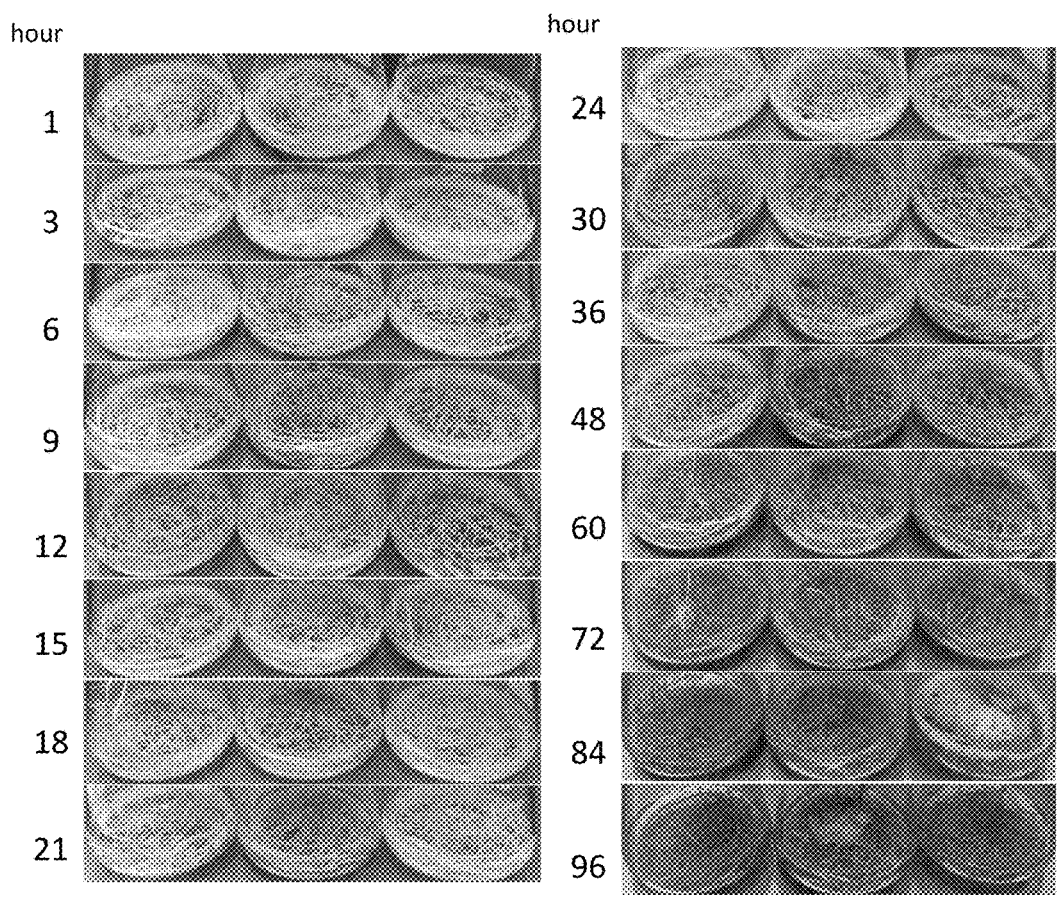
FIG. 35 is a view of one embodiment of the present invention applied to hairy root cultures of peanut.

Hairy roots of peanut cv. Hull line 3 were cultured for 9 days in a modified Murashige & Skoog medium at 28° C., under shaking (90 rpm) and continuous darkness. At day 9, the spent medium was removed and replaced with fresh medium containing the following treatments: a) =between 10 to 500 µM of methyl jasmonate, such as 100 µM methyl jasmonate (elicitor) combined with 0.9 to 90 g/L of methyl-β-cyclodextrin such as 9 g/L of methyl-β-cyclodextrin (trapping agent), b) 1 to 50 mM sodium acetate such as 10.2 mM sodium acetate, c) 10 to 500 µM methyl jasmonate such as 100 □M methyl jasmonate and d) 1 to 50 mM hydrogen such as 10 mM hydrogen peroxide. Control cultures included ethanol (solvent of methyl jasmonate) only. Cultures were incubated for different periods as shown in FIG. 35. At the end of each period the medium was harvested and stilbenoids (arachidin-1 and arachidin-3) were extracted with ethyl acetate. Afterward, this organic fraction was dried to completeness under nitrogen stream. The extract was resuspended in methanol and analyzed by reversed phase HPLC. Detection was done with a photodiode array detector. Arachidin-1 and arachidin-3 presence was confirmed by comparison to the retention times and UV spectra of authentic arachidin-1 and arachidin-3 standards and preliminary mass spectrometry analysis. Quantification of arachidin-1 and arachidin-3 was done by HPLC using a calibration curve of authentic standards.

Figure 36:
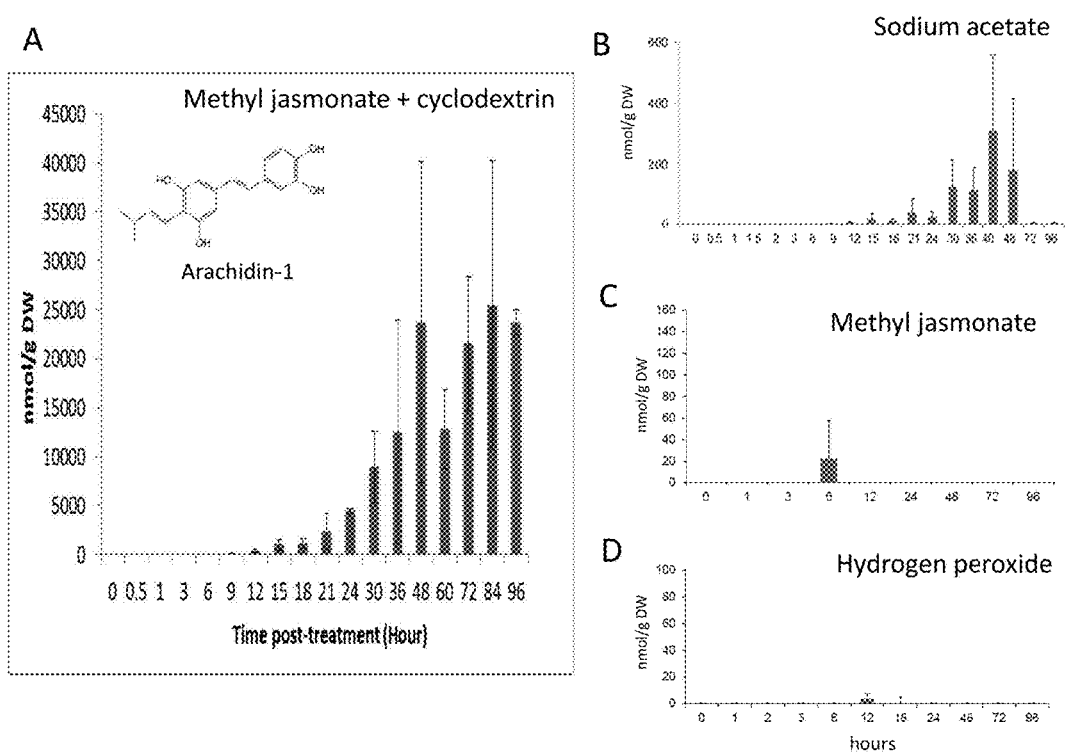
FIG. 36 is a graph showing accumulation of arachidin-1 of one embodiment of the present invention.
Figure 37:
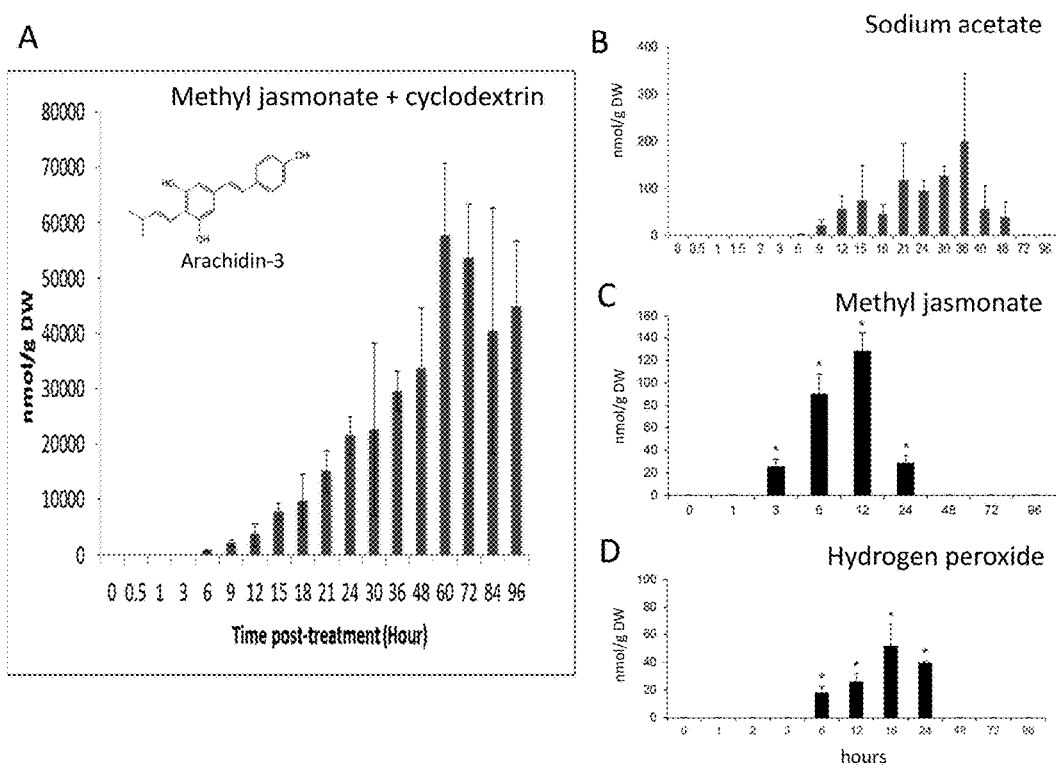
FIG. 37 is a graph showing accumulation of arachidin-3 of one embodiment of the present invention.

FIGS. 36 and 37 show the levels of arachidin-1 and arachidin-3, respectively, in the culture medium after treatment with either (A) 10 to 500 µM such as 100 µM methyl jasmonate in combination with 0.9 to 90 g/L such as 9 g/L methyl-β-cyclodextrin, (B) 1 to 50 mM such as 10.2 mM sodium acetate, (C) 10 to 500 µM such as 100 µM methyl jasmonate and (D) 1 to 50 mM such as 10 mM hydrogen peroxide. The levels of arachidin-1 (FIG. 36) are between 100 and 4000 times higher depending on the elicitation period in cultures treated with methyl jasmonate combined with cyclodextrin (FIG. 1A) versus any of the other elicitor treatments (FIGS. 36B, 36C, and 36D). Similarly, the levels of arachidin-3 (FIG. 37) are between 250 and 1000 times higher depending on the elicitation period in the treatment with methyl jasmonate combined with cyclodextrin versus any of the other elicitor treatments (FIGS. 37B, 37C, and 37D). As shown, the levels of arachidin-1 and arachidin-3 decline to almost non detectable levels after 48 h when the cultures were treated with any of the elicitors alone (sodium acetate, methyl jasmonate or hydrogen peroxide). However, when methyl jasmonate is combined with the trapping agent cyclodextrin, the production of arachidin-1 and arachidin-3 can be maintained at very high levels in the culture medium.

FIG. 35 shows the treatment of hairy root cultures of peanut with 100 M methyl jasmonate combined with 9 g/L of methyl-β-cyclodextrin for different periods. The yellowish color of the cultures is associated with the production of arachidin-1 and arachidin-3.

FIG. 36 shows the time course of accumulation of arachidin-1 after elicitor treatment in hairy root cultures of peanut. The cultures were treated with the following elicitors: (A) 100 µM methyl jasmonate in combination with 9 g/L of methyl-β-cyclodextrin, (B) 10.2 mM sodium acetate, (C) 100 mM methyl jasmonate and (D) 10 mM hydrogen peroxide. Arachidin-1 levels were determined by HPLC in ethyl acetate extracts from the culture medium. Each bar represents the average±standard deviation of the yield in ng per gram dry weight (DW) of root of three biological replicates.

FIG. 37 shows the time course of accumulation of arachidin-3 after elicitor treatment in hairy root cultures of peanut. The cultures were treated with the following elicitors: (A) 100 µM methyl jasmonate in combination with 9 g/L of methyl-β-cyclodextrin, (B) 10.2 mM sodium acetate, (C) 100 mM methyl jasmonate and (D) 10 mM hydrogen peroxide. Arachidin-1 levels were determined by HPLC in ethyl acetate extracts from the culture medium. Each bar represents the average±standard deviation of the yield in ng per gram dry weight (DW) of root of three biological replicates.

In another embodiment the precursor could include but not limited to resveratrol, phenylalanine, acetate, or coumaroyl-CoA. The trapping agent could be a macroporous resin including but not limited to XAD-7.

Biosynthesis Enhancement of Stilbenoids in Hairy Roots Cultures of Muscadine Grape Treated with Methyl Jasmonate Combined with Cyclodextrin and Piceatannol.

Hairy roots of muscadine grape were cultured for 21 days in a modified Murashige & Skoog medium at 28° C., under shaking (90 rpm) and continuous darkness. At day 21, the spent medium was removed and replaced with fresh medium containing either 100 µM methyl jasmonate (elicitor) alone or 100 µM methyl jasmonate combined with 7.5 mM methyl-β-cyclodextrin (trapping agent) and 1 mM piceatannol (putative precursor). Control cultures included ethanol (solvent of methyl jasmonate) only. Cultures were incubated for 24 hours under either treatment. At the end of the treatment, the medium was harvested and stilbenoids were extracted with ethyl acetate. Afterward, this organic fraction was dried to completeness under nitrogen stream. The extract was resuspended in methanol and analyzed by reversed phase HPLC. Detection was done with a photodiode array detector. The presence of the stilbenoids resveratrol, piceid and δ-viniferin was confirmed by comparison to the retention times and UV spectra of authentic standards and preliminary mass spectrometry analysis. Quantification of the stilbenoids was done by HPLC using a calibration curve of authentic standards.

In another embodiment, the spent medium was removed and replaced with fresh medium containing either between 10 to 500 µM methyl jasmonate (elicitor) alone or between 10 to 500 µM methyl jasmonate combined with between 0.5 to 75 mM methyl-β-cyclodextrin (trapping agent) and between 0.5 to 10 mM piceatannol (putative precursor). In another embodiment the precursor could include but not limited to phenylalanine, coumaric acid or coumaroyl CoA. In another embodiment, the trapping agent could be a macroporous resin including but not limited to XAD-7. In another embodiment, the elicitor could be but not limited to cellulase, yeast extract, chitosan The levels of resveratrol, piceid and viniferin in the culture medium are on average 208, 17, and 6 ng/g DW, respectively, under the treatment with the elicitor methyl jasmonate alone. However when methyl jasmonate is combined with the trapping agent methyl-β-cyclodextrin and the putative precursor piceatannol, the levels of resveratrol, piceid and viniferin increase to 33922, 3896 and 496 ng/g DW of root, respectively. These yields represent between 83 and 229 fold increase in production levels.

Figure 38:
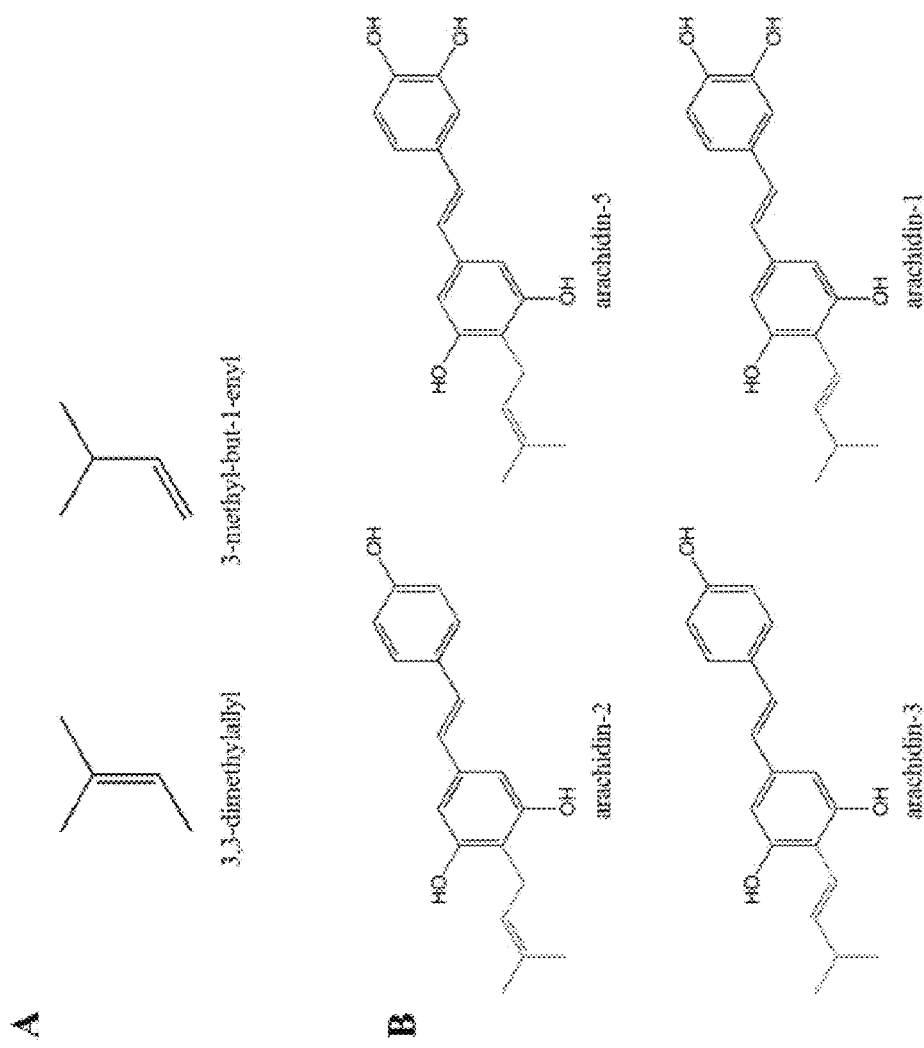
FIG. 38 is a chemical structure view of prenylated stilbenoids of one embodiment of the present invention.

Yield Optimization and Purification of Prenylated Stilbenoids from Peanut Hairy Roots 1 Introduction Peanut (*Arachis hypogaea*) produces prenylated stilbenoids as phytoalexins for defense against microbial infection. These stilbenoid derivatives have shown a diverse range of biological activities related to human health. Two major prenylated stilbenoids, arachidin-1 and arachidin-3 isolated from peanut kernels upon the treatment with imbibation, germination, slicing, and incubation with artificial aeration, displayed antioxidant and anti-inflammatory activities similar to their metabolic precursor, resveratrol (Chang et al., 2006). The anticancer activity of arachidin-1 isolated from germinating peanut kernels was demonstrated in HL-60 cells through caspase-dependent and caspase-independent pathways (Huang et al., 2010). Arachidin-1 and arachidin-3 purified from peanut hairy root cultures exhibited antiviral activity in rotavirus infected HT29.f8 cells by inhibiting rotavirus replication (Ball et al., 2015). This antiviral activity was not observed with either of their non-prenylated analogs, piceatannol or resveratrol, suggesting the antiviral mechanism might depend on the isoprenyl moiety (3-methyl-1-butenyl moiety) of arachidin-1 and arachidin-3. A cannabinoid receptor binding study of different peanut stilbenoids also demonstrated that the isoprenyl moiety of arachidin-1 and arachidin-3 improved binding affinity to type II cannabinoid receptor (Brents et al., 2012). Despite the diverse bioactivities of arachidin-1 and arachidin-3 demonstrated in in vitro studies, the limited availability of these prenylated stilbenoids has hindered their further progress for in vivo studies. Moreover, the bioactivities of arachidin-5 and arachidin-2, two other prenylated stilbenoids identified from peanut with 3,3-dimethylallyl moiety instead of that on arachidin-1 and arachidin-3 (FIG. 38) have not been explored due to their overall low yield or purity. FIG. 38. (A) Prenylation patterns present on prenylated stilbenoids. (B) Chemical structures of four main prenylated stilbenoids identified in elicited peanut hairy root culture. All compounds are shown in their trans isomers.

To increase the limited availability of prenylated stilbenoids, peanut hairy root culture has been developed as a sustainable production platforms for inducible stilbenoids (Condori et al., 2010; Yang et al., 2015) and the effect of various elicitors on the prenylated stilbenoid production were documented (Yang et al., 2015). Compared to a single elicitor, co-treatment of methyl jasmonate (MeJA) and cyclodextrin (CD) led a substantial increase on arachidin-1 and arachidin-3 accumulation in the medium of peanut hairy root culture. However, elicitation conditions with more than two elicitors have not been tested. To optimize the elicitation medium for maximum yield of prenylated stilbenoids, especially arachidin-1 and arachidin-3, we selected MeJA, a common signaling compound that mediates the induction the biosynthesis of stilbenoids, CD having capacity of trapping stilbenoids to potentially prevent feedback inhibition and $H_2O_2$ which induces piceatannol accumulation in peanut hairy root cultures as multiple elicitors for the elicitation medium (Yang et al., 2015). In addition, the concentration of magnesium ($Mg^{2+}$), a co-factor of resveratrol prenyltransferase(s) which is key enzyme involved in prenylated stilbenoid biosynthesis in peanut (Yang et al., 2016), was also optimized.

Conventionally, one-factor-at-a-time method designs which involve varying one parameter at a time and keeping the others constant are used for optimization of culture medium conditions (i.e. nutrients, temperature, pH, etc.). However, this one-dimensional evaluation usually does not lead to optimal conditions due to ignoring the effects of interaction among the various parameters. On the other hand, full-factorial experimental designs which consider all various parameters and their interactions are extremely time consuming especially for a large number of parameters. Orthogonal arrays are highly fractional factorial experimental designs which separate the individual effects of multiple variables in viable tests with reliable results. These methods have been successfully applied to the optimization of culture media for the enhancement of primary and secondary metabolites production in fermentation processes (reviewed by Rao et al., 2008), but not of elicitor conditions to increase the production of inducible metabolites in hairy root cultures. In this study, orthogonal array was applied for optimization of arachidin-1 and arachidin-3 yield in peanut hairy root cultures with multiple elicitation conditions (i.e. concentrations of $H_2O_2$, $Mg^{2+}$, MeJA and CD). After optimization, an efficient purification method for arachidin-1, arachidin-2, arachidin-3 and arachidin-5 from peanut hairy root culture medium was developed using high performance countercurrent chromatography (HPCCC) combined with semi-preparative high performance liquid chromatography (HPLC).

2 Materials and Methods 2.1 Growth Condition and Elicitation of Hairy Root Culture Hairy root line 3 used in this study was previously established from peanut cv. Hull (Condori et al., 2010) and maintained in 250 mL flasks with 50 mL of MSV media as previously described (Yang et al., 2015). Nine-day-old peanut hairy root were used for the yield optimization of prenylated stilbenoids from the culture medium. Prior to elicitation, the spent medium was removed and replaced with 50 mL or 100 mL of fresh MSV medium containing 3% sucrose with different concentration of elicitors. All elicitations were carried out at 28° C. under continuous darkness.

2.2 Orthogonal Array Design for the Optimization of Elicitation Medium

There are four key elicitation factors, MeJA, CD, $H_2O_2$ and $MgCl_2$ which may affect the production of prenylated stilbenoids in peanut hairy root cultures. These four factors, each at four levels for the orthogonal array design are listed in FIG. 39. The orthogonal array is expressed by its number of rows and columns, as well as by the number of levels in each column. For example, the matrix of an $L_{16}$ ($4^4$) array used in this study has 16 rows and 4 four-level columns. Each row represents a special combination with the level of elicitors in the elicitation medium and each column represents various levels of one elicitor. To be orthogonal, each level of elicitor occurs equally often in every column and each level of one elicitor pairs equally with all four levels of other elicitors without pairing repetition (FIG. 40).

Based on the orthogonal array, the peanut hairy root culture was elicited with each combination of elicitors. Each elicitor treatment included two biological replicates and 1 mL of culture medium was collected at 48 hour and 72 hour time points of elicitation to determine the concentration of stilbenoids. The prenylated stilbenoids were extracted by an equal volume of ethyl acetate and quantified by HPLC as described previously (Ball et al., 2015). The production of arachidin-1 and arachidin-3 from each combination was recorded on the right side of the orthogonal array in FIG. 40.

FIG. 39. Elicitation factor and their levels on the orthogonal array design.

Figure 40:
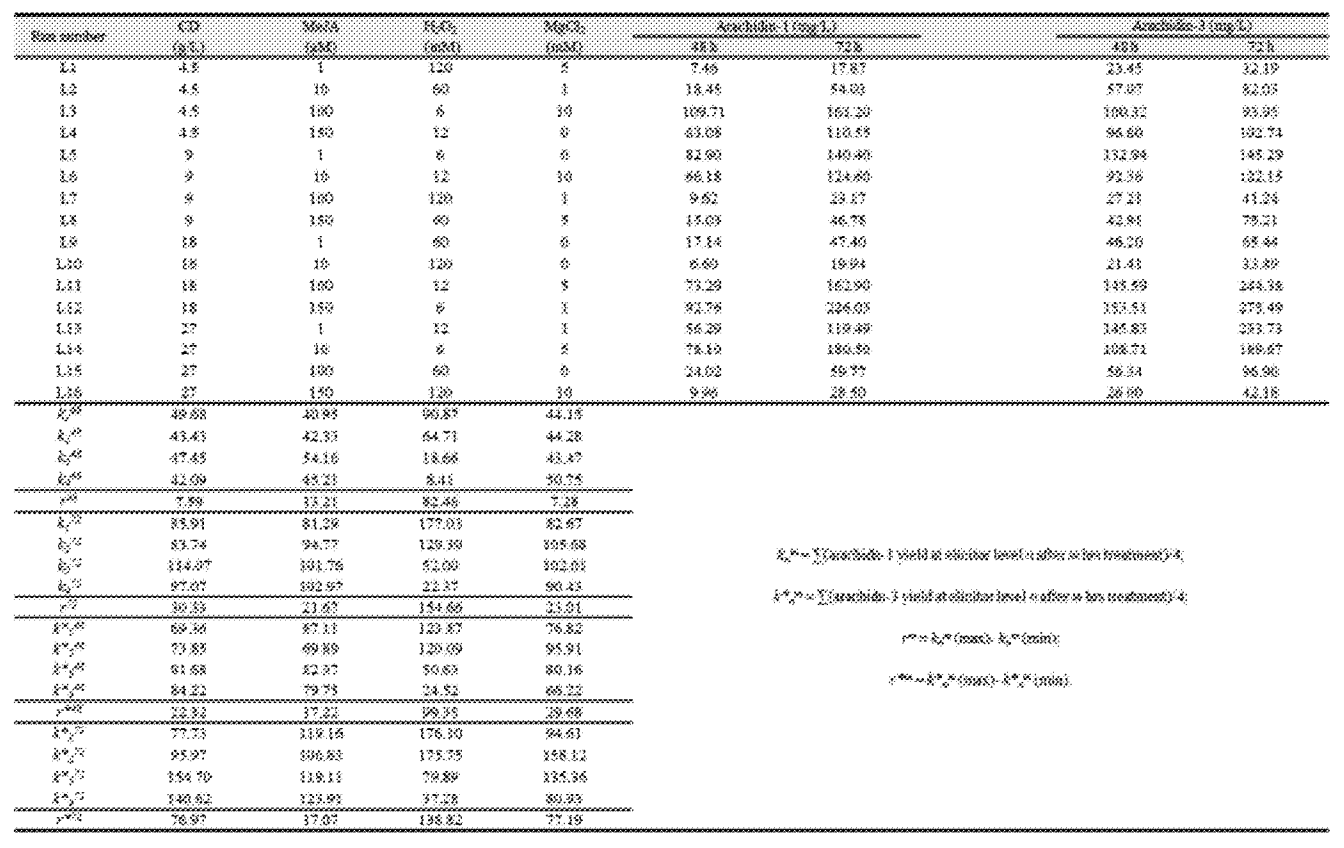

FIG. 40. Results and analysis of orthogonal array design $L_{16}$ ($4^4$). Production of arachidin-1 and arachidin-3 in peanut hairy root culture upon the treatment with each combination of elicitors on the orthogonal array are listed on right. Explanation of k and r values used for orthogonal analysis is described in Materials and Methods.

To determine the optimal concentration of each elicitor for prenylated stilbenoids production, the average values of arachidin-1 and arachidin-3 yields in mg/L for each factor at level n (n=1, 2, 3 or 4) after m hours (m=48 or 72) treatment was calculated as $k_n^m$ and $k*_n^m$, respectively (recorded below the orthogonal array in FIG. 40). In the orthogonal analysis, optimum concentrations of each elicitor for arachidin-1 or arachidin-3 production are those that may result in the largest k value. For example, the k values of arachidin-1 in the 72 hours treatment group for various concentrations of CD, $k_1^{72}$, $k_2^{72}$, $k_3^{72}$ and $k_4^{72}$ are 85.91, 83.74, 114.07 and 97.07, respectively. As the highest k value among others, $k_3^{72}$ indicated the optimal concentration of CD for maximizing arachidin-1 production. Therefore the optimal concentration should be at level 3 (18 g/L).

To evaluate the contribution of each elicitor to prenylated stilbenoids production, the absolute difference among $k_n^m$ and $k*_n^m$ for each factor was measured by $r^m$ and $r*^m$, respectively. If the r value of one elicitor is higher than that of other elicitors, the concentration of this elicitor in elicitation medium may have a higher effect on prenylated stilbenoid production when comparing to others.

2.3 Purification of Prenylated Stilbenoids Using HPCCC and Semi-Preparative HPLC To purify prenylated stilbenoids, each 250 mL flask of peanut hairy root culture was treated with 100 mL of optimal elicitation medium (18 g/L CD, 125 µM MeJA, 3 mM $H_2O_2$ and additional 1 mM $MgCl_2$ in MSV medium) for 168 hours treatment. Then the culture medium was extracted with 100 mL of ethyl acetate and the ethyl acetate extract was dried in a rotary evaporator. Then this crude extract (280-300 mg from each 250 mL flask) was subjected to HPCCC using a Dynamic Extractions HPCCC system as described previously (Ball et al., 2015). In brief, the HPCCC solvent system containing hexane:ethyl acetate:methanol:water (4:5:3:3, v/v/v/v) was mixed well and separated in a separatory funnel. The upper phase of the solvent system, which was used as the stationary phase, was flushed in the column at 8 mL/min flow rate. The rotor started to run at 1600 rpm and the lower phase was then introduced at 6 mL/min. After the equilibrium was established, the crude extract was resuspended in 3 mL of upper and 3 mL of lower phase, mixed well and then injected into the column. The eluent from the rotor was monitored at UV 340 nm. The fraction containing arachidin-5 and arachidin-1 (eluted at 25.5~28.5 min) and the fraction containing arachidin-2 and arachidin-3 (eluted at 42.0~49.0 min) were collected and dried in a SpeedVac.

The dried arachidin-5/arachidin-1 and arachidin-2/arachidin-3 fractions isolated from HPCCC were resuspended in methanol and then subjected to semi-preparative HPLC for further purification. The separation was performed on a semi-preparative column (SunFire $C_{18}$, 5 µm, 10×250 mm, Waters) at room temperature in an UltiMate 3000LC system (Dionex; Thermo Scientific). The mobile phase consisted of water (A) and methanol (B). The column was initially equilibrated with 60:40 (A:B). Then solvent B was linearly increased to 50% for 2 min (0-2 min), and further then increase to 70% for 48 min (2-50 min) and held at 100% for 5 mins (50-55 min), and return to the initial condition of 60:40 (A:B) in 5 min. The highly purified (over 98% purity in analytical HPLC analysis) arachidin-5, arachidin-1, arachidin-2 and arachidin-3 were dried in a SpeedVac and weighted with an analytical balance.

3 Result and Discussion 3.1 Orthogonal Arrays Design for Optimization of Prenylated Stilbenoid Production Previous studies have shown that the stilbenoid biosynthesis pathway can be induced by various elicitors in peanut hairy root cultures and also most stilbenoids secreted to the medium of the peanut hairy root cultures (Yang et al., 2015). After co-treatment with MeJA and CD for 48-96 hour, the average yields of arachidin-1 and arachidin-3 can reach about 56 and 148 mg/L (approximately equivalent to 5.6 and 14.8 mg/g dry weight of peanut hairy root), which were much higher than the maximum yield of these compounds isolated from aerated and sliced peanut seeds (0.496 mg/g and 2.415 mg/g dry weight of peanut kernel for arachidin-1 and arachidin-3) (Chang et al., 2006). To further increase the levels of prenylated stilbenoids in peanut hairy root culture, the concentrations of MeJA, CD, $H_2O_2$ and extra $MgCl_2$ in the elicitation medium were evaluated using orthogonal array design. The assignment of parameters with various levels are given in FIG. 39. The level 2 value of CD (9 g/L) was based on the previous study (Yang et al., 2015). The level 1, level 3 and level 4 values of CD were half, twice and triple of the level 2 value, respectively. The level values of MeJA and $H_2O_2$ were determined by the preliminary trials (data not shown). The maximum concentration of magnesium, 10 mM of $MgCl_2$ used in the orthogonal array was referred to the saturated concentration of magnesium in a previously described flavonoid-specific prenyltransferase reaction (Akashi et al., 2008; Sasaki et al., 2008; Sasaki et al., 2011; Chen et al., 2013; Li et al., 2014).

Based on the matrix of an $L_{16}$ ($4^4$) orthogonal array design, we carried out only 16 experiments instead of at least 256 experiments in full-factorial experimental design to reach the similar results with this variety of factors and levels. Every experimental condition and the production of arachidin-1 and arachidin-3 after 48 hours and 72 hours treatment under its condition are listed in FIG. 40. In brief, according the r values, the influence of the elicitation medium on the production of arachidin-1 after 48 and 72 hours treatment was $H_2O_2$>>MeJA>CD~$MgCl_2$ and $H_2O_2$>CD>$MgCl_2$>MeJA, respectively. The influence on the arachidin-3 production were $H_2O_2$>$MgCl_2$>CD>MeJA at both 48 and 72 hours treatment group. Hydrogen peroxide was found to be the most important determinant or the arachidin-1 and arachidin-3 production. The largest values among the $k_n^m$ and $k*_n^m$ of $H_2O_2$ factor were $k_1^{48}$, $k_1^{72}$, $k*_1^{48}$ and $k*_1^{72}$ indicated the level 1 value, 6 mM $H_2O_2$, lead highest yield of arachidin-1 and arachidin-3 comparing to other levels. It might be caused by the potential of oxidative damage from high level of $H_2O_2$ to the peanut hairy root tissue and also suggested lower concentration of $H_2O_2$ need to be tested. Considering priority to the yield of arachidin-1 and arachidin-3 at 72 hours treatment group, the concentration of CD and $MgCl_2$ that were additionally added in the elicitation medium were optimized to 18 g/L (level 3) and 1 mM (level 2) respectively due to the highest values of the $k^{72}$ values for CD were $k_3^{72}$ and $k*_3^{72}$ and that for $MgCl_2$ were $k_2^{72}$ and $k*_2^{72}$. For the MeJA factor, the $k_3^{48}$>$k_4^{48}$, $k_3^{72}$<$k_4^{72}$ and $k*_3^{48}$>$k*_4^{48}$, $k*_3^{72}$<$k*_4^{72}$ suggested the concentration of MeJA needed to be tested further between the 100 µM (level 3) and 150 µM (level 4).

The combinations of $H_2O_2$ from 1.5 mM to 6 mM and MeJA from 100 µM to 150 µM were tested to further optimize the concentrations of these two factors with 18 g/L CD and 1 mM $MgCl_2$ co-treatment in 50 mL elicitation medium. The production of arachidin-1 and arachidin-3 after 48 hours and 72 hours treatment under these conditions are listed in FIG. 41. The group treated with 3 mM $H_2O_2$ and 125 µM MeJA had the highest yield of arachidin-1 with 231.75 mg/L and the second highest yield of arachidin-3 with 300.76 mg/L, which was slightly lower than the highest yield, 314.30 mg/L in the 1.5 mM $H_2O_2$ and 125 µM MeJA treated group. Thus, the optimal elicitation medium for the production of arachidin-1 and arachidin-3 in peanut hairy root was composed of 18 g/L CD, 125 µM MeJA, 3 mM $H_2O_2$ and additional 1 mM $MgCl_2$ in MSV medium. Moreover, despite the original purpose of the optimization for elicitation medium was to increase the yields of arachdin-1 and arachidin-3, the production of arachidin-5, arachidin-2 and other prenylated stilbenoid derivatives (including arachidin-5 derivative and arachidin-2 derivative) were also tremendously improved in peanut hairy root cultures upon the treatment of this optimal elicitation medium (FIG. 42), providing a rich biological source of peanut stilbenoids for further purification and application.

Figure 43:
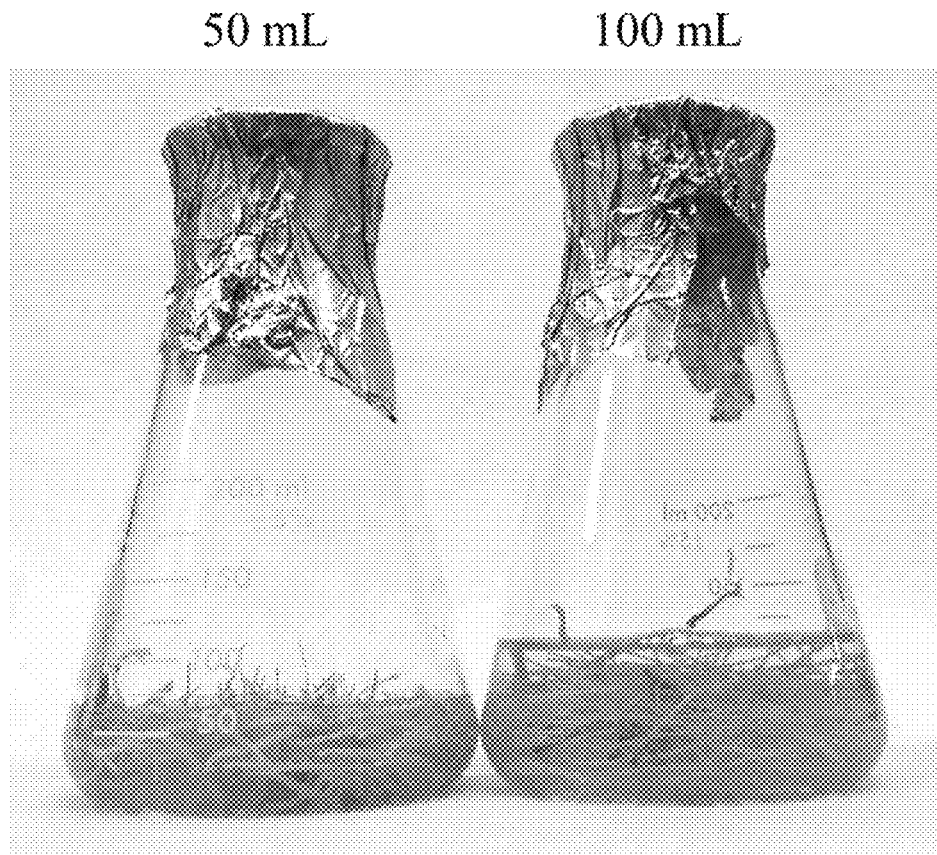
FIG. 43 is a comparison view of one embodiment of the present invention.
Figure 44:
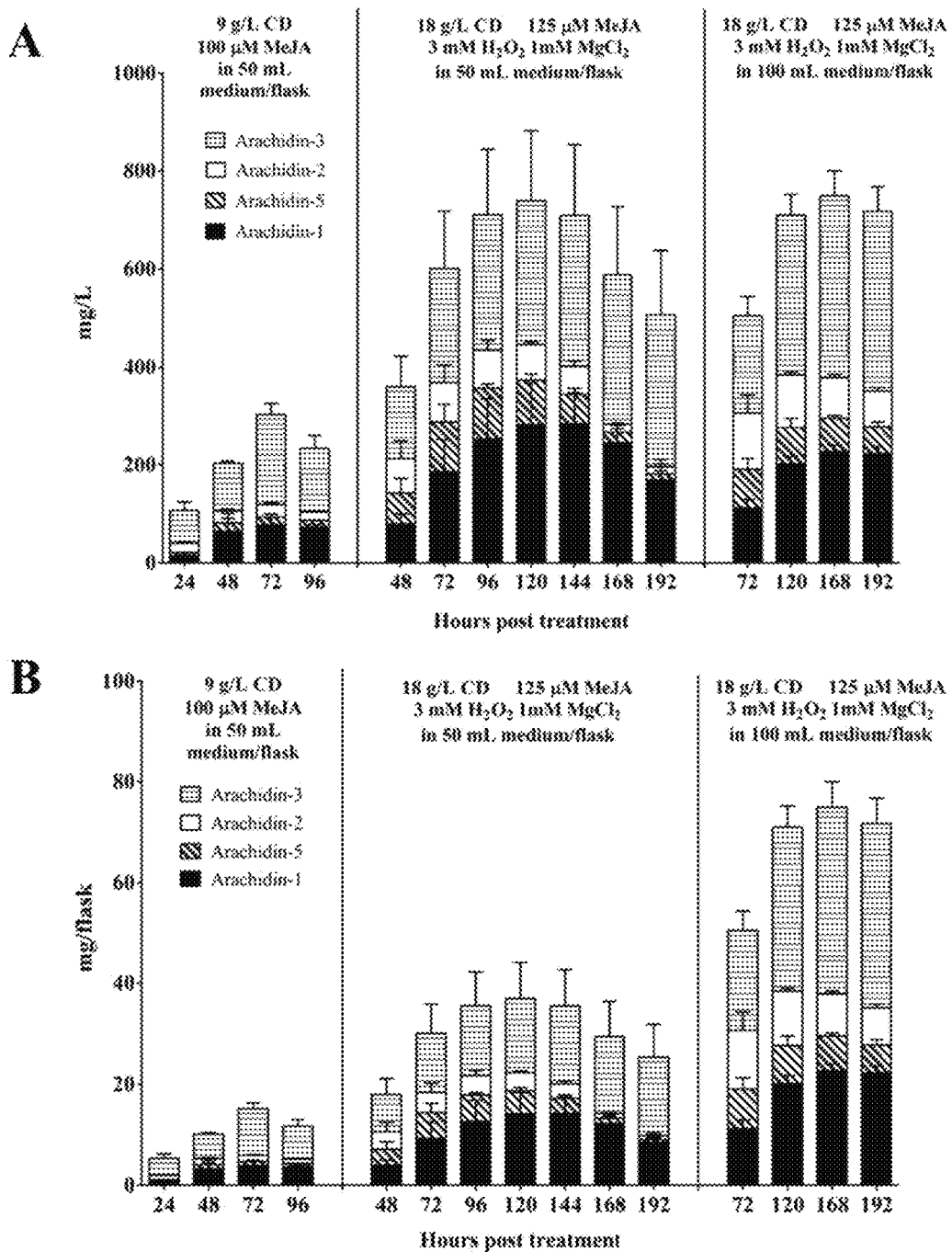
FIG. 44 is a comparison view of one embodiment of the present invention.

FIG. 41. Effects of MeJA and $H_2O_2$ on the production of arachidin-1 and arachidin-3 in peanut hairy root culture co-treated with 18 g/L CD and 1 mM $MgCl_2$ During the elicitation, the root tissue of nine-day-old peanut hairy root was not completely immersed in 50 mL elicitation medium resulting in some of the root tissue still standing above the medium in a 250 mL flask (FIG. 43). This might affect the elicitation and stilbenoids secretion of root tissue which was not contacted with medium and lower the productivity of prenylated stilbenoids from the single flask. To address this issue, a larger volume (100 mL) of elicitation medium was applied to peanut hairy roots in a 250 mL flask to ensure entire root tissue was immersed and the production of arachidin-1 and arachidin-3 were compared with that from 50 mL elicitation medium in a time course experiment. In the 50 mL volume group, the concentrations of arachidin-1 and arachidin-3 were accumulated after 72 hours, reached their plateau around 120 hours and started to decline after 144 hours (FIG. 44). In contrast, arachidin-1 and arachidin-3 from the 100 mL volume group met their highest concentration after 168 hours treatment with 227.39±12.75 mg/L and 370.59±50.37 mg/L respectively and did not show significantly decrease at 192 hours (FIG. 45, FIG. 44A). To compare the production efficiency in one single 250 mL flask under different conditions, the production of arachidin-1 and arachidin-3 were normalized in mg per flask (FIG. 46, FIG. 43B). Under treatment with 100 µM MeJA alone, only trace amounts of arachidin-3 were detected at 48 hours (FIG. 46) and none of arachidin-1 and arachidin-3 was detected in the HPLC after 72 hour treatment (FIG. 42A). Comparing to the 72 hour treatment with 9 g/L CD and 100 µM MeJA, the optimum elicitation medium treatment in 100 mL elicitation volume for 72 hours and 168 hours respectively had 7.23 fold and 14.67 fold increase in arachidin-1 yield and 2.82 fold and 5.29 fold increase in arachidin-3 yield (FIG. 46). The variation in arachidin-1 and arachidin-3 production from the 100 mL volume group is less than that from the 50 mL volume group (FIG. 44), suggesting that 100 mL elicitation medium for 250 mL flask might provide a consistent system for production of arachidin-1 and arachidin-3 in peanut hairy root cultures. In addition, even arachidin-5 (with maximum production of 7.86±2.23 mg) and arachidin-2 (with maximum production of 11.6±3.62 mg) from the 100 mL volume group were constantly decreased after 72 hours treatment, the yield of this two compounds from one single flask were much higher than from 50 mL volume group (FIG. 44B).

Figure 42:
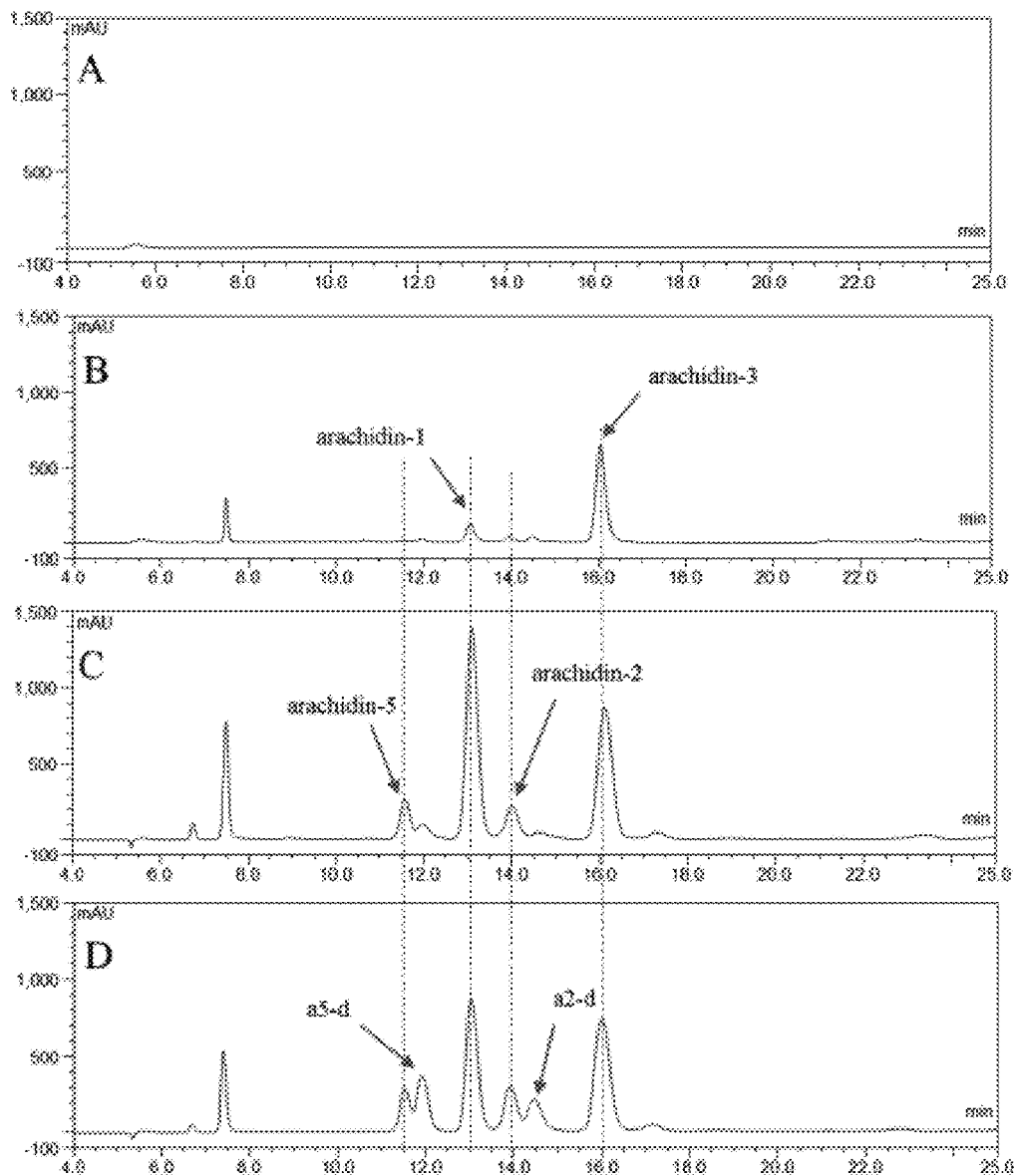
FIG. 42 is a table view showing chromatograms of one embodiment of the present invention.

FIG. 42. HPLC chromatograms (UV 340 nm) of ethyl acetate extracts from the medium of peanut hairy root culture after 72 hours treatment with different conditions: (A) 100 µM MeJA, (B) 100 µM MeJA 9 g/L CD and (C) 125 µM MeJA, 18 g/L CD, 3 mM $H_2O_2$ and 1 mM $MgCl_2$ in a 50 mL elicitation medium; (D) 125 µM MeJA, 18 g/L CD, 3 mM $H_2O_2$ and 1 mM $MgCl_2$ in a 100 mL elicitation medium. a5-d, arachidin-5 derivative; a2-d, arachidin-2 derivative.

FIG. 43. Comparison of peanut hairy root culture treated with 50 mL elicitation medium and 100 mL elicitation medium. Nine-day-old peanut hairy root were treated with 125 µM MeJA, 18 g/L CD, 3 mM $H_2O_2$ and 1 mM $MgCl_2$ in a 50 mL (left) and 100 mL (right) elicitation medium.

FIG. 41. Comparison of the concentration (A) and the yield of prenylated stilbenoids from one 250 mL flask (B) in peanut hairy root cultures under different elicitation conditions.

FIG. 45. Time courses of arachidin-1 and arachidin-3 production in peanut hairy root culture co-treated with 3 mM $H_2O_2$, 125 µM MeJA, 18 g/L CD and 1 mM $MgCl_2$ in different volume.

FIG. 46. Arachidin-1 and arachidin-3 productions from the medium of peanut hairy root culture upon various elicitation conditions.

Prenylated stilbenoids were induced by various elicitor(s) and elicitation medium volumes. The yield of arachidin-1 or arachidin-3 secreted into the culture medium was quantified by HPLC and normalized in mg of each 250 mL flask.

Overall, the optimum elicitation medium for the production of arachidin-1 and arachidin-3 was composed of 18 g/L CD, 125 µM MeJA, 3 mM $H_2O_2$ and additional 1 mM $MgCl_2$ in MSV medium. The maximum yield of prenylated stilenoids from each 250 mL flask was 74.95±7.49 mg in total, including 22.74±1.28 mg of arachidin-1, 37.06±5.04 mg of arachidin-3, 6.84±0.57 mg of arachidin-5 and 8.31±0.61 mg of arachidin-2, after 168 hour treatment with 100 mL optimal elicitation medium.

3.2 Purification of Prenylated Stilbenoids from Peanut Hairy Root Culture

Figure 47:
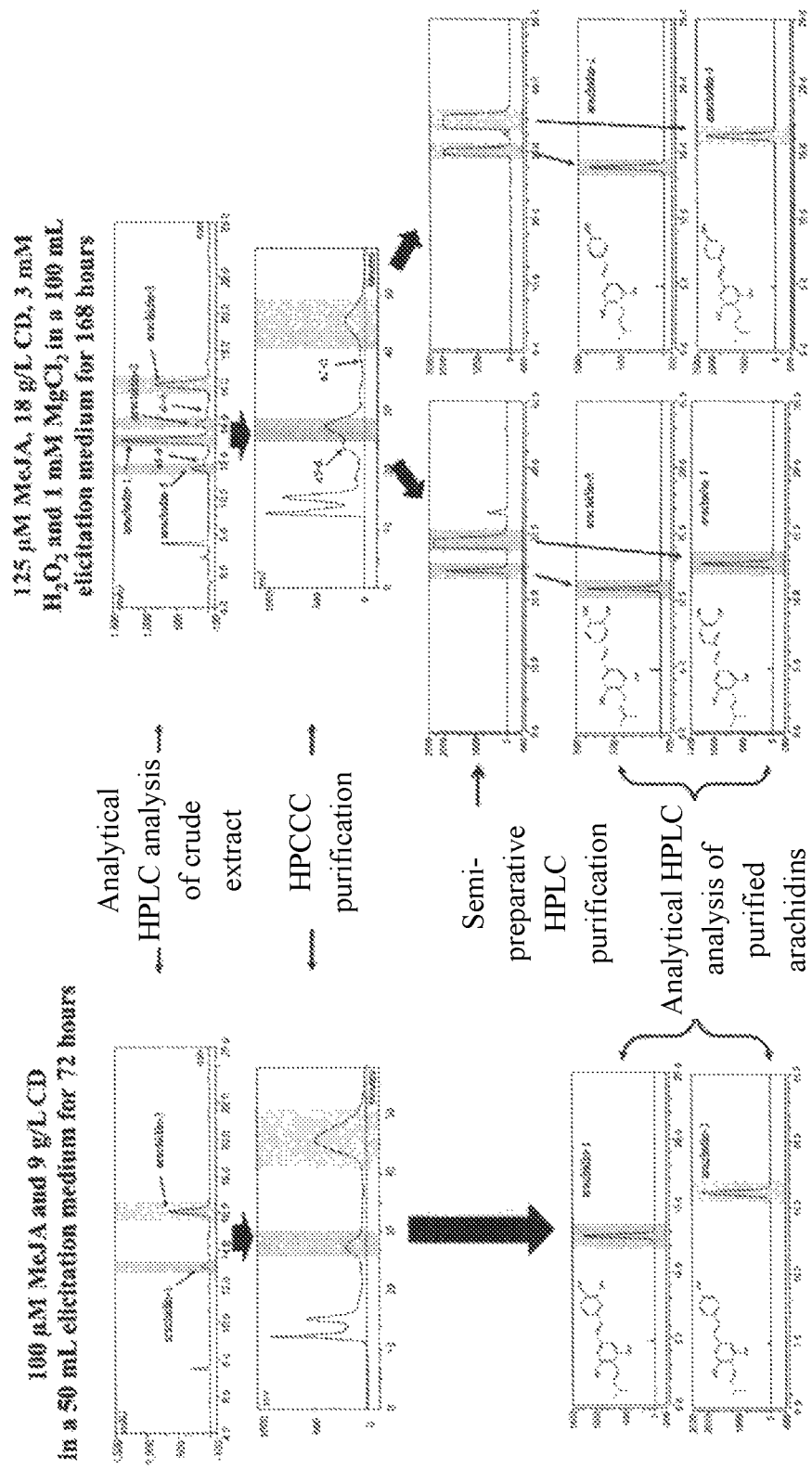
FIG. 47 is a flowchart showing prenylated stilbenoids purification of one embodiment of the present invention.

Arachidin-1 and arachidin-3 from the peanut hairy root culture upon 100 µM MeJA and 9 g/L CD treatment have been successfully purified using HPCCC (Ball et al., 2015; Yang et al., 2015, FIG. 47). However, under the elicitation of optimal condition, not only arachidin-1 and arachidin-3, but their analogs, such as arachidin-5, arachidin-2, arachidin-5 and arachidin-2 derivatives were significantly increased in yield and this change on stilbenoid profile made their purification more complex. Despite arachidin-1 and arachidin-3 having a good separation in HPCCC, either arachidin-5 and arachidin-1 or arachidin-2 and arachidin-3 co-eluted out and could not be isolated from each other due to the high similarity on their chemical structure (FIG. 47). In the crude extract purification trial on a semi-preparative HPLC column, we found that both arachidin-5 (tR: 25.1 min) and arachidin-2 (tR: 31.8 min) were isolated from arachidin-1 (tR: 29.2 min) and arachidin-3 (tR: 36.8 min) respectively. But the tight interval between adjacent stilbenoids, especially that between arachidin-1 and arachidin-2, limited the sample amount of peanut crude extract for each HPLC run, resulting in a low productivity on prenylated stilnenoids with high purity (over 95%). Fortunately, both arachidin-5 derivative and arachidin-2 derivative could be separated from arachidin-5/arachidin-1 or arachidin-2/arachidin-3 fractions through HPCCC (FIG. 48), as a result, a two-step method was developed for high efficiency and purification of various arachidins. In this method, every 300 mg of crude extract extracted from 100 mL culture medium of each flask was injected into HPCCC all at once. Arachidin-5/arachidin-1 fractions and arachidin-2/arachidin-3 fractions were collected, concentrated and further applied to semi-preparative HPLC respectively (FIG. 47). At the end, roughly at least 1.5 mg of arachidin-5, 10 mg of arachidin-1, 1.3 mg of arachidin-2 and 10 mg of arachidin-3 with over 98% purity could be purified from each culture flask.

FIG. 47. Comparison of previous and new two-step strategy for prenylated stilbenoids purification from peanut hairy root culture. In previous strategy (left), peanut hairy root was elicited with 100 µM MeJA and 9 g/L CD in a 50 mL elicitation medium for 72 hours. Arachidin-1 and arachidin-3 were isolated from the ethyl acetate extract of culture medium using HPCCC. In new two-step strategy (right), prenylated stilbenoids were induced by 125 µM MeJA, 18 g/L CD, 3 mM H$_2$O$_2$ and 1 mM MgCl$_2$ in a 100 mL of elicitation medium for 168 hours. The crude extract containing the arachidins was subjected to HPCCC first, and then fractions containing the arachidins were subjected to semi-preparative HPLC to purify arachidin-5, arachidin-1, arachidin-2 and arachidin-3.

Figure 48:
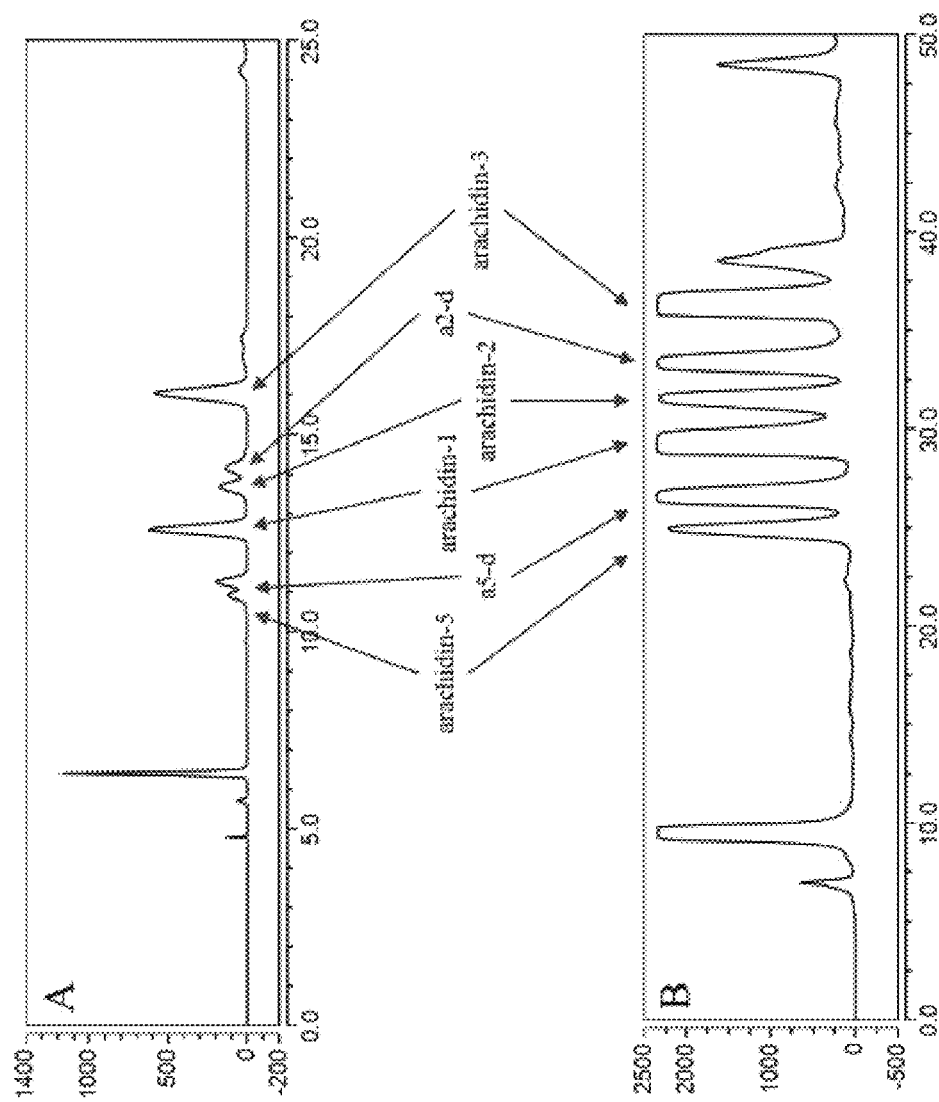
FIG. 48 is a table view showing chromatograms of one embodiment of the present invention.

FIG. 48. Analytical (A) and semi-preparative (B) HPLC chromatograms (UV 320 nm) of ethyl acetate extracts from the medium of peanut hairy root culture after 168 hours treatment with 125 M MeJA, 18 g/L CD, 3 mM H$_2$O$_2$ and 1 mM MgCl$_2$ in a 100 mL elicitation medium. a5-d, arachidin-5 derivative; a2-d, arachidin-2 derivative.

REFERENCES

Aggarwal, B. B., Bhardwaj, A., Aggarwal, R. S., Seeram, N. P., Shishodia, S., and Takada, Y. (2004) Role of Resveratrol in Prevention and Therapy of Cancer: Preclinical and Clinical Studies. Anticancer Res. 24:1-60.

Akashi T, Sasaki K, Aoki T, Ayabe S, Yazaki K (2008) Molecular cloning and characterization of a cDNA for pterocarpan 4-dimethylallyltransferase catalyzing the key prenylation step in the biosynthesis of glyceollin, a soybean phytoalexin. Plant Physiol 149: 683-693

Babu S K, Kumar K V, Subbaraju G V (2005) Estimation of trans-resveratrol in herbal extracts and dosage forms by high-performance thin-layer chromatography. Chem Pharm Bull 53:691-693. DOI 10.1248/cpb.53.691

Ball J M, Medina-Bolivar F, Defrates K, Hambleton E, Hurlburt M E, Fang L, Yang T, Nopo-olazabal L, Atwill R L, Ghai P, et al (2015) Investigation of stilbenoids as potential therapeutic agents for rotavirus gastroenteritis. Adv Virol 2015: 1-10

Baur J, Sinclair D A (2006) Therapeutic potential of resveratrol: the in vivo evidence. Nat Rev Drug Discov. 5:493-506

Becker J, Armstrong G O, van der Merwe M J, Lambrechts M J, Vivier M A, Pretorius I S (2003) Metabolic engineering of *Saccharomyces cerevisiae* for the synthesis of the wine-related antioxidant resveratrol. FEMS Yeast Res 4:79-85.

Brents L K, Medina-Bolivar F, Seely K a., Nair V, Bratton S M, Nopo-Olazabal L, Patel R Y, Liu H, Doerksen R J, Prather P L, et al (2012) Natural prenylated resveratrol analogs arachidin-1 and -3 demonstrate improved glucuronidation profiles and have affinity for cannabinoid receptors. Xenobiotica 42: 139-156

Bru R, Selles S, Casado-Vela J, Belchi-Navarro S, Pedreno M A (2006) Modified cyclodextrins are chemically defined glucan inducers of defense responses in grapevine cell cultures. J Agri Food Chem. 54-65-71

Camilleri, C., Jouanin, L., 1991. The TR-DNA region carrying the auxin synthesis genes of the *Agrobacterium rhizogenes* agropine-type plasmid pRiA4: nucleotide sequence analysis and introduction into tobacco plants. Mol. Plant Microbe Interact. 4, 155-162.

Caspeta L, Quintero R, Villarreal M L (2005) Novel airlift reactor fitting for hairy root cultures: developmental and performance studies. Biotechnol Prog. 21:735-740

Celimene C, Micales J, Ferge L, Young R (1999) A. Efficacy of pinosylvins against white-rot and brown-rot fungi. Holzforschung. 53: 491-497

Chen R, Liu X, Zou J, Yin Y, Ou B, Li J, Wang R, Xie D, Zhang P, Dai J (2013) Regio- and stereospecific prenylation of flavonoids by Sophoraflavescens prenyltransferase. Adv Synth Catal 355: 1817-1828

Chen R S, Wu P L, Chiou R Y (2002) Peanut roots as a source of resveratrol. J Agric Food Chem. 50:1665-1667

Chang, J-C., Lai, Y-H., Djoko, B., Wu, P.-L., Liu, C.-D., Liu, Y-W., and Chiou, R., Y-Y. (2006) Biosynthesis enhancement and antioxidant and anti-inflammatory activities of peanut arachidin-1, arachidin-3, and isopentadienylresveratrol. J. Agric. Food Chem. 54:10281-10287.

Chung I M, Park M R, Rehman S, Yun S J (2001) Tissue specific and inducible expression of resveratrol synthase gene in peanut plants. Mol Cells 12:353-359

Condori J, Medina-Bolivar F (2006) *Agrobacterium rhizogenes* strain ATCC 15834 plasmid pRi 15834 3-indoleacetamide hydrolase (aux2) and trytophan 2-monooxygenase (aux1) genes, complete cds. NCBI Accession No. DQ782955

Condori J, Sivakumar G, Hubstenberger J, Dolan M C, Sobolev V S, Medina-Bolivar F (2010) Induced biosynthesis of resveratrol and the prenylated stilbenoids arachidin-1 and arachidin-3 in hairy root cultures of peanut: Effects of culture medium and growth stage. Plant Physiol Biochem 48: 310-318

Delmas D, Lancon A, Colin D, Jannin B, Latruffe N (2006) Resveratrol as a chemopreventive agent: a promising molecule for fighting cancer. Curr Drug Targets 7:423-442

Frankel E, Waterhouse A, Kinsella J (1993) Inhibition of human LDL oxidation by resveratrol. Lancet. 341:1103-1104.

Gamborg O L, Miller R A, Ojima K (1968) Nutrient requirements of suspension cultures of soybean root cells. Exp Cell Res 50:151-158

Gehm B D, McAndrews J M, Chien P Y, Jameson J L (1997) Resveratrol, a polyphenolic compound found in grapes and wine, is an agonist for the estrogen receptor. Proc Natl Acad Sci 94:14138-14143

Guillon S, Tremouillaux-Guiller J, Pati P K, Rideau M, Gantet P (2006) Hairy root research: recent scenario and exciting prospects. Curr Opi Plant Biol. 9:341-346

Hall D, De Luca V (2007) Mesocarp localization of a bi-functional resveratrol/hydroxycinnamic acid glucosyltransferase of Concord grape (*Vitis labrusca*). Plant J 49: 579-591.

Holsters M, de Waele D, Depicker A, Messens E, van Montagu M, Schell J (1998) Transfection and transformation of *Agrobacterium tumefaciens*. Mol Gen Genet. 163-181-187.

Huang C-P, Au L-C, Chiou R Y-Y, Chung P-C, Chen S-Y, Tang W-C, Chang C-L, Fang W-H, Lin S-B (2010) Arachidin-1, a peanut stilbenoid, induces programmed cell death in human leukemia HL-60 Cells. J Agric Food Chem 12123-12129

Huang Y, Tsai W, Shen C, Chen C (2005) Resveratrol derivatives from the roots of *Vitis thunbergii*. J Nat Prod 68: 217-220

Jeandet P, Douillet-Breuil A C, Bessis R, Debord S, Sbaghi M, Adrian M. (2002) Phytoalexins from the Vitaceae: biosynthesis, phytoalexin gene expression in transgenic plants, antifungal activity, and metabolism. J. Agric. Food. Chem. 50:2731-41.

Komarnytsky S, Gaume A, Garvey A, Borisjuk N, Raskin I (2004) A quick and efficient system for antibiotic-free expression of heterologous genes in tobacco roots. Plant Cell Rep. 22: 765-773

Kopp P (1998) Resveratrol, a phytoestrogen found in red wine. A possible explanation for the conundrum of the 'French paradox'? Eur J Endocrinol. 138:619-620

Larronde F, Richard T, Delaunay J C, Decendit A, Monti J P, Krisa S, Mérillon J M (2005) New stilbenoid glucosides isolated from *Vitis vinifera* cell suspension cultures (cv. Cabernet Sauvignon). Planta Med 71:888-890. DOI 10.1055/s-2005-871294

Lee J, Jung E, Lim J, Lee J, Hur S, Kim S S, Lim S, Hyun C G, Kim Y S, Park D. (2006) Involvement of nuclear factor-kappaB in the inhibition of pro-inflammatory mediators by pinosylvin. Planta Med. 72:801-806.

Li J, Chen R, Wang R, Liu X, Xie D, Zou J, Dai J (2014) GuA6DT, a regiospecific prenyltransferase from *glycyrrhiza uralensis*, catalyzes the 6-prenylation of flavones. ChemBioChem 15: 1673-1681

Medina-Bolivar F, Wright R, Funk V, Sentz D, Barroso L, Wilkins T, Petri Jr. W, Cramer C (2003) A non-toxic lectin for antigen delivery of plant-based mucosal vaccines. Vaccine 21:997-1005

Medina-Bolivar F, Cramer C (2004) Production of recombinant proteins in hairy roots cultured in plastic sleeve bioreactors In: Balbas P, Lorence A (eds) Recombinant gene expression: Reviews and protocols. Humana Press, Totowa, pp 351-363

Mikstacka, R., Rimando, A. M., Szalaty, K., Stasik, K., and Baer-Dubowska, W. (2006) "Effect of natural analogues of trans-resveratrol on cytochromes P4501A2 and 2E1 catalytic activities". Xenobiotica, 36: 269-285.

Miura D, Miura Y, Yagasaki K (2003) Hypolipidemic action of dietary resveratrol, a phytoalexin in grapes and red wine, in hepatoma-bearing rats. Life Sciences 73:1393-1400. DOI 10.1016/S0024-3205(03)00469-7 http://dx.doi.org/10.1016/S0024-3205%2803%2900469-7

Nepote V, Grosso N R, Guzman C A (2004) Radical scavenging activity of extracts of argentine peanut skins (*Arachis hypogaea*) in relation to its trans-resveratrol content. J Argent Chem Soc 92:41-49

Nopo-Olazabal L, Woffenden B, Reed D, Buswell S, Zhang C, Medina-Bolivar F. Differential expression of the "super-promoter" in leaves and hairy roots of tobacco. 2005 In Vitro Biology Meeting, Abstract P-2037

Orallo F (2006) Comparative studies of the antioxidant effects of cis- and trans-resveratrol. Curr Med Chem. 13:87-98

Park E J, Min H Y, Ahn Y H, Bae C M, Pyee J H, Lee S K. (2004) Synthesis and inhibitory effects of pinosylvin derivatives on prostaglandin E2 production in lipopolysaccharide-induced mouse macrophage cells. Bioorg Med Chem Lett. 14:5895-5898.

Pitta-Alvarez, S., Giulietti, A., 1999. Influence of chitosan, acetic acid and citric acid on growth and tropane alkaloid production in transformed roots of *Brugmansia candida* Effect of medium pH and growth phase. Plant Cell Tissue Org. Cult. 59, 31-38.

Ramakrishnan D, Curtis W R (2004) Trickle-bed root culture bioreactor design and scale-up: growth, fluid-dynamics, and oxygen mass transfer. Biotechnol. Bioeng. 88:248-260.

Rao R S, Kumar C G, Prakasham R S, Hobbs P J (2008) The Taguchi methodology as a statistical tool for biotechnological applications: a critical appraisal. Biotechnol J 3: 510-23

Rimando A M, Barney D L (2005) Resveratrol and naturally occurring analogues in *Vaccinium* species. Acta Horticulture Proceedings 6:137-143

Rimando A M, Nagmani R, Feller D R, Yokoyama W (2005) Pterostilbene, a new agonist for the peroxisome proliferator-activated receptor α-isoform, lowers plasma lipoproteins and cholesterol in hypercholesterolemic hamsters. J Agric Food Chem 53:3403-3407

Roupe, K., Remsberg, C., Yanez, J., Davies, N., 2006a. Pharmacometrics of stilbenes: seguing towards the clinic. Curr. Clin. Pharm. 1, 81-101.

Roupe, K., Yanez, J., Teng, X. W., and Davies, N., 2006b. Pharmacometrics of selected stilbenes: srhapontigenin, piceatannol, pinosylvin. J. Pharm. Pharmacol. 58, 1443-1450.

Rudolf J R, Resurreccion A V (2005) Elicitation of resveratrol in peanut kernels by application of abiotic stresses. J Agric Food Chem 53:10186-10192. DOI 10.1021/jf0506737

Sasaki K, Mito K, Ohara K, Yamamoto H, Yazaki K (2008) Cloning and characterization of naringenin 8-prenyltransferase, a flavonoid-specific prenyltransferase of *Sophora flavescens*. Plant Physiol 146: 1075-1084

Sasaki K, Tsurumaru Y, Yamamoto H, Yazaki K (2011) Molecular characterization of a membrane-bound prenyltransferase specific for isoflavone from Sophoraflavescens. J Biol Chem 286: 24125-24134

Savary B, Flores H (1994) Biosynthesis of defense-related proteins in transformed root cultures of *Trichosanthes kirilowii* Maxim. var *japonicum* (Kitam.). Plant Physiol 106:1195-1204

Schmülling, T., Schell, J., Spena, A., 1988. Single genes from *Agrobacterium rhizogenes* influence plant development. EMBO J. 7, 2621-2629.

Slightom, J. L., Durand-Tardif, M., Jouanin, L., Tepfer, D., 1986. Nucleotide sequence analysis of TL-DNA of *Agrobacterium rhizogenes* agropine type plasmid. Identification of open reading frames. J. Biol. Chem. 261, 108-121.

Soleas G J, Angelini M, Grass L, Diamandis E P & Goldberg D M. (2001) Absorption of trans-resveratrol in rats. Methods Enzymol., 335:145.

Tabata Y, Takano K, Ito T, Iinuma M, Yoshimoto T, Miura H, Kitao Y, Ogawa S, Hori O. (2007) "Vaticanol B, a resveratrol tetramer, regulates endoplasmic reticulum (ER) stress and inflammation." Am J Physiol Cell Physiol. E-Published; doi:10.1152/ajpcell.00095.2007

Tassoni A, Fornalè S, Franceschetti M, Musiani F, Michael A J, Perry B, Bagni N (2005) Jasmonates and Na-orthovanadate promote resveratrol production in *Vitis vinifera* cv. Barbera cell cultures. New Phytologist 166: 895-905. DOI 10.1111/j.1469-8137.2005.01383.x Watts K T, Lee P C, Schmidt-Dannert C (2006) Biosynthesis of plant-specific stilbene polyketides in metabolically engineered *Escherichia coli*. BMC Biotechnology 6:22. DOI 10.1186/1472-6750-6-22

Wenzel, E., and Somoza, V., (2005) Metabolism and bioavailability of trans-resveratrol. Mol. Nutr. Food Res. 49:472-481.

White, F. F et al., (1985) J. Bacteriol., vol. 164, p. 33.

Wink M, Alfermann A W, Franke R, Wetterauer B, Distl M, Windhovel J, Krohn O, Fuss E, Garden H, Mohagheghzadeh A, Wildi E, Ripplinger P (2005) Sustainable bioproduction of phytochemicals by plant in vitro cultures: anticancer agents. Plant Gen Res. 3:90-100

Yan Q, Hu Z, Tan R X, Wu J (2005) Efficient production and recovery of diterpenoid tanshinones in *Salvia* miltiorrhiza hairy root cultures with in situ adsorption, elicitation and semi-continuous operation. J Biotechnol. 119:416-24

Yang T, Fang L, Nopo-Olazabal C, Condori J, Nopo-Olazabal L, Balmaceda C, Medina-Bolivar F (2015)

Enhanced production of resveratrol, piceatannol, arachidin-1, and arachidin-3 in hairy root cultures of peanut co-treated with methyl jasmonate and cyclodextrin. J Agric Food Chem 63: 3942-50

Yang T, Fang L, Rimando A M, Sobolev V, Mockaitis K, Medina-Bolivar F (2016) A stilbenoid-specific prenyltransferase utilizes dimethylallyl pyrophosphate from the plastidic terpenoid pathway. Plant Physiol 171: 2483-98

From the foregoing, it will be seen that the present invention is one well adapted to obtain all the ends and objects herein set forth, together with other advantages which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A method of increasing the production of a phenolic from a hairy root culture through biosynthesis, the method comprising:
contacting the hairy root culture capable of producing the phenolic with a cyclodextrin, a methyl jasmonate, and a magnesium chloride.

2. The method of claim 1 further comprising:
producing an increased amount of the phenolic compared to the method in which the hairy root culture is not contacted with the cyclodextrin, the methyl jasmonate, or the magnesium chloride.

3. The method of claim 2 wherein the phenolic is a prenylated stilbenoid.

4. The method of claim 2, the hairy root culture further comprising:
grape hairy roots.

5. The method of claim 2 the hairy root culture further comprising:
peanut hairy roots.

6. The method of claim 3 wherein the prenylated stilbenoid comprises arachidin.

7. The method of claim 1 wherein the methyl jasmonate, the cyclodextrin, and the magnesium chloride contact the hairy root culture for at least one hour.

8. The method of claim 1 further comprising:
contacting the hairy root culture with hydrogen peroxide.

9. The method of claim 8 wherein the methyl jasmonate, the cyclodextrin, and the hydrogen peroxide contact the hairy root culture at the same time in an elicitation medium.

10. The method of claim 6 wherein the methyl jasmonate, the cyclodextrin, and the magnesium chloride contact the hairy root culture at the same time in an elicitation medium.

11. A method of increasing the production of a prenylated stilbenoid from a hairy root culture through biosynthesis, the method comprising:
contacting the hairy root culture capable of producing the prenylated stilbenoid with a cyclodextrin, a methyl jasmonate, and a magnesium chloride.

12. The method of claim 11 wherein the prenylated stilbenoid comprises arachidin.

13. The method of claim 11 wherein the methyl jasmonate, the cyclodextrin, and the magnesium chloride contact the hairy root culture for at least one hour.

14. The method of claim 11 further comprising:
contacting the hairy root culture with hydrogen peroxide.

15. The method of claim 11 wherein the methyl jasmonate, the cyclodextrin, and the magnesium chloride contact the hairy root culture at the same time in an elicitation medium.

16. The method of claim 14 wherein the methyl jasmonate, the cyclodextrin, and the hydrogen peroxide contact the hairy root culture at the same time in an elicitation medium.

17. A method of increasing the production of a phenolic from a hairy root culture through biosynthesis, the method comprising:
contacting the hairy root culture capable of producing the phenolic with an elicitation medium comprising a cyclodextrin, a methyl jasmonate, and a magnesium chloride; and
producing an increased amount of the phenolic compared to the method in which the hairy root culture is not contacted with the cyclodextrin, the methyl jasmonate, or the magnesium chloride.

18. The method of claim 17 wherein the phenolic is a prenylated stilbenoid.

19. The method of claim 18, the elicitation medium further comprising:
hydrogen peroxide.

20. The method of claim 19 wherein the elicitation medium contacts the hairy root culture for at least one hour.

* * * * *